US009090891B2

(12) United States Patent
Madero et al.

(10) Patent No.: US 9,090,891 B2
(45) Date of Patent: Jul. 28, 2015

(54) PEN-SHAPED DEVICE FOR BIOLOGICAL SAMPLE PREPARATION AND ANALYSIS

(71) Applicant: CALIFORNIA INSTITUTE OF TECHNOLOGY, Pasadena, CA (US)

(72) Inventors: Xiomara Linnette Madero, Glendale, CA (US); Imran R Malik, Pasadena, CA (US); Erika F Garcia, Los Angeles, CA (US); Axel Scherer, Barnard, VT (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 132 days.

(21) Appl. No.: 14/070,465

(22) Filed: Nov. 1, 2013

(65) Prior Publication Data

US 2014/0057278 A1   Feb. 27, 2014

Related U.S. Application Data

(63) Continuation-in-part of application No. 13/407,644, filed on Feb. 28, 2012, now Pat. No. 8,883,088.

(60) Provisional application No. 61/722,355, filed on Nov. 5, 2012, provisional application No. 61/722,343, filed on Nov. 5, 2012, provisional application No. 61/725,373, filed on Nov. 12, 2012, provisional application No. 61/722,326, filed on Nov. 5, 2012, provisional application No. 61/580,035, filed on Dec. 23, 2011.

(51) Int. Cl.
*G01N 21/75* (2006.01)
*C12N 15/10* (2006.01)
*F17D 3/00* (2006.01)

(52) U.S. Cl.
CPC .............. *C12N 15/1017* (2013.01); *F17D 3/00* (2013.01); *G01N 21/75* (2013.01); *Y10T 137/8593* (2015.04)

(58) Field of Classification Search
CPC .................................................... G01N 21/75
USPC ........................................................ 422/417
See application file for complete search history.

(56) References Cited

U.S. PATENT DOCUMENTS

| | | |
|---|---|---|
| 4,930,361 A | 6/1990 | Nimberger |
| 5,196,830 A | 3/1993 | Birging |
| 5,272,518 A | 12/1993 | Vincent |
| 5,508,197 A | 4/1996 | Hansen |
| 5,820,265 A | 10/1998 | Kleinerman |
| 5,871,699 A | 2/1999 | Ruggeri |
| 6,222,619 B1 | 4/2001 | Herron et al. |
| 6,441,890 B2 | 8/2002 | Wardlaw et al. |
| 6,544,734 B1 | 4/2003 | Briscoe et al. |
| 6,902,112 B2 | 6/2005 | Sadler |
| 7,411,792 B2 | 8/2008 | Richards et al. |
| 7,564,541 B2 | 7/2009 | Tuschel |
| 7,754,153 B2 | 7/2010 | Miyamoto |
| 8,058,054 B2 | 11/2011 | Owen et al. |
| 8,071,385 B2 | 12/2011 | Haas et al. |
| 8,277,760 B2 | 10/2012 | Letho |
| 8,395,773 B2 | 3/2013 | Malik et al. |
| 2002/0046614 A1 | 4/2002 | Alley |
| 2002/0160534 A1 | 10/2002 | Herron et al. |
| 2003/0109806 A1 | 6/2003 | Weber et al. |
| 2004/0091862 A1 | 5/2004 | Brandenburg et al. |
| 2004/0152206 A1 | 8/2004 | Davis et al. |
| 2005/0024636 A1 | 2/2005 | Nakamura |
| 2005/0036142 A1 | 2/2005 | Oldham et al. |
| 2005/0042651 A1 | 2/2005 | Vann et al. |
| 2005/0059165 A9 | 3/2005 | Davis et al. |
| 2005/0099621 A1 | 5/2005 | Vaez-Iravani et al. |
| 2005/0109396 A1 | 5/2005 | Zucchelli et al. |
| 2005/0282266 A1 | 12/2005 | Teng et al. |
| 2006/0186346 A1 | 8/2006 | Wei |
| 2006/0211071 A1 | 9/2006 | Andre et al. |
| 2006/0233670 A1 | 10/2006 | Lehto |
| 2006/0289787 A1 | 12/2006 | Ohman et al. |
| 2006/0290934 A1 | 12/2006 | Boekelman |
| 2007/0084279 A1 | 4/2007 | Huang et al. |
| 2007/0272039 A1 | 11/2007 | Hermet et al. |
| 2008/0003649 A1 | 1/2008 | Maltezos et al. |
| 2008/0176230 A1 | 7/2008 | Owen et al. |
| 2008/0176755 A1 | 7/2008 | Amundson et al. |

(Continued)

FOREIGN PATENT DOCUMENTS

| | | |
|---|---|---|
| EP | 1972919 | 9/2008 |
| JP | 2002-139418 | 5/2002 |

(Continued)

OTHER PUBLICATIONS

PCT International Search Report mailed on Feb. 7, 2011 for PCT Application PCT/US2010/039389 filed on Jun. 21, 2010 in the name of California Institute of Technology et al.
PCT Written Opinion mailed on Feb. 7, 2011 for PCT Application PCT/US2010/039389 filed on Jun. 21, 2010 in the name of California Institute of Technology et al.
PCT International Search Report mailed on Feb. 3, 2014 for PCT Application PCT/US2013/068170 filed on Nov. 1, 2013 in the name of California Institute of Technology.
PCT Written Opinion mailed on Feb. 17, 2014 for PCT Application PCT/US2010/039389 filed on Jun. 21, 2010 in the name of California Institute of Technology et al.

(Continued)

*Primary Examiner* — Ardin Marschel
(74) *Attorney, Agent, or Firm* — Steinfl & Bruno LLP

(57) ABSTRACT

Methods and devices for biological sample preparation and analysis are disclosed. A device may have a circular arrangement of containers, with a connecting structure such as a disk. Fluidics channels between containers allow the performance of different techniques for sample preparation, such as lysing, washing and elution. The device may be pen-shaped and have a sample drawing needle connected to the containers.

14 Claims, 56 Drawing Sheets

(56) References Cited

U.S. PATENT DOCUMENTS

| | | |
|---|---|---|
| 2009/0050209 A1 | 2/2009 | Rautavuori |
| 2009/0176661 A1 | 7/2009 | Harding et al. |
| 2010/0051124 A1 | 3/2010 | Imran |
| 2010/0120164 A1 | 5/2010 | Salafsky |
| 2010/0152066 A1 | 6/2010 | Malik et al. |
| 2010/0192706 A1 | 8/2010 | Fairs et al. |
| 2010/0321696 A1 | 12/2010 | Malik et al. |
| 2011/0104026 A1 | 5/2011 | Yoon et al. |
| 2011/0151577 A1 | 6/2011 | Zhang et al. |
| 2011/0207313 A1 | 8/2011 | Lim et al. |
| 2011/0306120 A1 | 12/2011 | Nicholls et al. |
| 2012/0003631 A1 | 1/2012 | Yu et al. |
| 2012/0180882 A1 | 7/2012 | Malik et al. |

FOREIGN PATENT DOCUMENTS

| | | |
|---|---|---|
| JP | 2002-214225 | 7/2002 |
| JP | 2012-100549 | 5/2012 |
| WO | 00/21659 | 4/2000 |
| WO | 2007/102713 | 9/2007 |
| WO | 2011/005487 | 1/2011 |

OTHER PUBLICATIONS

PCT International Search Report mailed on Feb. 14, 2014 for PCT/US2013/068165 filed on Nov. 1, 2013 in the name of California Institute of Technology.
PCT Written Opinion mailed on Feb. 14, 2014 for PCT/US2013/068165 filed on Nov. 1, 2013 in the name of California Institute of Technology.
PCT International Search Report mailed on Feb. 5, 2014 for PCT/US2013/068172 filed on Nov. 1, 2013 in the name of California Institute of Technology.
PCT Written Opinion mailed on Feb. 5, 2014 for PCT/US2013/068172 filed on Nov. 1, 2013 in the name of California Institute of Technology.
Restriction Requirement mailed on Oct. 20, 2011 for U.S. Appl. No. 12/638,829, filed Dec. 15, 2009 in the name of Imran R. Malik et al.
Final Office Action mailed on Jan. 24, 2014 for U.S. Appl. No. 12/638,829, filed Dec. 15, 2009 in the name of Imran R. Malik et al.
Final Office Action mailed on Oct. 23, 2013 for U.S. Appl. No. 12/638,829, filed Dec. 15, 2009 in the name of Imran R. Malik et al.
Non-Final Office Action mailed on Dec. 16, 2011 for U.S. Appl. No. 12/638,829, filed on Dec. 15, 2009 in the name of Imran R. Malik et al.
Non-Final Office Action mailed on Oct. 3, 2013 for U.S. Appl. No. 12/638,829, filed Dec. 15, 2009 in the name of Imran R. Malik et al.
Final Office Action mailed on Oct. 10, 2012 for U.S. Appl. No. 12/820,104, filed Jun. 21, 2010 in the name of Imran R. Malik et al.
Non-Final Office Action mailed on Jun. 6, 2012 for U.S. Appl. No. 12/820,104, filed Jun. 21, 2010 in the name of Imran R. Malik et al.
Notice of Allowance mailed on Dec. 24, 2012 for U.S. Appl. No. 12/820,104, filed Jun. 21, 2010 in the name of Imran R. Malik et al.
Final Office Action mailed on Sep. 12, 2013 for U.S. Appl. No. 13/009,785, filed Jan. 19, 2011 in the name of Imran R. Malik et al.
Non-Final Office Action mailed on May 28, 2013 for U.S. Appl. No. 13/009,785, filed Jan. 19, 2011 in the name of Imran R. Malik et al.
Restriction Requirement mailed on Mar. 5, 2013 for U.S. Appl. No. 13/009,785, filed Jan. 19, 2011 in the name of Imran R. Malik et al.
Non-Final Office Action mailed on Nov. 26, 2013 for U.S. Appl. No. 13/407,644, filed Feb. 28, 2012 in the name of Imran R. Malik et al.
Restriction Requirement mailed on Sep. 17, 2013 for U.S. Appl. No. 13/407,644, filed Feb. 28, 2012 in the name of Imran R. Malik et al.
PCT Written Opinion mailed on Feb. 3, 2014 for PCT Application PCT/US2013/068170 filed on Nov. 1, 2013 in the name of California Institute of Technology.
PCT International Search Report mailed on Feb. 17, 2014 for PCT Application PCT/US2013/068171 filed on Nov. 1, 2013 in the name of California Institute of Technology.
PCT Written Opinion mailed on Feb. 17, 2014 for PCT Application PCT/US2013/068171 filed on Nov. 1, 2013 in the name of California Institute of Technology.
PCT International Search Report mailed on Feb. 6, 2014 for PCT Application PCT/US2013/068173 filed on Nov. 1, 2013 in the name of California Institute of Technology.
PCT Written Opinion mailed on Feb. 6, 2014 for PCT Application PCT/US2013/068173 filed on Nov. 1, 2013 in the name of California Institute of Technology.
PCT International Search Report mailed on Oct. 16, 2013 for PCT Application PCT/US2013/051461 filed on Jul. 22, 2013 in the name of California Institute of Technology.
PCT Written Opinion mailed on Oct. 16, 2013 for PCT Application PCT/US2013/051461 filed on Jul. 22, 2013 in the name of California Institute of Technology.
PCT International Search Report mailed Feb. 17, 2014 for PCT Application PCT/US2013/068169 filed on Nov. 1, 2013 in the name of California Institute of Technology.
Notice of Allowance mailed on Feb. 28, 2014 for U.S. Appl. No. 13/947,469, filed Jul. 22, 2013 in the name of California Institute of Technology.

PEN-SHAPED DEVICE FOR BIOLOGICAL SAMPLE PREPARATION AND ANALYSIS

CROSS REFERENCE TO RELATED APPLICATIONS

The present application claims priority to U.S. Provisional Patent Application No. 61/722,373, filed on Nov. 12, 2012, U.S. Provisional Patent Application No. 61/722,355, filed on Nov. 5, 2012, U.S. Provisional Patent Application No. 61/722,343, filed on Nov. 5, 2012, and U.S. Provisional Patent Application No. 61/722,326, filed on Nov. 5, 2012, is a continuation-in-part of U.S. patent application Ser. No. 13/407,644, filed on Feb. 28, 2012, and may be related to U.S. patent application Ser. No. 14/070,460 "DEVICES AND METHODS FOR BIOLOGICAL SAMPLE PREPARATION", U.S. patent application Ser. No. 14/070,466 "DEVICES AND METHODS FOR BIOLOGICAL SAMPLE-TO-ANSWER AND ANALYSIS", U.S. patent application Ser. No. 14/070,469 "METHODS OF FABRICATION OF CARTRIDGES FOR BIOLOGICAL ANALYSIS", U.S. patent application Ser. No. 14/070,454 "INSTRUMENTS FOR BIOLOGICAL SAMPLE PREPARATION DEVICES", U.S. patent application Ser. No. 14/070,440 "INSTRUMENTS FOR BIOLOGICAL SAMPLE-TO-ANSWER DEVICES", filed on even date herewith, the disclosure of all of which is incorporated herein by reference in their entirety.

TECHNICAL FIELD

The present disclosure relates to biomolecular analysis. More particularly, it relates to a pen-shaped device for biological sample preparation and analysis.

SUMMARY

In a first aspect of the disclosure, a device is described, the device comprising: a first structure, a second structure, a connecting structure connecting the first structure to the second structure, and a containment structure, wherein the containment structure substantially contains the first structure, the second structure, and the connecting structure, and wherein the first structure comprises a first plurality of containers, each container of the first plurality of containers having: a first opening, wherein the first opening has a sealing element which can slide inside the container while substantially maintaining a seal; a central part; a second opening; at least two ports in at least one container of the first plurality of containers, the at least two ports comprising: a first port configured for air venting; a second port configured for fluid insertion; a sealing cap for each port; the second structure comprises a second plurality of containers, each container of the second plurality of containers having: a first opening; a central part; a second opening, wherein the second opening has a sealing element; the connecting structure comprises at least one fluidics channel; a supporting element which can slide, rotate or move within a plane, thereby establishing a fluidics connection, through the at least one fluidics channel, between the second opening of at least one container of the first plurality of containers and the first opening of at least one container of the second plurality of containers, while substantially sealing other second openings of the first plurality of containers and other first openings of the second plurality of containers; the containment structure comprises a flat or dome-like top portion; a substantially cylindrical central portion, substantially containing the first structure, the second structure and the connecting structure; a substantially truncated conical bottom portion comprising at least one sample-drawing element, connected through a fluidic channel to at least one container of the second plurality of containers; a first plurality of buttons or switches in the central portion operatively connected to the sealing elements of the first and second structures, the buttons or switches being accessible on an external surface of the top or central portion; a second plurality of buttons or switches in the central or top portion operatively connected to the supporting element of the connecting structure, the buttons or switches being accessible on an external surface of the central or top portion; at least one button or switch in the bottom, central or top portion operatively connected to the at least one sample-drawing element, the button or switch being accessible on an external surface of the top, central, or bottom portion; wherein, upon operation of the at least one button or switch, the sample-drawing element draws a fluid sample from a desired biological fluid external to the device; and wherein, upon operation of the first or second plurality of buttons or switches, the fluid sample can be moved between the first or second plurality of containers in a desired sequence.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

The methods, devices and systems of the present disclosure relate to the preparation and analysis of biological samples. For example, a portable device in the present disclosure may be able to accept a biological sample, such as blood or other human bodily fluid, and prepare the sample for further processing, for example by extracting nucleic acid or other target analyte of interest. Another portable device may also contain one or more reaction chambers, where a specific reaction can take place after the sample has been prepared in the rest of the device. For example, the device may be able to prepare a biological sample and then perform polymerase chain reaction (PCR). A system in the present disclosure may be an automated instrument that can accept a portable device such as those described in the present disclosure. The system may be able to operate the portable device in an automatic rather than manual manner. The system may also comprise additional instruments that can analyze the sample, for example by optical techniques.

One example of procedures that can be executed through the devices and systems of the present disclosure is polymerase chain reaction.

Polymerase chain reaction (PCR) is a critical technique in the detection and amplification of nucleic acid products. However, before PCR can be performed, DNA must be liberated and purified from serological samples. While there are chemical kits that can be used to perform both lysis and nucleic acid purification, such methods require significant time-intensive, and highly-skilled technical labor to implement. The present disclosure describes several instruments and procedures that perform these tasks in a way that results in significant cost- and time-savings.

As known to the person skilled in the art, lysis comprises breaking down the cell walls or membranes, thereby causing the liberation of intracellular molecules.

PCR, and other techniques, are often only available through the use of expensive instruments or qualified operators. The systems and devices of the present disclosure can have the advantage of being portable and of being cheaper and easier to operate than more traditional realizations. These advantages can allow their use in less technological areas of the world, thereby enabling their use for disease detection, for example malaria detection.

The present disclosure also describes methods of operation of such devices and systems, as well as methods of fabrication for said devices.

Figure 1:
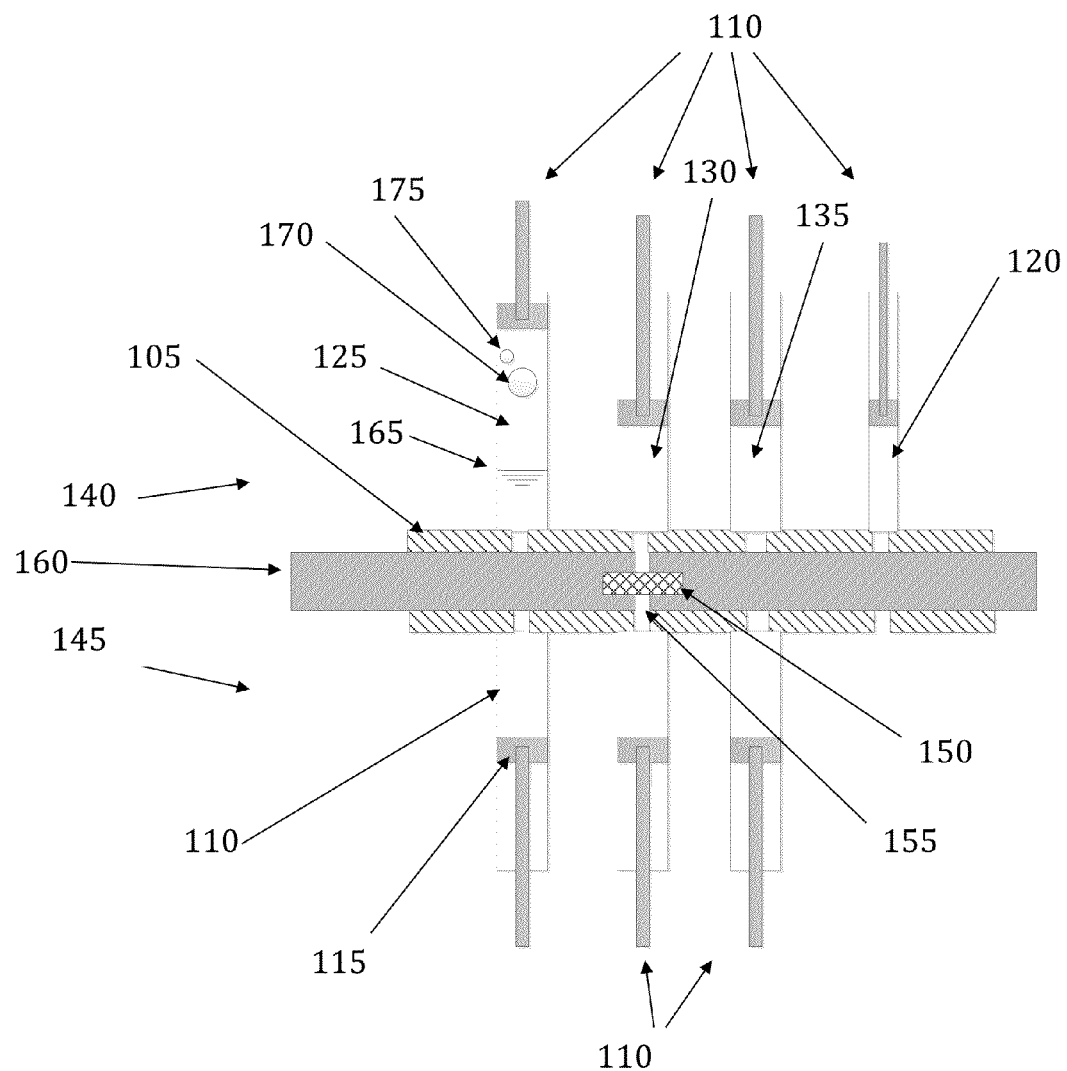
FIG. 1 depicts an exemplary sample preparation device.

FIG. 1 illustrates an embodiment of a fluidics device of the present disclosure for sample preparation. A housing (105) provides a supporting structure for the various components of the device. For example, housing (105) and other components may be fabricated with transparent acrylic materials or other kinds of plastic materials. A number of cylindrical structures, containers, container structures, reservoirs or cylinders (110) are affixed to the housing (105). The cylinders (110) may have plungers (115) or other similar sealing structures that permit the movement of fluids into and out of the cylinders (110). As the person skilled in the art will understand, plungers (115), or other similar structures, operate in a manner similar to a syringe. The diameter and size of the cylinders (110) may be different. For example, seven cylinders (110) are visible in FIG. 1, all of similar size, except elution cylinder (120) which in this example is smaller. As described previously (U.S. patent application Ser. No. 13/407,644, incorporated herein by reference in its entirety), each cylinder (110) may have a different function. For example, a sample may be inserted in a first cylinder (125), subsequently moved onto a lysing solution or buffer cylinder (130), then in a washing cylinder (135) and finally in an elution cylinder (120).

The cylinders (110) may contain different solutions as required by the technique being applied to the biological sample. For example, solutions may comprise a lysing solution, water or other solvents, elution buffers, and PCR-related solutions and solvents. A lysate solution may be moved from one cylinder to the next through the manual or automatic operation of the plungers (115). The top plungers (140) and the bottom plungers (145) may be operated in an appropriate sequence to push the liquid up or down the cylinders (110), passing through the sample container (150).

The sample container (150) may be, for example, a DNA binding matrix. The sample container (150) may be connected with cylinders (110) through openings (155) that allow the passage of fluids. The sample container (150) may be moved between the cylinders (110) by a horizontal sliding movement, manually or automatically operated, of a bar (160).

In some embodiments, the bar (160) may be flexible, while the openings (155) are rigid. The flexibility would allow the bar (160) to slide in the housing (105) while providing a waterproof seal at each opening (155). In other embodiments, the bar (160) may be rigid, while the openings (155) are flexible. For example, the openings (155) may have O-rings. Other combinations may be used.

Figure 2:
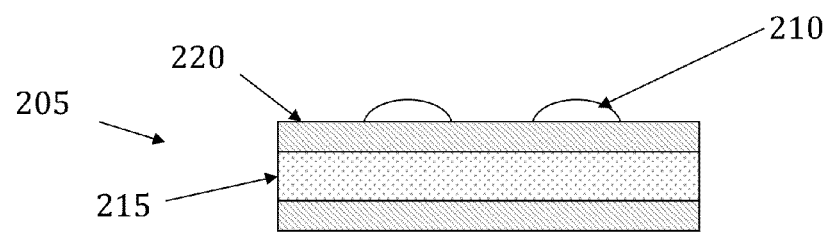
FIG. 2 illustrates an exemplary sample moving bar.

For example, FIG. 2 illustrates a crossectional view of a bar (205) with a sealing structure (210). The bar (205) may comprise, for example, an inner structure (215), such as an aluminum bar, coated with a sliding layer (220). For example, the sliding layer (220) may be Teflon tape.

Devices such as that of FIG. 1 may be used for sample preparation, in other words for preparing a sample for further processing. For example, a device may be used to extract or isolate DNA, proteins or other analytes, from a biological sample. The analyte may be extracted in a remote location, and analyzed at a later time in a laboratory.

Portable instruments may also be used, which accept the prepared sample and apply further processing, for example thermal cycling for qPCR. For example, a sample may be extracted and prepared with a device such as that of FIG. 1, and then inserted in a portable instrument which has a heater that can perform thermal cycling. As known to the person skilled in the art, thermal cycling can be employed for qPCR. The instrument may also have optical read-out capabilities. In some embodiments, the instrument may have a contact heater operated with a solenoid, a housing where the sample is inserted, light source and detectors, and any necessary waveguides to direct the light onto the sample. Multiple detectors may be used, for example each detector able to sense a specific wavelength. The instrument may also comprise necessary electronic components for its control and operation. The solenoid may be a bistable solenoid: an electric pulse may activate the solenoid, in turn moving the heater in contact with the sample cartridge. Another pulse may activate the solenoid again, thereby moving the contact heater away from the sample cartridge.

In some embodiments of the disclosure, devices are used for sample preparation. In other embodiments, such devices are coupled to an instrument which accepts a sample from the device and performs further processing such as thermal cycling and optical analysis. In yet other embodiments, devices may perform sample preparation and additionally possess a reaction chamber for specific techniques, for example qPCR. In other embodiments, such devices with a reaction chamber may also be coupled to an instrument which accepts the sample and performs additional processing such as thermal cycling and optical analysis. For example, an instrument may accept the PCR chamber of a PCR device and perform thermal cycling and cooling of the sample inside the PCR chamber, and additionally optical analysis. The instruments of the present disclosure are configured to accept the sample cartridges or reaction chambers of the corresponding devices. For example, a sample preparation device may include a detachable qPCR reaction chamber, which can then be inserted into an instrument. Alternatively, a sample preparation device may be inserted wholly into an instrument.

The devices for sample preparation, such as that in FIG. 1, may have plungers or similar operational controls which are manually activated. Such plungers or similar controls may be operated automatically by an instrument once the device is inserted into the instrument. The instrument may then have automatic means to push the plungers, for example. In some embodiments, the instrument may have pistons which are automatically controlled to push on the plungers of sample preparation devices.

Devices and instruments which combine sample preparation and a technique such as qPCR may be termed as sample-to-answer devices and instruments. Alternatively, the sample preparation step, and the qPCR step may be done separately. In that case, instruments and devices may be specific to sample preparation. Other instruments and devices may be specific to qPCR. In other words, devices and instruments may be 'sample preparation' devices and instruments, 'qPCR' devices and instruments, or 'sample-to-answer' devices and instruments, when both 'sample preparation' and 'qPCR' are performed. Other techniques may substitute qPCR, if such techniques can be effectively applied in the reaction chambers as described in the present disclosure.

Referring again to FIG. 1, cylinders 110 may have additional openings to facilitate their operation. For example, cylinder (125) illustrates a possible level for a liquid (165) introduced in the cylinder (125). Above liquid level (165), openings (170) and (175) may be present. Opening (175) may be a vent hole, through which air can escape when a liquid is introduced. Opening (170) may be a sample injection hole or port, through which a sample can be introduced. A syringe or other device may be used to introduce the sample. For example, a pipette or a capillary may be used. For example, finger pricks with attached capillary and hand-operated bulb exist which let an operator draw blood and push it out of the capillary.

Opening (170) and (175) may be self-sealing, or have rubber caps or similar ways of closing. For example, opening (170) may be a self-healing or self-sealing injection port (septa).

In some embodiments, the injection port (170) may have an integrated, or removable, adapter to allow the insertion of a pipette tip. In other embodiments a capillary may be preattached to the injection port, for easier operation.

Figure 3:
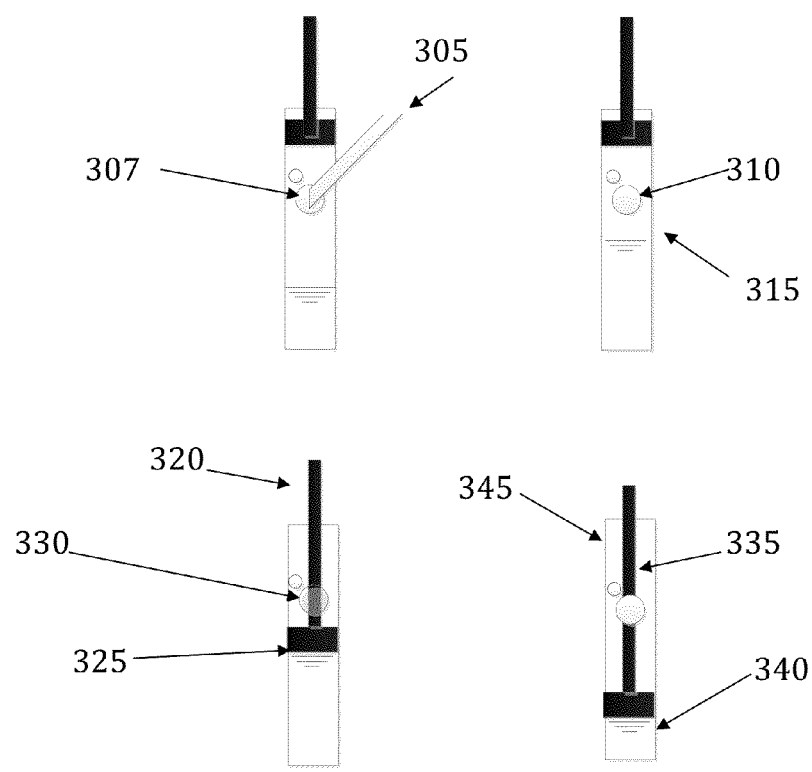
FIG. 3 illustrates some examples of injection ports and their operation.

FIG. 3 illustrates some examples of injection ports and their operation.

In FIG. 3, a capillary (305) may be attached to injection port (307). A liquid solution may be present at a level (315)

below injection port (310). Plunger (320) may be operated to contact liquid level (325) below injection port (330). In this way, the liquid cannot flow out of the injection port (330) and operation of the device can continue. For example, plunger (335) may be pushed to move the liquid (340) out of the cylinder (345).

Figure 4:
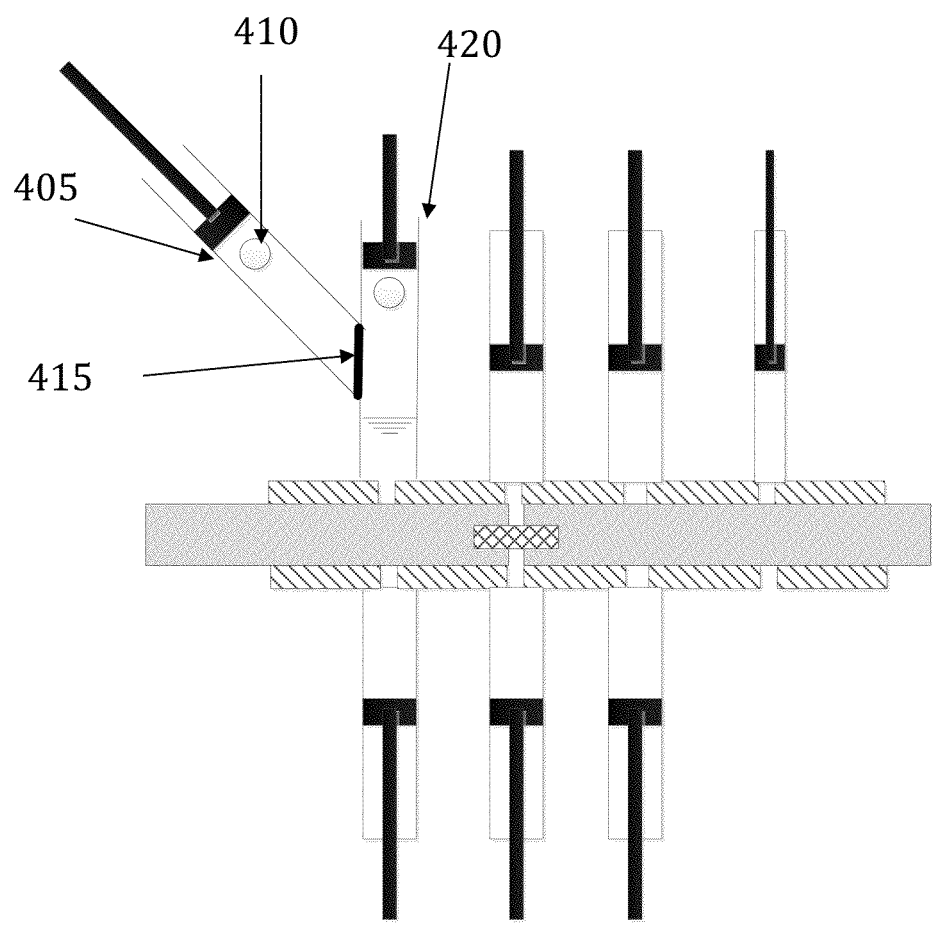
FIG. 4 illustrates an exemplary sample preparation device with an additional inlet cylinder on the side.

FIG. 4 illustrates an exemplary sample preparation device with an additional inlet cylinder on the side. In some embodiments, cylinder (420) has an additional cylinder (405) on a side. Cylinder (405) may also have a sample injection port (410). Additionally, a filter (415) may be present. For example, a blood sample may be introduced in cylinder (405), and blood cells may be filtered at filter (415), thereby introducing plasma in cylinder (420). The plasma may then be processed by a sample preparation device or a sample-to-answer device, for example to test for malaria. While filters exist which can be attached to a syringe, they present a few disadvantages: for example, they may have a small surface area and become easily clogged. An advantage of having a filter built-in into the device, such as filter (415), is that it can be fabricated with a large surface area, thereby allowing fast filtering of a biological sample.

Figure 5:
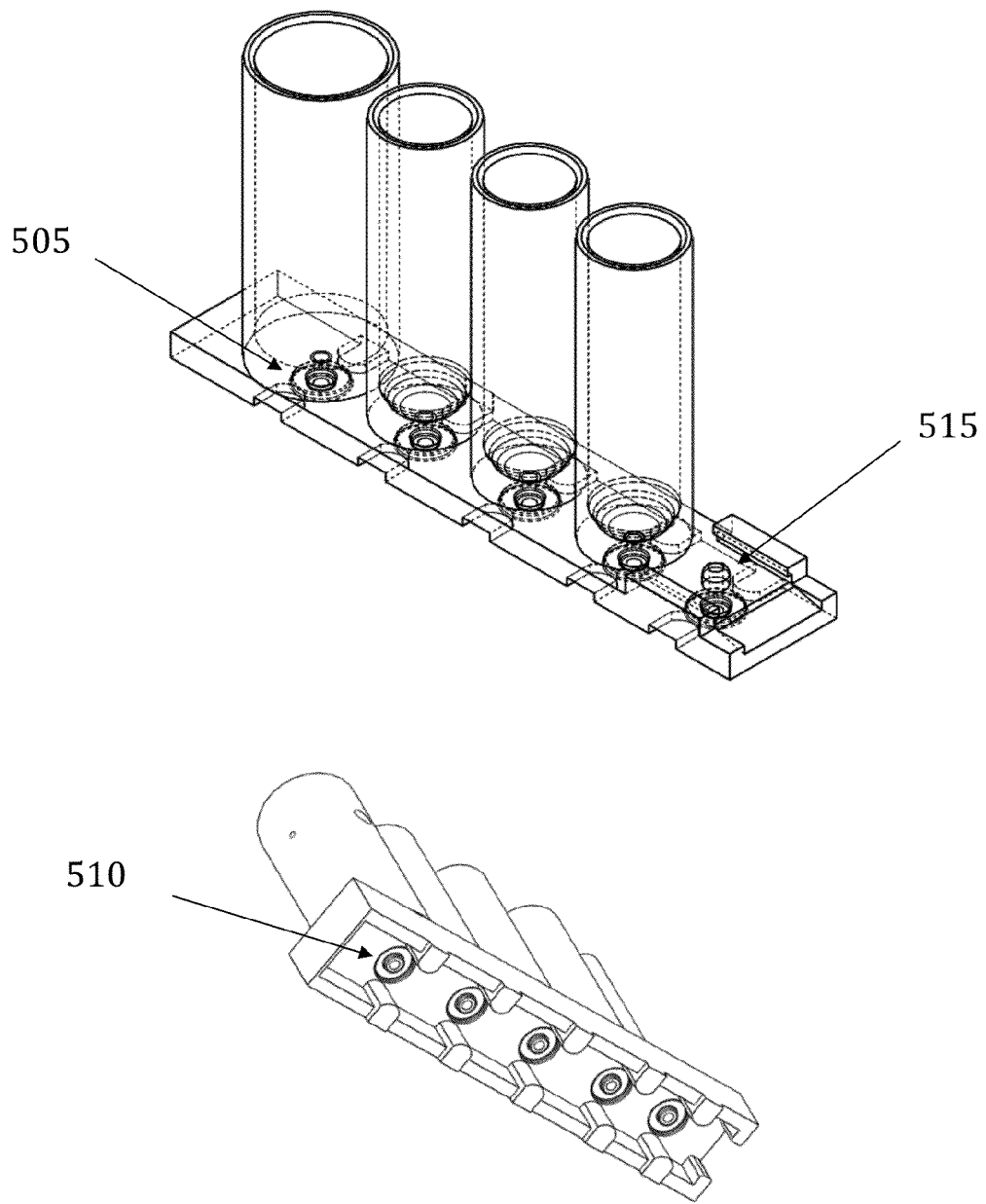
FIG. 5 shows the upper half of an exemplary device.

FIG. 5 shows the upper half of an exemplary device. Circular recesses (505) may be present where O-rings can be inserted to provide a seal when the sample container is moved between cylinders. A plug-in connector (515) may be present where, for example, a custom cylinder may be inserted for specific applications. Alternatively, a capillary may be connected to connector (515) to move the liquid sample to another device or instrument for further processing. For example, a capillary configured to be used for optical detection may be attached to connector (515). In this way, optical detection can be applied to the sample in the capillary, after processing in a sample preparation device or a sample-to-answer device. In FIG. 5, a bottom view of the device also illustrates circular recesses (510).

Figure 6:
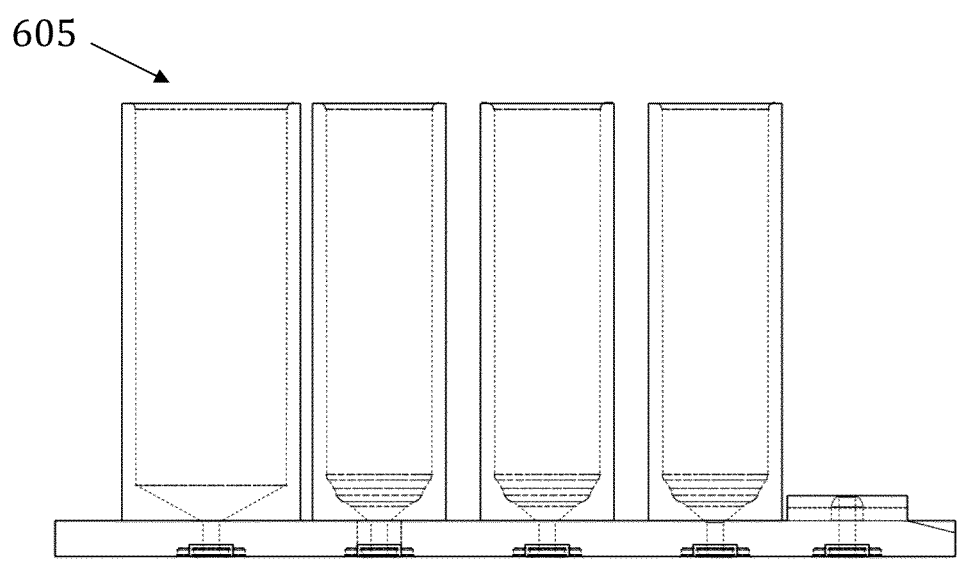
FIG. 6 illustrates an exemplary side view of a sample preparation device.

FIG. 6 illustrates an exemplary side view of a sample preparation device. Although the cylinders (605) in FIG. 6 are placed in a line, other arrangements may be possible. For example, a circular arrangement.

Figure 7:
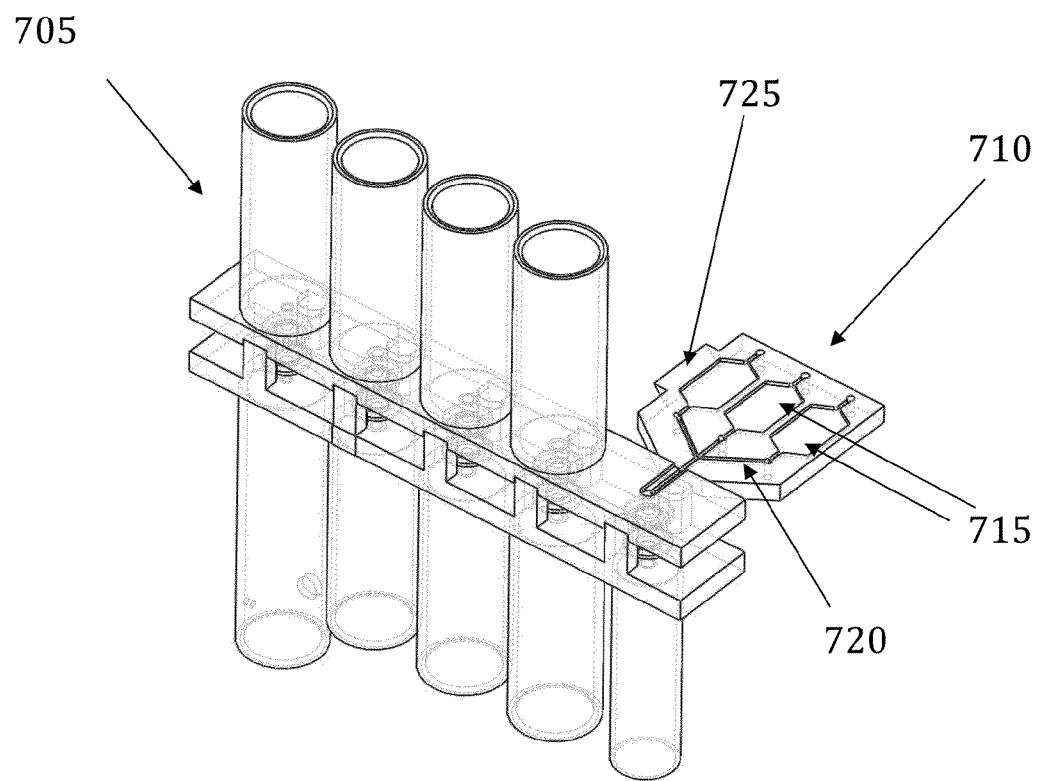
FIG. 7 illustrates an exemplary sample-to-answer device.

FIG. 7 illustrates an exemplary sample-to-answer device, where a sample preparation device (705), comprising several cylinders, is attached to a reaction cartridge (710). Cartridge (710) may comprise, for example, a qPCR chamber, and it may be permanently attached to device (705), or may be removable. In the example of FIG. 7, the reaction cartridge (710) comprises three separate compartments or reaction chambers (715), connected by microfluidics channels (720). A prism (725) may be part of the cartridge (710), to guide light onto the reaction chambers (715). The prism may be made of the same material of cartridge (710) and sample preparation device (705), such as acrylic, PVC or other plastic materials.

Figure 8:
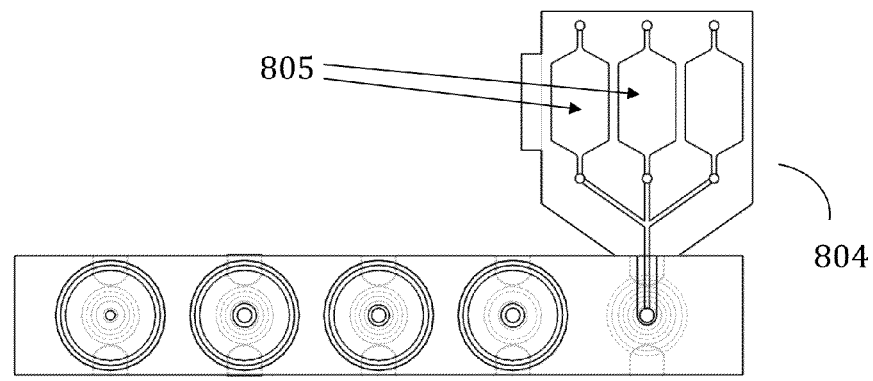
FIG. 8 illustrates a top view of a sample-to-answer device.

FIG. 8 illustrates a top view of a sample-to-answer device, with a reaction cartridge (804) with three compartments (805).

Figure 9:
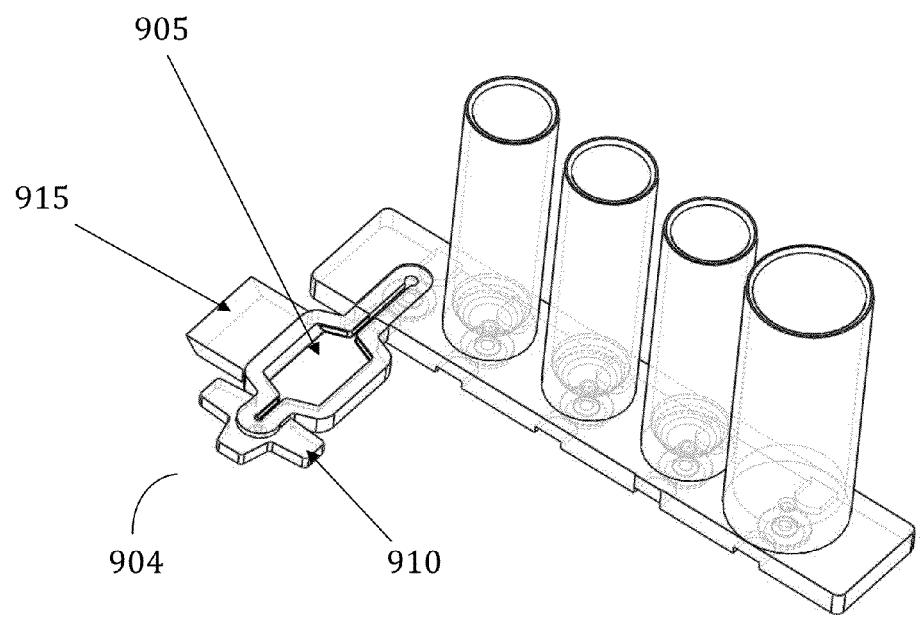
FIG. 9 illustrates an exemplary sample-to-answer device.

FIG. 9 illustrates an exemplary sample-to-answer device. The reaction cartridge (904) comprises, in this example, one reaction compartment (905). A prism (915) to guide light is part of the reaction chamber (905). Handles (910) are also part of the chamber (905), to facilitate handling. The reaction cartridge (904), prism (915) and handles (910) may all be fabricated from the same material.

The cartridges of the present disclosure, such as cartridge (904) of FIG. 9, may have a metallic back plate attached to the acrylic, PVC, or plastic material from which the rest of the cartridge is fabricated. For example, the metallic back plate may be made of aluminum. One purpose of such metallic plate is to increase thermal exchange between the solution inside a reaction chamber and an outside heater or cooler. It is known to the person skilled in the art that in some reactions, for example PCR, thermal cycling may be required. In such cases, it may be advantageous to have a material with increased thermal conductivity relative to plastic. Aluminum is safe to use with PCR and is cheaper than noble metals, therefore it may be a good choice. Other metals may also be used, comprising noble metals. It is also known to the person skilled in the art that in certain situations it may be advantageous to freeze-dry samples for later processing. It may also be advantageous to freeze-dry the content of a cartridge, for example a cartridge containing solvents or reactive solutions which are meant to be part of a preparation or analysis technique. For example, a solution with binding molecules may be placed inside a reaction chamber and freeze-dried for later use. In such cases, the use of a metallic back plate may be advantageous because of its enhanced thermal conductivity.

A metallic back plate may be bonded to a reaction cartridge by, for example, the use of adhesives. One method comprises using a robot to reliably apply dots of adhesives at bonding sites of the reaction chamber and/or the metallic back plate. The two sides can then be pressed together with a constant and uniform pressure. The use of automated means of assembly, such as through a robot, allows a high degree of repeatability and control. Alternatively, instead of applying one dot of adhesive at a time, a mask perforated in an appropriate pattern may be used, and adhesive or other bonding agent may be sprayed or squeezed through the perforated mask, thereby printing adhesive dots, or an adhesive continuous line, along a desired pattern. Again, the two sides to be bonded can then be pressed together at an appropriate pressure. Such means of bonding enable an automated fabrication, suitable for lowering the price of each device and increase its deployment in areas where low cost is necessary for their establishment.

In several embodiments, the metallic plate is attached to the edges of the bottom part of the plastic cartridge, therefore the metal is in direct contact with the solution inside the chamber. The adhesive is placed on the edges of the device. The adhesive may be cured as necessary, without damaging the devices. Due to the different thermal expansion coefficients of the metal and of the polymer materials (such as PVC) used to fabricate the cartridge, it may be advantageous to reduce the contact area between the metal and the plastic components of the cartridge, in order to avoid any possible cracking of the cartridge.

Another advantage of a metal bottom plate is that it can have an increased optical reflectivity, thereby increasing fluorescence and guide light in a more efficient way, for application in optical detection techniques.

Although several examples of the present disclosure refer to PCR and PCR reaction cartridges and chambers, the person skilled in the art will understand that different techniques may be related to the devices of the present disclosure. For example, a solution with enzymes for PCR may be used in said devices, or lysing may be applied. Freeze-drying or lyophilization may be employed to store solutions or samples at room temperature, as their shelf life can be greatly increased once in dried form.

Lyophilization can be carried out on the cartridge before or after bonding the metal and polymer parts. The metal part can help in fast lyophilization due to its thermal conductivity and large surface area.

After lyophilization of the reagents in either the metallic or polymeric parts (or both) of the cartridge, room temperature bonding can be used to cure the adhesive which bonds the metallic part of the cartridge to the polymeric part of the cartridge.

Appropriate fabrication techniques can be used to protect the lyophilized reagents while bonding.

Figure 10:
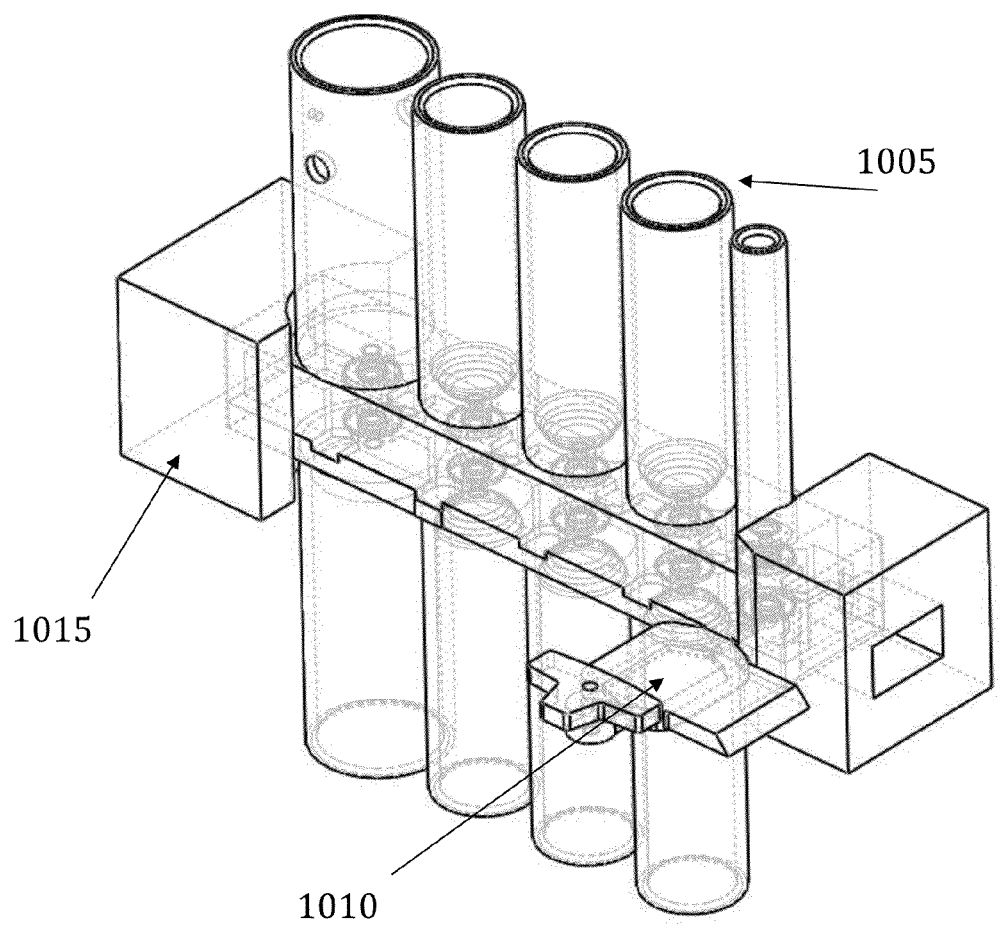
FIG. 10 illustrates an exemplary sample-to-answer device.

FIG. 10 illustrates an exemplary sample-to-answer device. A sample preparation set of cylinders is visible (1005), as well as a reaction cartridge (1010). Adapters (1015) may be present on both sides of the device, to allow plugging into an instrument for automatic operation of plungers, sample movement, thermal cycling and optical detection.

In several embodiments of the present disclosure, reaction cartridges are described, which comprise reaction chambers. The reagents necessary for the desired technique to be performed can be prefilled in the reaction chamber in various forms. The reagents may be coated onto the walls of the chamber or capillary, either covering the entire surface, or specific parts of the available surface.

Some reagents, such as qPCR reagents, may be lyophilized and coated on the metal backplate. During operation of a device, the lyophilized reagents may be reactivated by the appropriate solvent, e.g. water. For example, when the elution solution, containing the DNA of interest as prepared by the operation of the sample preparation device, fills a reaction cartridge, the reagents are re-suspended and the reaction can take place.

Reagents can also be lyophilized on the polymer side of the reaction chamber instead of on the metal side. Reagents can also be spotted on surfaces depending on the application. Some applications are described as following.

ELISA (enzyme-linked immunosorbent assay) is a technique that can be used with the devices of the present disclosure. In one embodiment, the antibodies with enzymes are immobilized on a surface of a reaction chamber (on the metal or polymer side). The sample (for example whole blood) can be flowed through the cartridge, or be given some time so that hybridization between the target analyte and the antibodies can occur. A wash buffer can be used to flush out the sample and the cartridge can be used to detect the result. For example, the analyte bound to the surface can be detected after the rest of the liquid sample is flushed out.

For some samples, there is no need to flush the sample if, for example, optical detection can be carried out even in the presence of the remaining liquid sample. Alternatively to optical detection, electrochemical detection can be used using patterned electrodes on a surface of the chamber, either the metal or polymer (plastic) surface. To reduce the reaction time, the surface area can be increased by structuring the surface, for example with nanopillars, fractal shapes and other surface treatments which can increase the interaction area. A plastic surface can be patterned via injection molding or other techniques. Increasing the interaction area can reduce the time for hybridization. The fluid can also be made to flow multiple times through the reaction chamber to increase the chance that the relevant molecules will attach to the binding sites. Flowing the fluid sample through the reaction chamber multiple times can reduce the total reaction time.

The cartridges of the present disclosure can also be used, for example, for immunoPCR to detect antigens. The patterning of reagents can be done similarly as to what described above. The capture agents (e.g. antibodies, aptamers) can be immobilized on the surfaces of the reaction chamber. In other embodiments, the binding of capture agents and targets takes place outside of the cartridge and the PCR-ready solution is introduced into the cartridge. This technique can be used to preserve time-sensitive analyte information at the point of care. Thus, the analytes can be converted to amplicons via binding reactions. Since amplicons are often more stable than many analytes (like proteins, etc.), the PCR can be done later or at a different location. As known to the person skilled in the art, the PCR has the ability to amplify the original information and thus detect very low levels of analytes. qPCR can be used to quantify the amplicons as well.

The reaction chambers of the present disclosure can also be used as hybridization chambers to allow detection via different techniques, such as optical, electrochemical or others. For example, capillary electrophoresis is a viable detection technique. As known to the person skilled in the art, a capillary can be attached to a reaction chamber and electrophoresis is activated through a voltage difference. The target analyte, such as DNA, will then move through the capillary as a function of its size, thus allowing detection. For example, a negative voltage can be applied to the metal base of the cartridge to repel the amplified DNA, which will then flow through an attached capillary. The cartridge can thus integrate easily with capillary electrophoresis detection without the need to fabricate additional electrodes. As discussed previously, the reagents can be immobilized on a surface of the cartridge.

For the case of electrical detection, the metal surface or a part of it (with or without modification) can aid in electrical detection due to its high metallic conductivity. For example, electrodes may be patterned on the surface to employ cyclic voltammetry.

Among the possible applications of the devices and instruments of the present disclosure, the cartridges can be used to detect multiple DNA targets as required in forensics and human identification.

During operation, when a sample, such as DNA, is introduced in a reaction chamber, the metal backplate can help attract more DNA into the chamber. For example, an elute container attached to a reaction chamber may contain more liquid whose volume is larger than what can be contained the reaction chamber. To attract more DNA into the cartridge, a voltage can be applied to the metal backplate of the cartridge. The DNA will then be attracted by the voltage difference between the chamber and the elute container, flowing through the elution liquid.

The above technique, using voltage to attract DNA, can also be used to enhance hybridization and reaction speed for various techniques which use patterning on the metal surface. Changing the voltage on the surface can also help in mixing (e.g. pulling and pushing DNA) and capture/de-capture operations.

The reaction cartridge can also be used for complex biological samples like whole blood, for different uses such as pathogen detection. Heme-resistant enzymes can amplify the target in samples with whole blood in it. Such enzymes can be utilized with the sample preparation and sample-to-answer devices of the present disclosure. For clean samples, like spinal fluid (e.g. for meningitis tests) the sample can be directly used and thus the reaction cartridge with lyophilized reagents can work on its own without sample preparation.

The cartridges of the present disclosure can also be used for solid phase PCR, possibly allowing significant multiplexing capabilities in one cartridge.

If the regents are coated on the polymer side, then evanescent waves can be used to detect fluorescence, as the fluorophores are now very close to the surface and they can be excited by TIR-based (totally internal reflection) waves. In order to limit noise and capture only the fluorescence signal by evanescent waves, the reaction chamber can be dried so that the electromagnetic rays that would be moving in the fluid have minimal effect on the fluorescence. In other words, the fluorescence detection can be carried out with the fluid still in the chamber, in which case the signal detected will also comprise the fluorescence originating from the fluid. If, however, the chamber is emptied as well as possible, then little fluid will remain and the fluorescence signal will originate primarily from the target analyte bound to the fluorophores coated on the walls of the chamber.

In other embodiments, the optical excitation angles of the light source and its collimation can be adjusted so that the evanescent wave fluorescence can be observed even for reaction cartridge filled with fluid.

The metal back plate of the cartridges can also be used for evanescent wave detection. For example a very thin $SiO_2$ (glass) coating can be applied on the cartridge. The excitation light can then be guided within the coating. In other words, the fluorophores and the evanescent light detection can occur both on surfaces on the polymer surfaces of the chamber, or on the metal surface of the chamber. Alternatively, both the polymeric and metallic surfaces could be coated with fluorophores or other binding reagents, at the same time.

Figure 11:
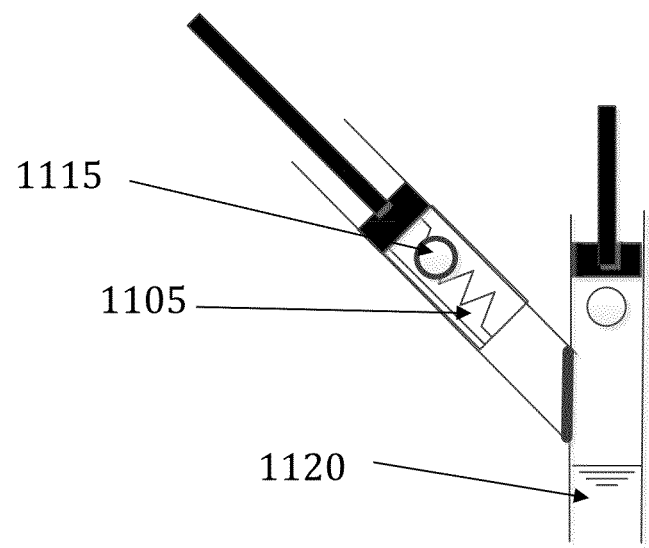
FIG. 11 illustrates a side entry port component.
Figure 11:
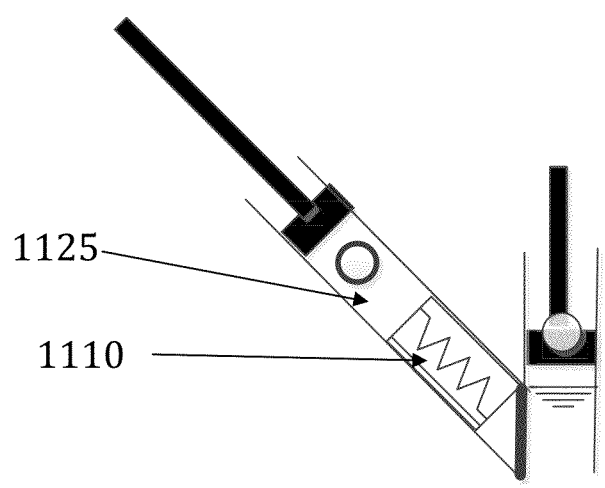

When introducing samples in a device, their consistency may determine the best way of their introduction. For example, some samples may be denser than others, some liquid samples may be very viscous. To facilitate their introduction, as well as their mixing with any solution present inside a device, certain components may be added to a device. For example, FIG. 11 illustrates a side entry port, similar to that depicted in FIG. 4. Referring to FIG. 11, a screw or mixer or screw pump element is visible (1105), whose purpose is to push the liquid forward. Element (1105) may also facilitate the mixing of a sample introduced through the port (1115), with the liquid already present in the device (1120). Element (1115) may be configured to move through cylinder (1120) when a liquid is introduced, up to an extended position (1110). As it is known to the person skilled in the art, a similar technique is used in the field of injection molding.

Figure 12:
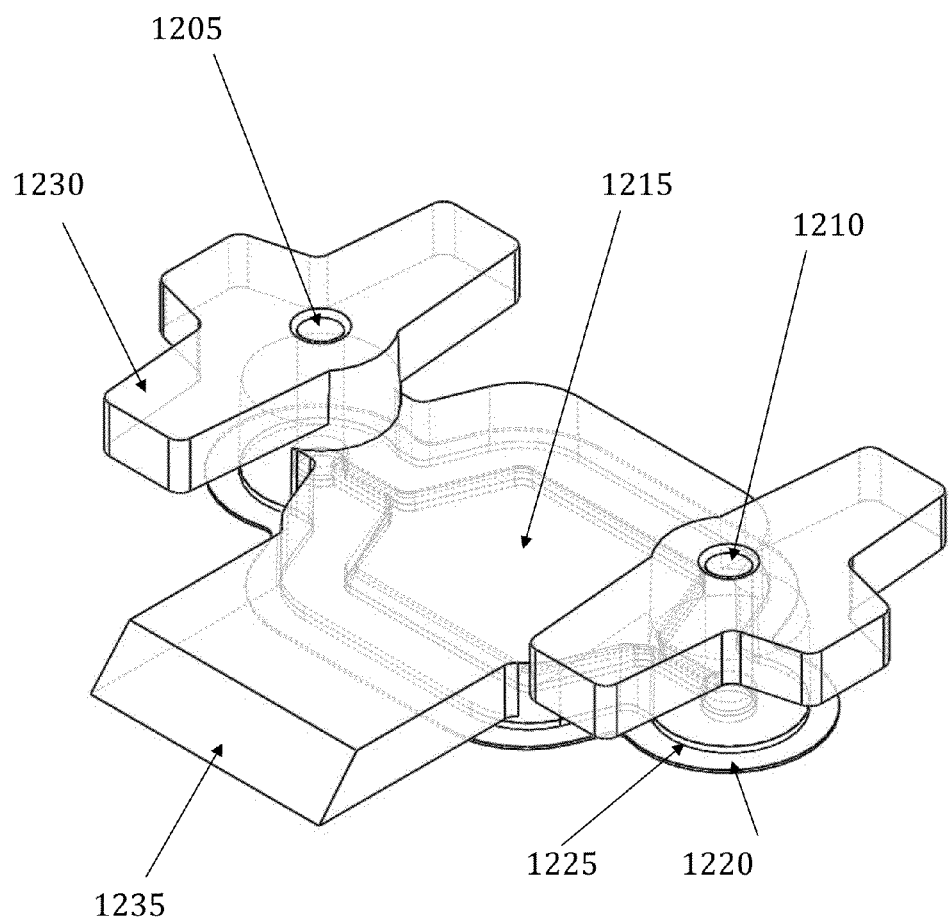
FIG. 12 illustrates an exemplary cartridge with a reaction chamber.

FIG. 12 illustrates an exemplary cartridge with a reaction chamber. Such cartridge may be fabricated with a polymer, such as PVC, or other plastic materials, and may comprise a metal backplate.

The cartridge of FIG. 12 comprises an inlet port (1205) and an outlet port (1210) or vent. For example, as the sample is introduced through port (1205), air is displaced through vent (1210). The solution present in the reaction chamber (1215) can also be removed through port (1210). As discussed above, the cartridge comprises a metal backplate (1220), bonded to the polymer side through an adhesive (1225). The cartridge may also comprise handles (1230). The cartridge may also comprise a prism (1235) to focus and distribute light onto the reaction chamber (1215) when an optical detection technique is carried out. Inlet port (1205) may also be attached directly to a sample preparation device. For example, FIG. 10 displays an exemplary cartridge (1010) attached to a sample preparation device (1015) thereby forming a sample-to-answer device.

Figure 13:
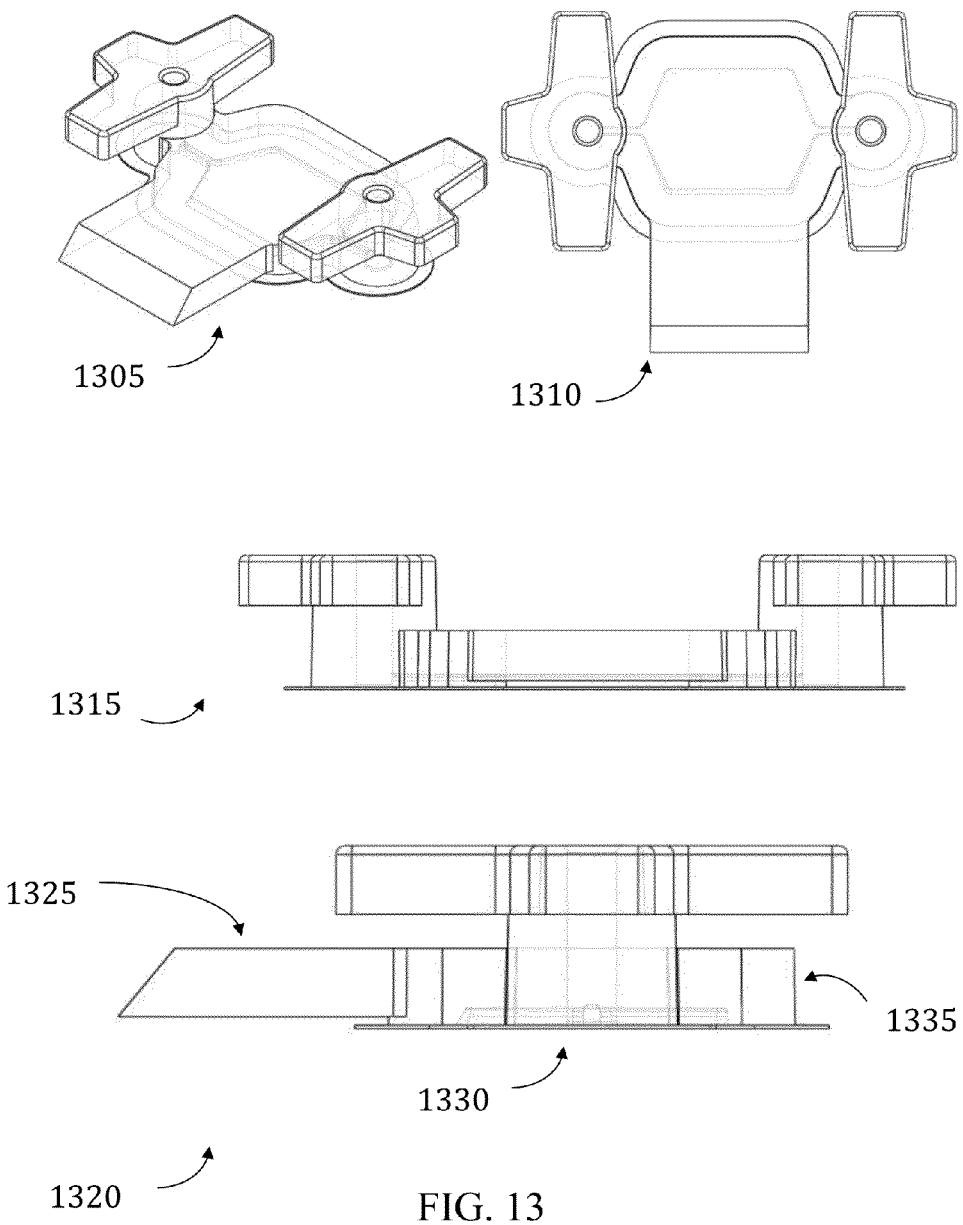
FIG. 13 illustrates several views of an exemplary cartridge.

FIG. 13 illustrates several views of an exemplary cartridge. A perspective view (1305), a top view (1310), a front view (1315) and a side view (1320). As visible in the side view (1320), a metal back plate (1330) is bonded to the polymeric part (1335) of the cartridge. The prism (1335) can be spaced away from the back plate (1330) in order to decrease the total surface bonding area between the metal element (1330) and the rest of the cartridge. By having a reduced surface area, less stress is potentially applied to the cartridge, for example during a change of temperature due to different expansion coefficients. In other embodiments, a cartridge may comprise more than one prism, in order to accept optical inputs from multiple light sources. In some embodiments, the metal back plate (1330) may be coated with various substances such as glass, parylene, polyimide, silicone etc. via spray coating, thermal evaporation, sputtering, physical vapor deposition and many other processes. As understood by the person skilled in the art, silicone coatings can be applied to needle syringes as well. The purpose of such coatings is to increase biocompatibility of the metal surfaces, as some metals are toxic to the enzymes used as reagents in several techniques such as qPCR.

In some embodiments, reflective aluminum (for example manufactured by Anomet) can be used for the metal back plate of a cartridge, as it is PCR compatible. Such reflective aluminum can be coated via vacuum processes and has low cost and good optical properties.

The polymer part of a cartridge can be molded into light-guiding structures such as lenses, concentrators etc. If the cartridge is made of COC (cyclic olefin copolymer) or COP (cyclic olefin polymer) then the optical properties of these materials can be used advantageously as required by optical techniques.

A very thin metal foil can be used as a metal base for a cartridge, for example similar to aluminum foil as used in food packaging. Such foil could be used, for example, to increase optical reflectivity. For mechanical support, the foil could be applied to a back plate, such as a polymeric back plate, or a metallic back plate of a different metal. The sheet metals used in cans, such as those for beverages, can also be used as a metal base for a cartridge. Such sheet metals can have a polymer coating on the inner surface.

Figure 14:
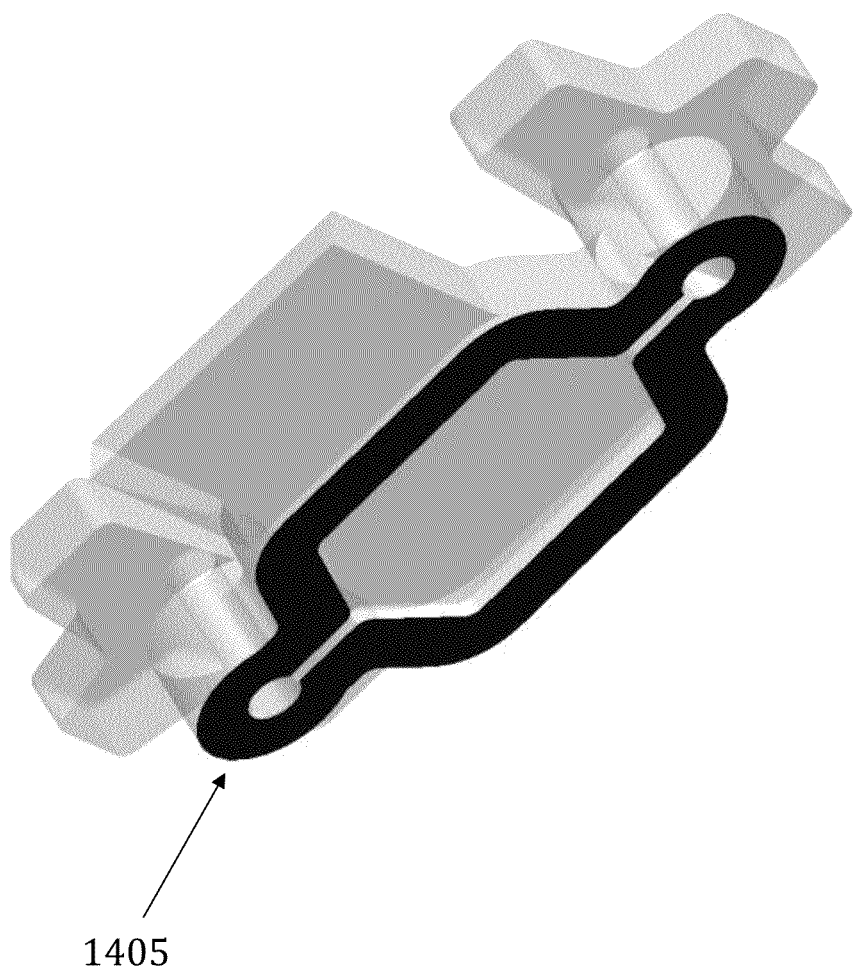
FIG. 14 illustrates a bottom view of an exemplary cartridge.

FIG. 14 illustrates a bottom view of an exemplary cartridge with an exemplary shaded area (1405) which illustrates as a bonding area between a polymer cartridge and a metal back plate.

Figure 15:
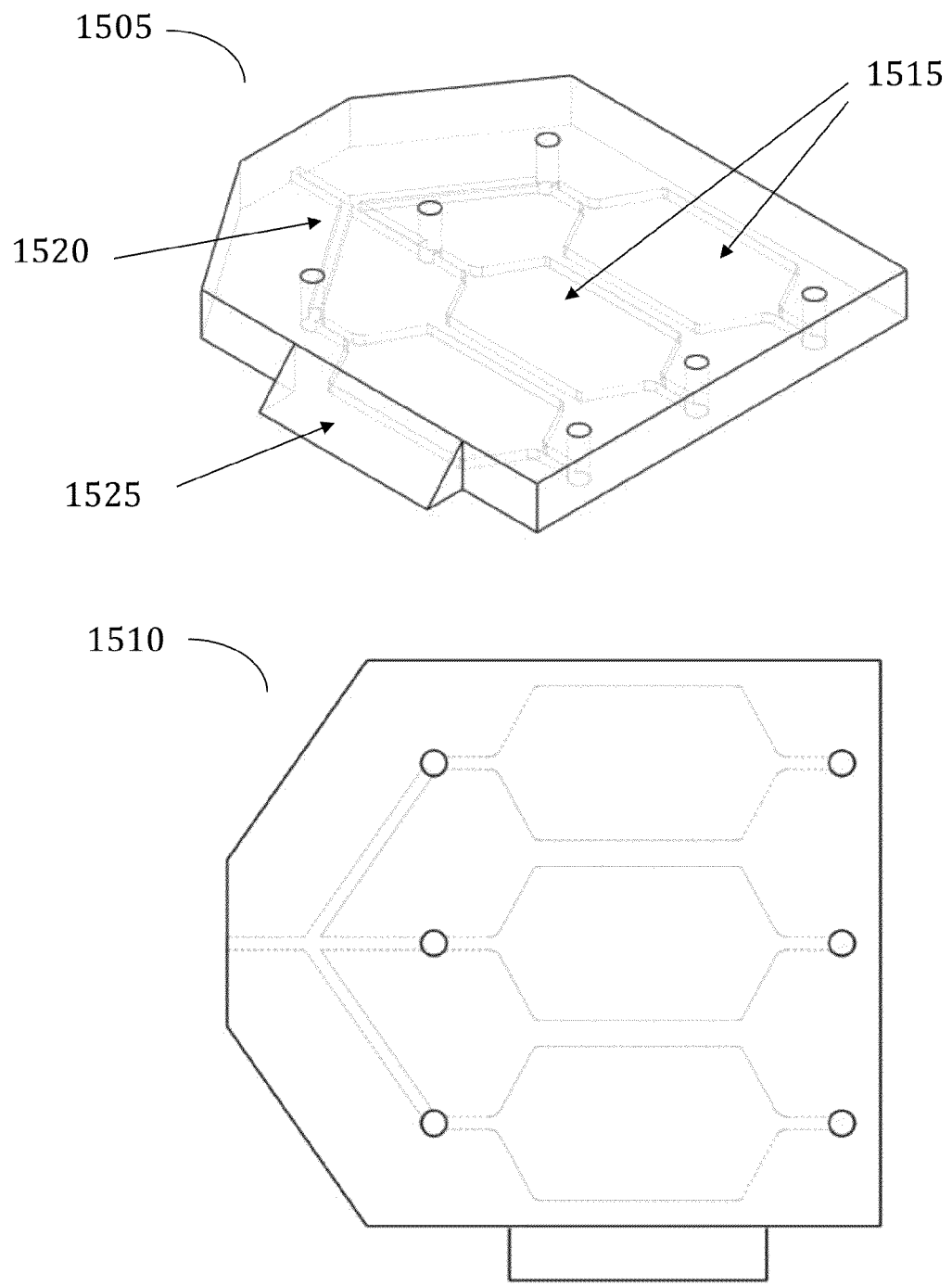
FIG. 15 illustrates an exemplary cartridge with three reaction chambers.

FIG. 15 illustrates an exemplary cartridge with several reaction chambers, both in perspective view (1505) and top view (1510). The cartridge may comprise, for example, three reaction chambers (1515) connected by microfluidics channels (1520), and an optical prism (1525). Prism (1525) may be configured to distribute, guide and/or focus light over all of the three chambers (1515) simultaneously, for optical detection applications. By carefully controlling the amount of fluid introduced in a cartridge, it is possible to only fill the three chambers (1515) while leaving the connecting channels (1520) empty, or filled with air. In this way, the three chambers (1515) remain separated and their content will not mix. A different reaction can therefore be applied in each of the three chambers (1515), if desired. Such separation with air can be achieved in different embodiments of the cartridges of the disclosure, by using a similar principle of operation, as can be understood by the person skilled in the art.

Figure 16:
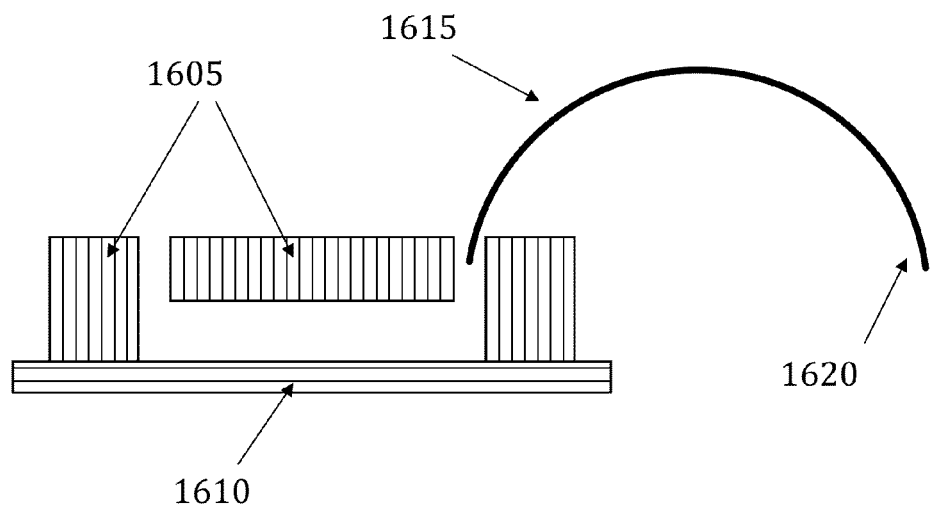
FIG. 16 illustrates an exemplary cartridge with a capillary, in cross sectional view.

FIG. 16 illustrates an exemplary cartridge with a capillary, in cross sectional view. The cartridge comprises a polymer part (1605) and a metal back plate (1610). The outlet is linked to a capillary (1615). The capillary's function has been described above in the present disclosure, and comprises, for example, flowing the liquid sample from a cartridge to another container, or even performing detection techniques through the capillary, such as capillary electrophoresis. For example, a positive voltage may be applied at the capillary (1620), and a negative voltage may be applied to the metal plate (1610). For example, DNA may be attracted by the voltage difference, flowing in the capillary (1615) with different speed depending on the size of the DNA. Thus, for example, different DNA parts may be spaced along the capillary (1615) through the voltage difference.

Figure 17:
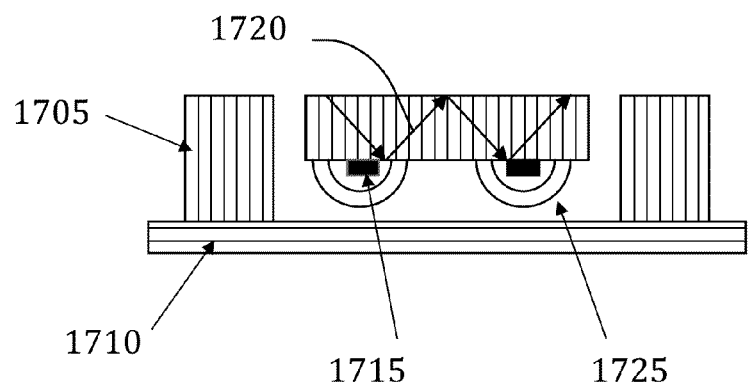
FIG. 17 illustrates an example of a cartridge with reagents for optical detection.

FIG. 17 illustrates an example of a cartridge with reagents for optical detection. The cartridge comprises a polymer body (1705) and a metal plate (1710). Reagents (1715) may be attached to the walls of the cartridge, and light (1720) may be guided through total internal reflection, for example originating from a light source and guided through a prism, such as prism (1235) of FIG. 12. Referring again to FIG. 17, an evanescent field (1725) will be present due to the light rays (1720), as understood by the person skilled in the art. The reagents (1715) will bind, or not, with the target analyte present, or not, in a liquid sample. The presence or absence of the target analyte at the reagent sites (1715) can be detected, through the evanescent field (1725) of light rays (1720). In some embodiments, a voltage may also be applied at plate (1710), for example to attract the target analyte inside the reaction chamber through an inlet port.

Figure 18:
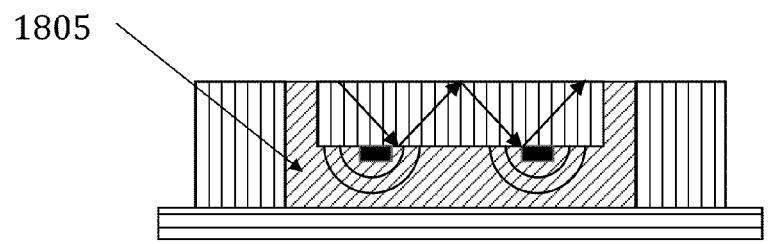
FIG. 18 illustrates the exemplary cartridge of FIG. 17, with fluid present in the reaction chamber.

FIG. 18 illustrates the exemplary cartridge of FIG. 17, with fluid (1805) present in the reaction chamber.

Figure 19:
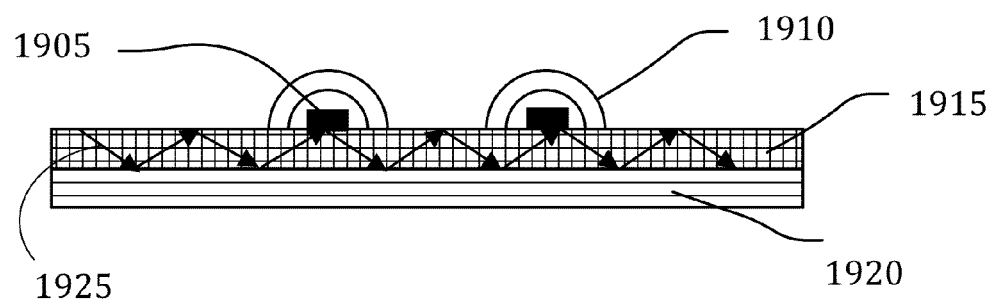
FIG. 19 illustrates another embodiment of detection based on total internal reflection.

FIG. 19 illustrates another embodiment of detection based on total internal reflection, with reagent sites (1905) and evanescent waves (1910), where the reagent sites (1905) are placed on the bottom of a cartridge, on the metal plate (1920) side. In some embodiments, the metal plate (1920) may be coated with a transparent coating (1915) acting as a waveguide to allow the total internal reflection of light (1925).

Figure 20:
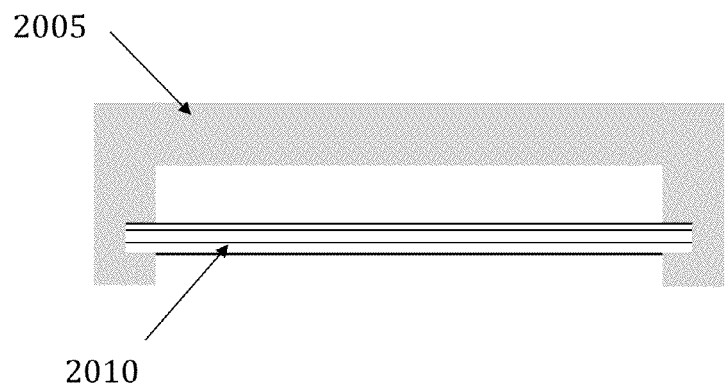
FIG. 20 illustrates an exemplary cartridge with a fitted metal plate connection.

FIG. 20 illustrates an exemplary cartridge with a fitted metal plate connection. In this embodiment, a cartridge comprises a polymer side (2005) and a metal plate (2010), where the polymer side (2005) is fabricated so as to have a snap-on shape which fits the metal plate (2010). In such a way, less adhesive or even no adhesive may be necessary to bond the polymer side (2005) with the metal side (2010).

Figure 21:
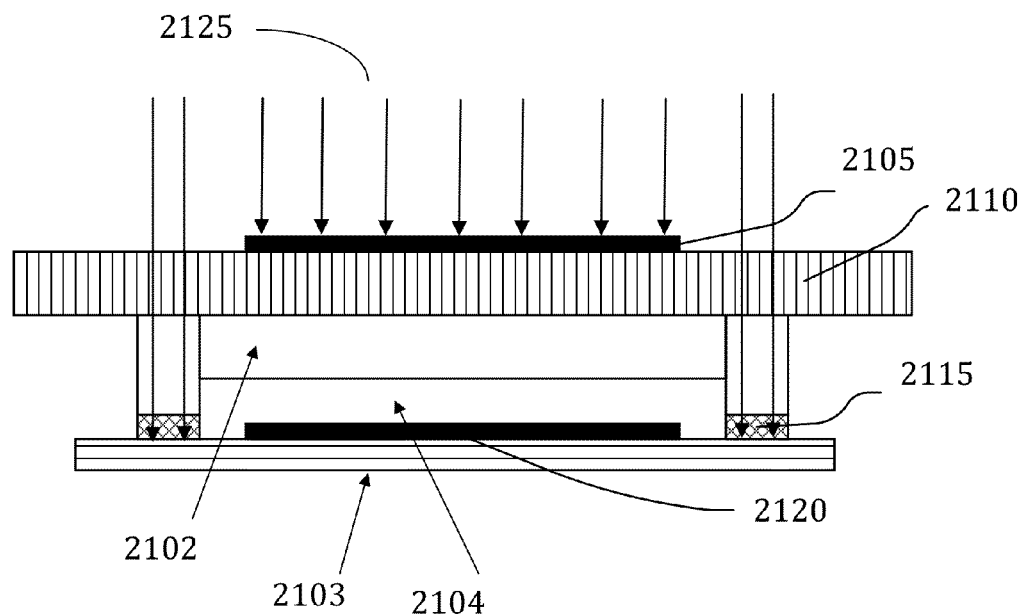
FIG. 21 illustrates an exemplary method of fabrication for a curing an adhesive while protecting reagents applied to a surface inside a reaction chamber.

FIG. 21 illustrates an exemplary method of fabrication for a curing an adhesive while protecting reagents applied to a surface inside a reaction chamber. A cartridge comprising a polymer side (2102) and a metal plate (2103) has a layer of coated reagents (2120) inside the reaction chamber (2104). In order to cure the adhesive (2115), in some embodiments light rays (2125) need to be directed at the adhesive (2115). In order to protect reagents (2120) from the light rays (2125), a mask (2105) supported by a transparent plate (2110) may be used to block certain rays while allowing other rays to cure the adhesive (2115).

Figure 22:
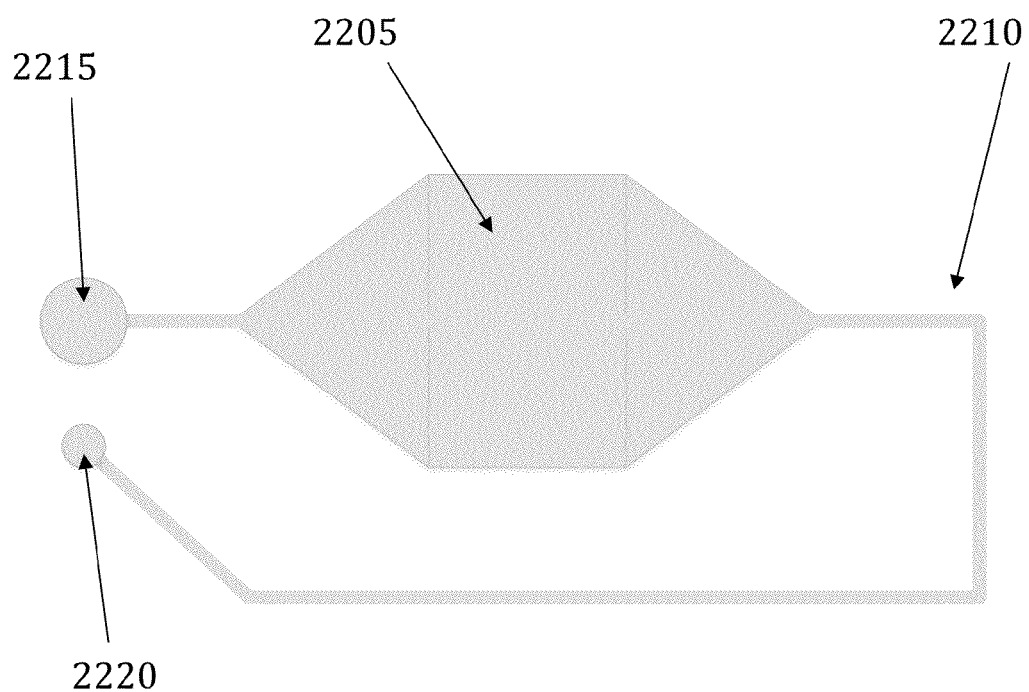
FIG. 22 illustrates an exemplary reaction chamber with inlet and outlet or vent ports.

FIG. 22 illustrates an exemplary reaction chamber with inlet and outlet or vent ports. In some embodiments, a reaction cartridge may comprise a reaction chamber (2205) connected through microfluidics channels (2210) to an inlet port (2215) and an outlet port or vent port (2220). Such ports (2215, 2220) may be placed on the same side of a cartridge for ease of access.

Figure 23:
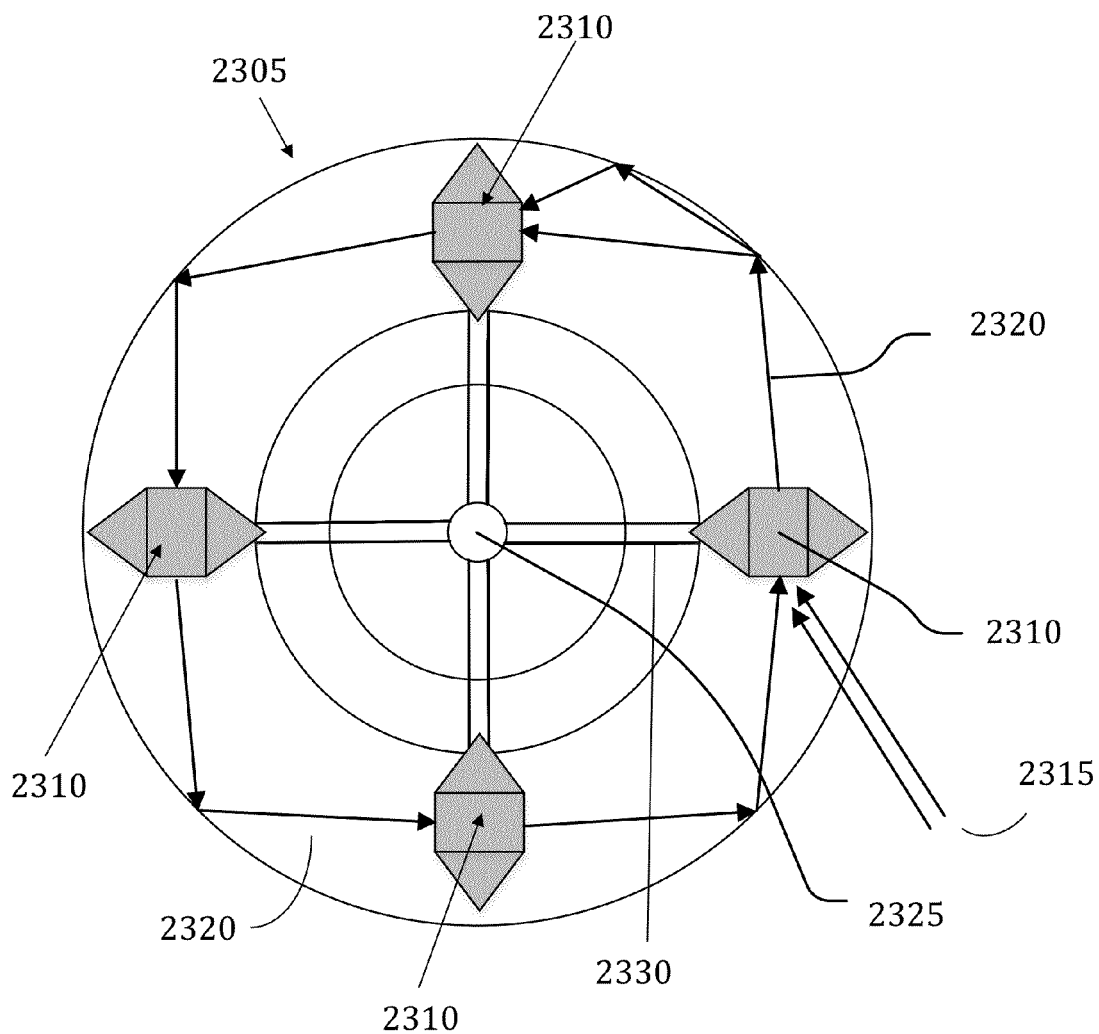
FIG. 23 illustrates a circular embodiment of a cartridge with several reaction chambers or reservoirs.

FIG. 23 illustrates a circular embodiment of a cartridge with several reaction chambers or reservoirs. A circular structure or cartridge (2305) may comprise several chambers or reservoirs able to contain liquid samples, for example four chambers (2310). Light rays (2315), originating from a light source, may be directed at one of the chambers (2310). The circular cartridge (2305) may be configured so as to allow internal reflection of light rays (2320) so that a single light source can illuminate all the chambers (2310). In other embodiments, the circular structure (2305) may rotate in order to illuminate one at a time each of the chambers (2310). In FIG. 23, an inlet port (2325) connects to the chambers (2310) through channels (2330).

Figure 24:
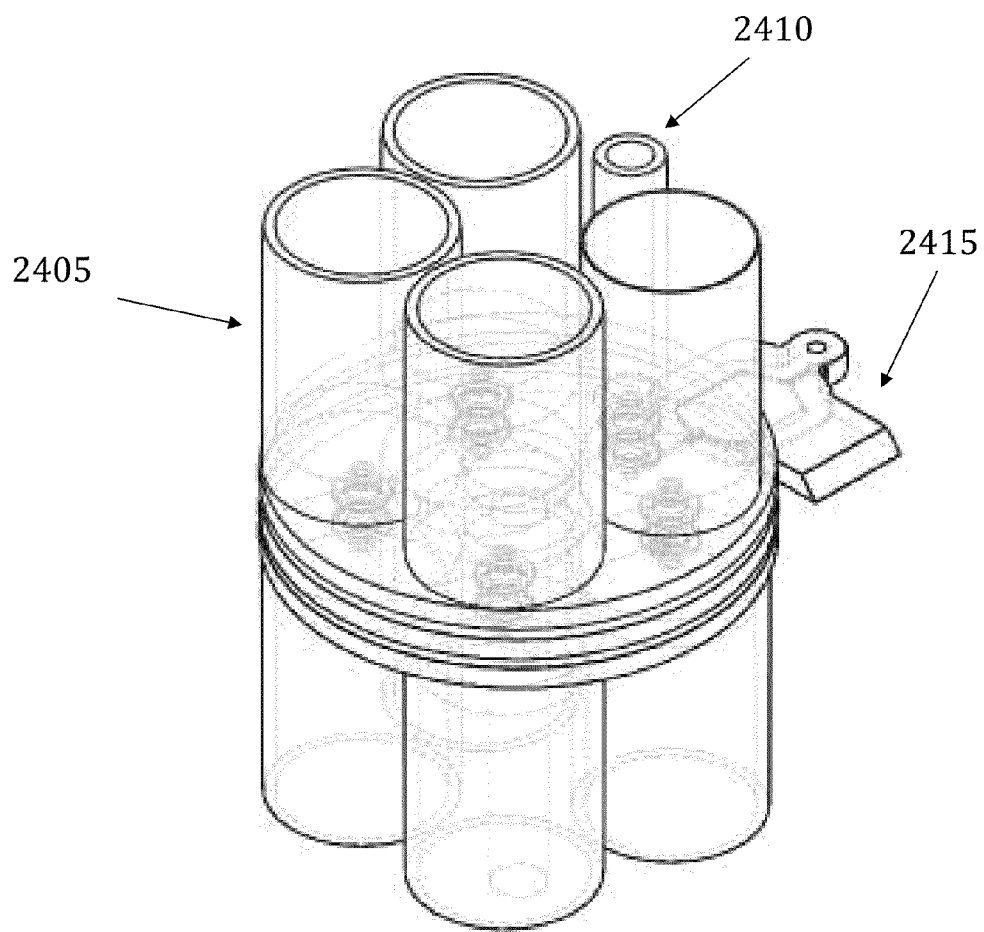
FIG. 24 illustrates an exemplary circular sample-to-answer device.

FIG. 24 illustrates an exemplary circular sample-to-answer device. An arrangement of cylinders (2405) or other similar container structures can be arranged in a circular manner. This arrangement may have the advantage of having a compact shape. The structures (2405) may have different shape or size, depending on the specific application. For example, an elution structure (2410) may have a smaller volume as often the elution requires a smaller volume of liquid as it will be understood by the person skilled in the art. In FIG. 24 a cartridge (2415) is also present, for example for PCR techniques. The different components of the device of FIG. 24 can be similar as to those previously described in the present disclosure, with a difference being the circular arrangement visible in FIG. 24.

Figure 25:
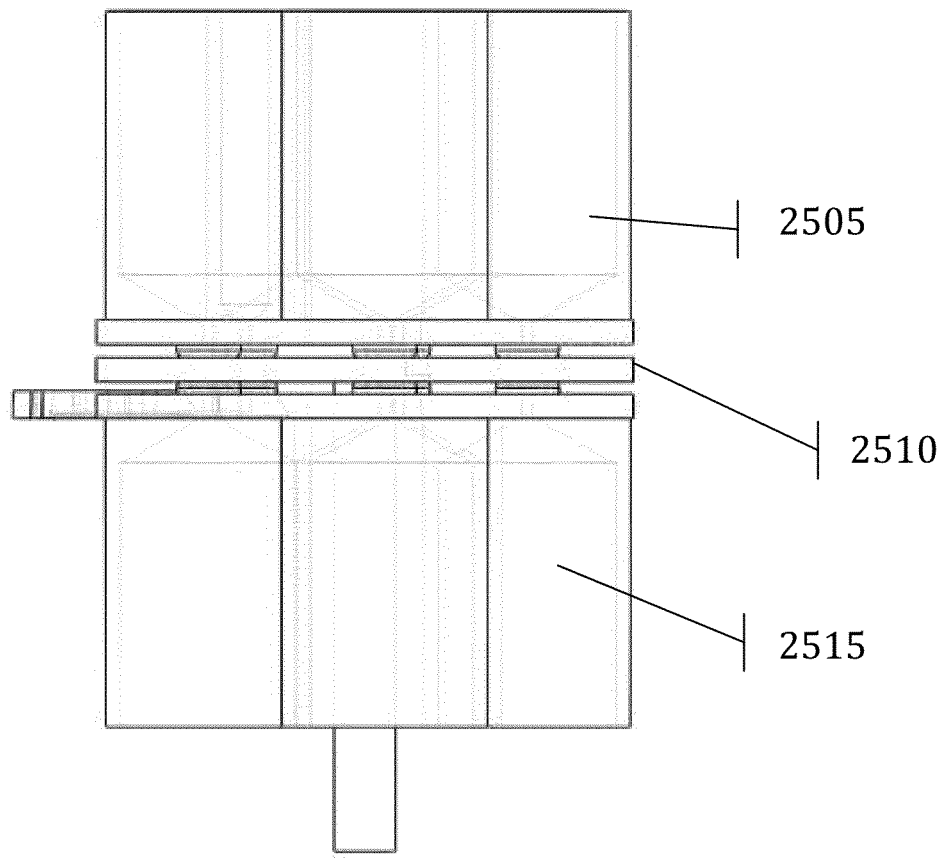
FIG. 25 illustrates a side view of the device of FIG. 24.

FIG. 25 illustrates a side view of the device of FIG. 24. The device of FIG. 25 comprises a top set of cylinders (2505), a bottom set of cylinders (2515), and a central disk (2510) connecting the top (2505) and bottom (2515) set of cylinders.

Figure 26:
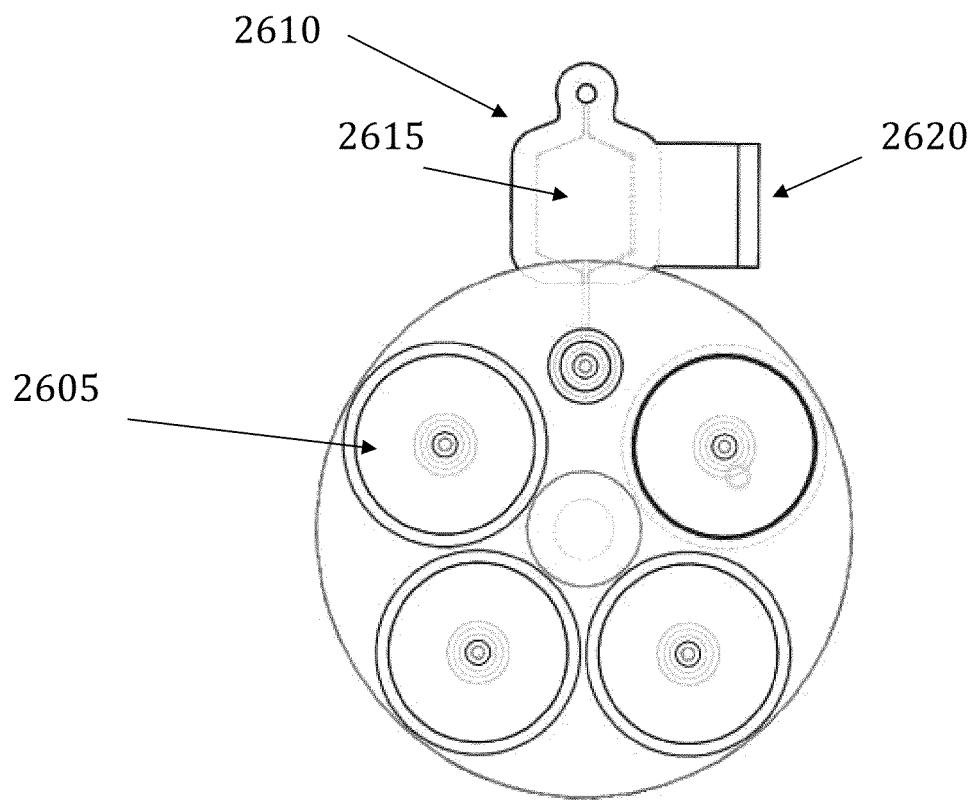
FIG. 26 illustrates a top view of the device of FIG. 24.

FIG. 26 illustrates a top view of the device of FIG. 24. In FIG. 26 a set of cylinders (2605) is visible, as well as a cartridge (2610), the cartridge (2610) comprising a reaction chamber (2615) and a prism (2620).

Figure 27:
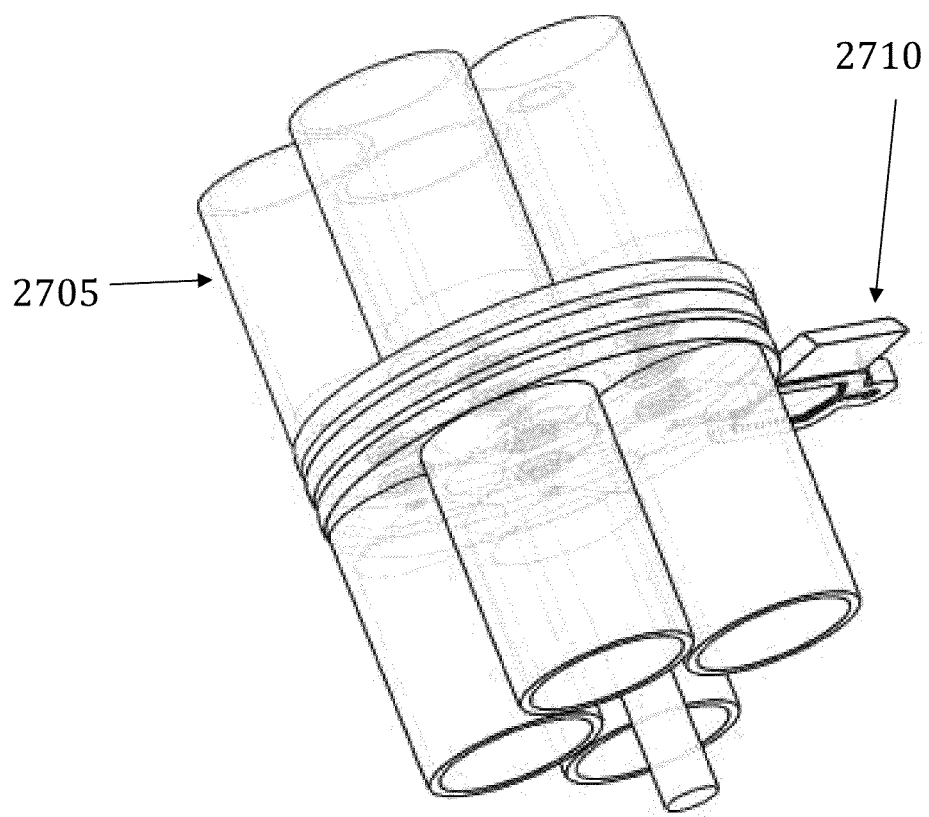
FIG. 27 illustrates a bottom perspective view of the device of FIG. 24

FIG. 27 illustrates a bottom perspective view of the device of FIG. 24. In FIG. 27, a set of cylinders (2705) is visible, as well as a cartridge (2710). In the following, some component parts of the device of FIG. 24 are described in more details.

Figure 28:
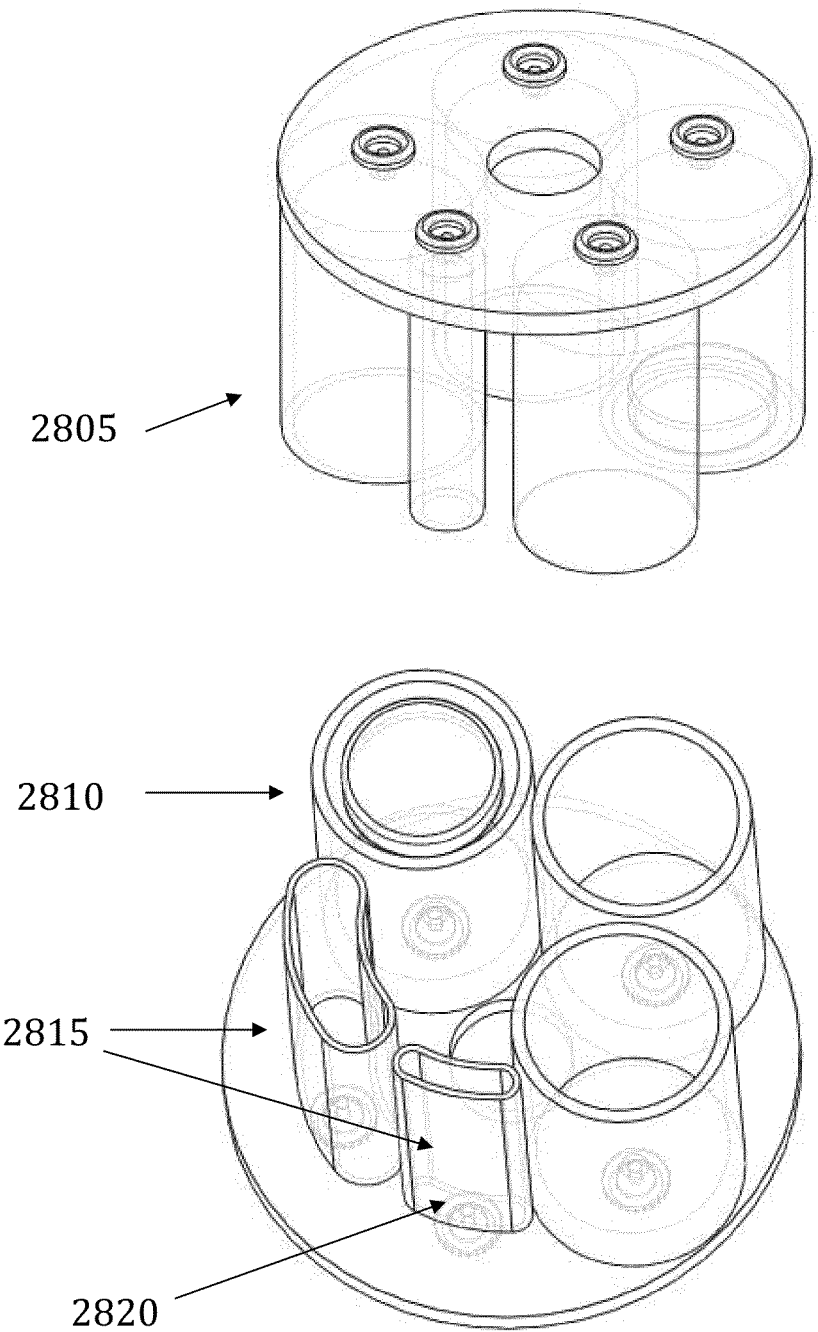
FIG. 28 illustrates a bottom view of two different sets of container structures.

FIG. 28 illustrates a bottom view of two different sets of container structures. A first set of containers (2805) is shown from a bottom view. A second set of containers (2810) is shown from a top view. The second set of containers (2810) may comprise one or more containers which are not in cylindrical shape. For example, containers (2815) have a flattened shape. This shape allows for a higher surface area internal to the containers (2815). Such higher surface area may be advantageous for several reasons, for example increase area to allow for increase rate of reaction for the target analyte in a sample solution and the reagents coated on the surface. Another advantage may be increase area for controlling the temperature of the solution. For example, an external heater (2820) may be attached to an external surface of a container (2815), allowing for thermal cycling, heating or cooling, depending on the requirements of the technique used.

In some embodiments, different thin films can be used as heaters. For example, laminates like DuPont Pyralux APR (embedded resistor laminate) can be used. In some embodiments, they can be bonded to a metallic surface using thin dry film adhesives, for example as those used in the printed circuit board industry as understood by the person skilled in the art.

A temperature sensor can also be deposited, for example on a kapton laminate. The temperature sensor can be made, for example, with deposited platinum, copper, nickel or other metals.

Copper tracks on a standard flexible laminate can also be used as a heater. The temperature sensor could also be fabricated with a copper laminate. The resistance of sensor can be controlled as necessary by controlling the thickness of the conducting metal element.

In some embodiments, the heater can be a part of metal plate, without comprising any polymer, in order to have increased total thermal conductivity. For example, if the base of a heater is metallic (for example, aluminum or copper) then one side of the metal can be anodized, to render it electrically insulating. $SiO_2$ or other insulating coatings can also be applied. In other embodiments, a nichrome heater could be deposited as a heating element, while copper tracks can be deposited as contacts. As understood by the person skilled in the art, current can be passed through a metallic element to increase its temperature, in order to act as a heater.

Figure 29:
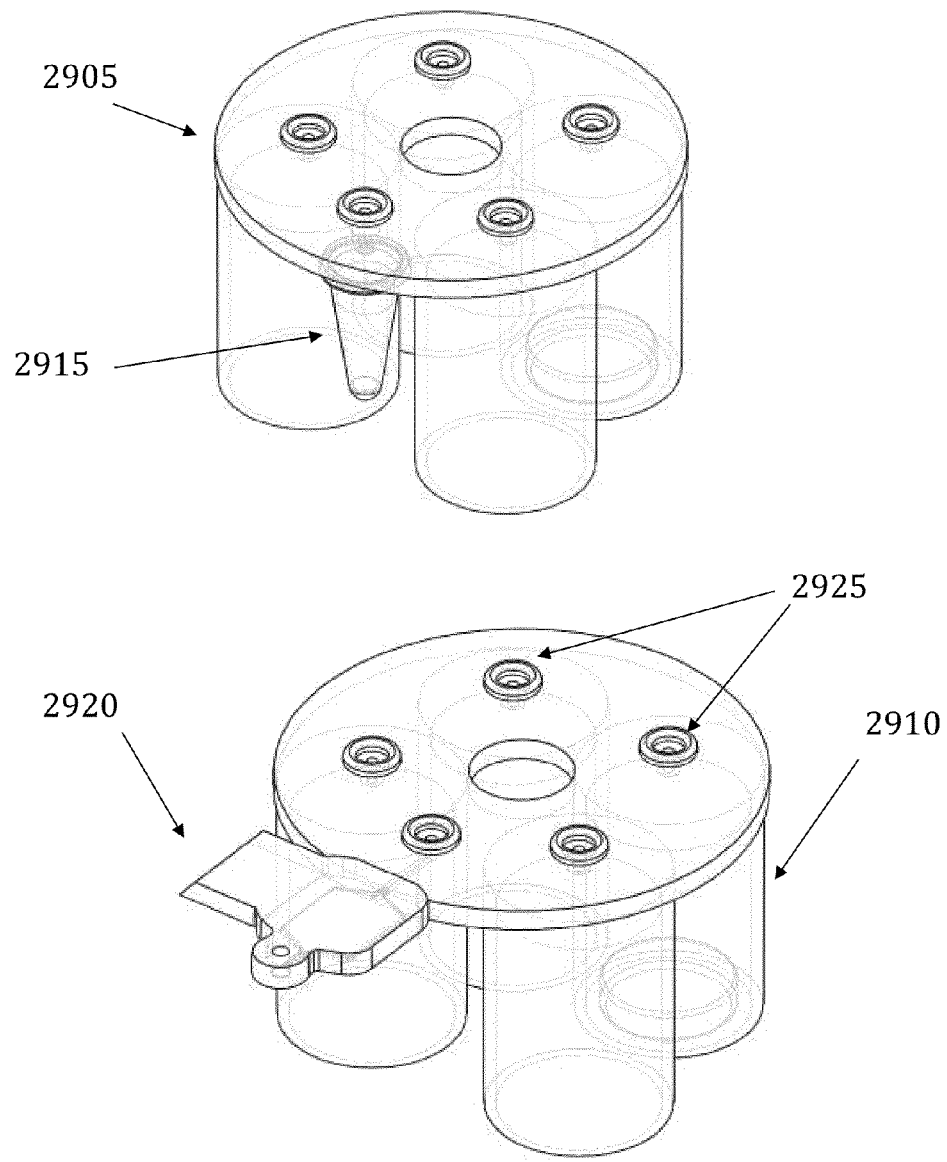
FIG. 29 illustrates an example of two bottom sets of container structures.

FIG. 29 illustrates an example of two bottom sets of container structures, from a top point of view. One set of containers (2905) is for a sample preparation device. A container (2915) for collection of the prepared sample is visible.

Another set of containers (2910) is for a sample-to-answer device, comprising a reaction cartridge (2920).

Figure 30:
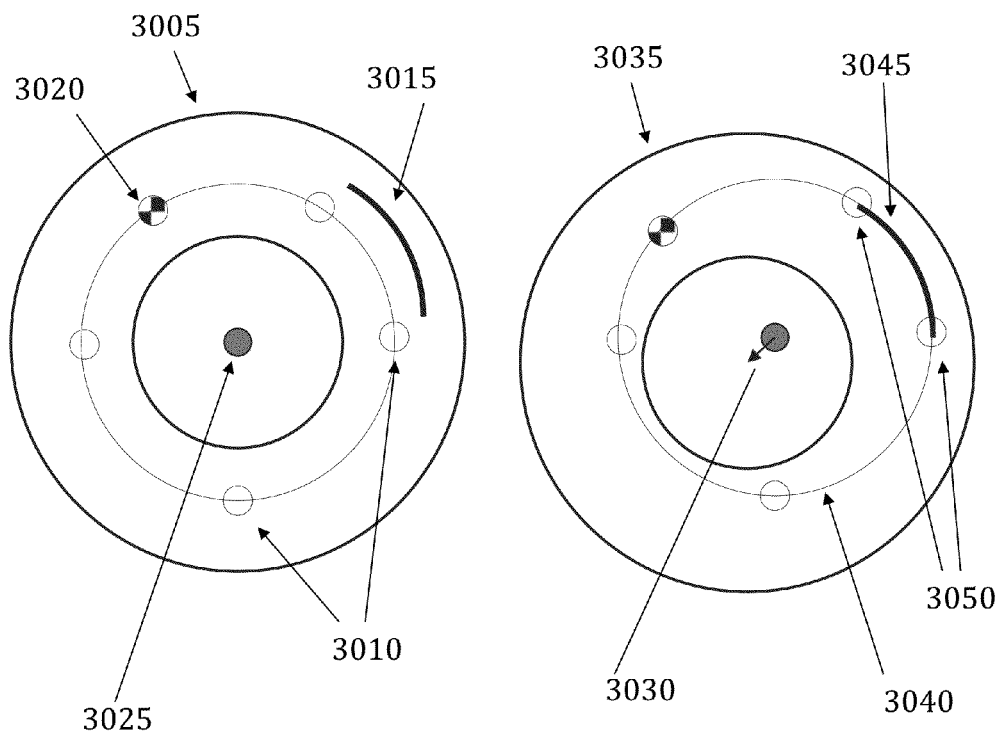
FIG. 30 illustrates an exemplary connecting disk of a circular device.

FIG. 30 illustrates an exemplary connecting disk of a circular device. Such connecting disk may correspond, for example, to element (2510) in FIG. 25. Referring to FIG. 30, the connecting disk structure (3005) is configured so as to slide horizontally, or move relative to the rest of a device. A set of apertures (3010) are visible which correspond to apertures in the containing structures of the device, for example cylinders (2910) of FIG. 29. In FIG. 29, apertures (2925) can be connected by a connecting channel in the connecting disk, such as channel (3015) in FIG. 30.

Referring to FIG. 30, channel (3015) can be used to connect containing structures in the rest of the device. In this embodiment, the five apertures (3010) visible in FIG. 30 are not a part of connecting disk (3005) but are shown to explain the operation of this embodiment of the device. Channel (3015) is part of disk (3005), and by moving disk (3005), apertures (3010) can be connected by channel (3015), thereby allowing the movement of fluids between containing structures of a device. A sample holder (3020), for example a DNA binding matrix, is shown as an example, at a site of one of the apertures of a container structure. By moving disk (3005), the sample holder (3020) may be moved between any of the five apertures (3010). In other embodiments, a different number of containing structures may be used.

In FIG. 30, the center (3025) of a device is shown to exemplify a movement of disk (3005). For example, disk (3035), which corresponds to disk (3005) before the movement, is moved in the direction indicated by arrow (3030). Disk (3035) is then now translated horizontally relative to the apertures in the containing structures which are located, for example, in a circular pattern (3040). Channel (3045), corresponding to channel (3015) before movement of disk (3005), is now connecting two adjacent apertures (3050). It will be understood by the person skilled in the art that different variations of size and shape and arrangement of the components similar to those described in the present disclosure may be possible, and the examples here described are not intended as a limitation.

Figure 31:
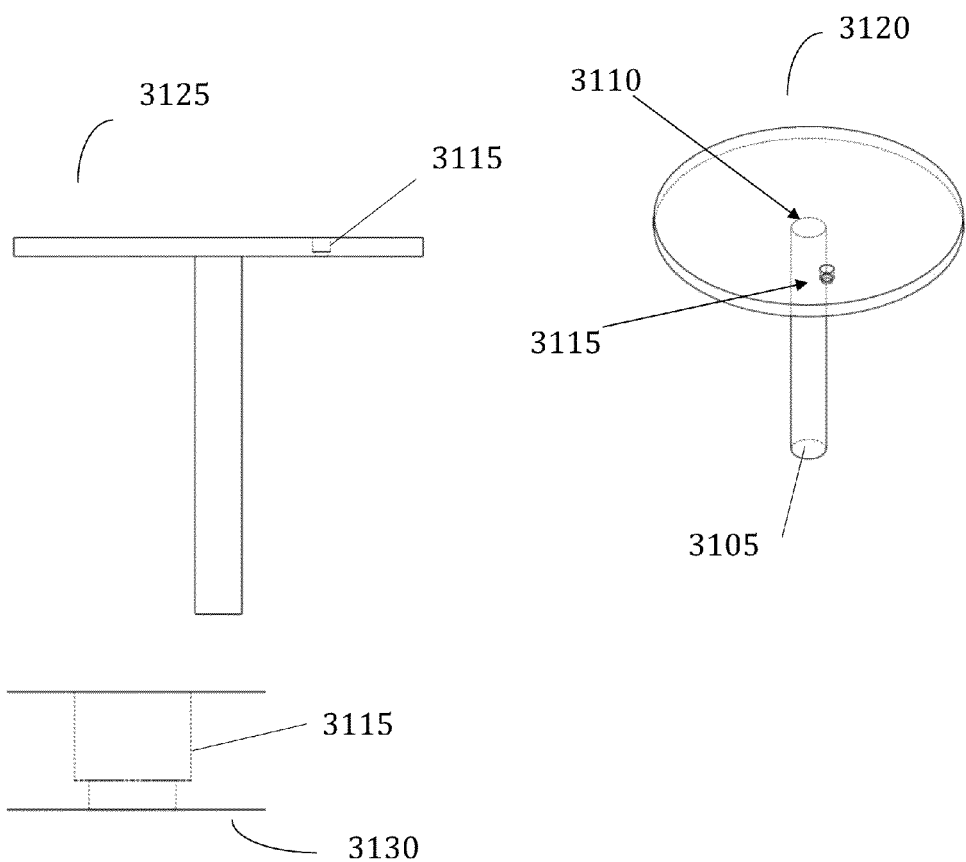
FIG. 31 illustrates an exemplary rod to control a connecting disk.

Disk (3005) may be moved by a variety of means, for example by a handle on a side of the disk, or by a rod attached to the bottom of the disk. For example, as visible in FIG. 31, a rod (3105) may be attached to the center of a disk (3110). A slot (3115) for a sample holder (such as a DNA membrane) is visible. The structure is shown in perspective view (3120) as well as side view (3125).

In an additional view (3130), a zoomed in view of slot (3115) is illustrated. Slot (3115) is configured to hold a sample holder in a stable position, while allowing movement of fluid in and out of the sample holder as desired. Rod (3105) may be rotated or moved in the horizontal plane of the connecting disk (3110). Slot (3115) may have a countersink shape to facilitate holding of the sample container, such as the DNA membrane.

As understood by the person skilled in the art, the devices and instruments of the present disclosure can be used for a variety of techniques, for example nucleic acid sample preparation. Nucleic acid sample preparation is a highly labor intensive and time consuming process requiring multiple steps to collect DNA and/or RNA from biological materials such as whole blood, blood serum, buffy coat, urine, feces, semen, saliva, sputum, nasopharyngeal aspirate, spinal fluid, and tissue from biopsies. Nucleic acid isolated from said biological materials can also comprise the endogenous nucleic acid from the organism from which the sample is derived and any foreign (viral, fungal, bacterial or parasitic) nucleic acid.

To simplify the steps in the sample preparation process, the present disclosure comprises the use of a fluidic cartridge for extraction and purification of nucleic acid from biological material. This invention can offer the advantages of being rapid, low cost, reliable, and portable, thereby yielding high purity DNA and/or RNA that can then be used as a reagent in molecular biological reactions. The present disclosure can support a range of applications and extraction protocols; and can comprise both automated and manual operation.

One of the first steps in many laboratory tests is the isolation and purification of nucleic acid, which is essential to a wide variety of biotech, research, forensic, and clinical applications. These procedures can consume considerable time, labor and costly materials. In order to ensure easy and inexpensive point-of-care diagnostics, it would be advantageous if little or no sample preprocessing at the bench were required.

The devices of the present disclosure can simplify sample preparation by combining all of the complex protocols of DNA and/or RNA extraction into just a few steps. The steps for isolating nucleic acid from biological materials comprise (1) take in the biological sample via the sample input port; (2) mix sample with lysis buffer and lyse the nuclei acid-containing cells, tissue, etc.; (3) bind nucleic acid to porous nucleic acid binding membrane; (4) remove contaminants with wash buffer; (5) air dry; and (6) elute nucleic acid in buffer or water. Concentration and purification of nucleic acid can makes each sample ready for downstream molecular diagnostic testing with yields comparable to industry-standard methods.

In several embodiments of the disclosure, the sample holders are based on a porous nucleic acid binding membrane which can be embedded in a single-use bar or connecting disk. The bar slides back-and-forth along the center of the cartridge and aligns the nucleic acid binding membrane with the opening of each port pair. Alternatively, the disk can move in a plane for a similar purpose. The bar or disk can be fitted with nucleic acid binding membranes from various types of commercially available DNA/RNA extraction kits, thus allowing the fluidic cartridge to extract from a wide range of source comprising: Human genomic DNA from blood, saliva, or semen; DNA and RNA from bacteria such as *Staphylococcus aureus* and *Streptococcus pyogenes*; DNA and RNA from blood-borne microbes such as *B. anthracis*; Microbial DNA in culture, urine and more for such microbes as *B. anthracis*, Adenovirus, and *E. coli*; Viral RNA in culture, urine and more for Herpes Virus I, and *Chlamydia trachomatis*; Influenza A and B from nasal aspirate and respiratory swab samples in viral transport media.

The sample preparation cartridge's flexible protocol can work with chaotropic salt chemistry and can be designed to handle a range of sample volumes, for example in the range 50 J.LL-10 mL). Additionally, in order to work directly with human whole blood samples, whole blood filters can be incorporate into the device.

The sample preparations and sample-to-answer devices of the present disclosure can comprise complementary port pairs on both the bottom and top half of a device, as visible for example in FIG. 27. Each of the top containers can contain reservoirs for the appropriate buffer solutions for each step of a desired technique. The containers can be pre-filled with the solutions or solutions can be added manually during each step. In several embodiments, the bottom half of the devices can contains ports which act as waste reservoirs for the buffer solutions.

In some embodiments, a sample is first mixed with a high-salt lysis buffer, (which could contain magnetic beads, colloidal gold particles, silica, etc.) to chemically or mechanically lyse the cells. Mixing can be achieved by external ultrasonic or vibration coupled to the inertion port of the device. Additionally, the reservoir could have a heater surrounding it to perform thermal lysis; or also include a magnetic element to perform magnetic lysis.

The mixture can then be passed through a nucleic acid binding matrix using a piston/actuator mechanism. Fluid can flow through the nucleic acid binding membrane. High pressure can be applied allowing rapid operation. By matching the shape of a piston or plunger to the reservoir, •the piston will force the majority of the fluid to the complimentary port on the other side; thus minimizing the dead volume. Additionally, the fluid can be pushed/pulled back through the membrane between pairs of ports. This allows multiple passes through the nucleic acid binding membrane which will enhance binding of the nucleic acid to the membrane. The pistons can also be moved slowly or stopped to allow greater binding time.

Once the nucleic acids are bound to the membrane, the bar or disk can slide to the next set of ports to perform a washing step. Washing the nucleic acid can encompass one cycle or multiple cycles to further enhance binding of DNA and/or RNA to the membrane and for efficient removal of contaminants.

Next, the bar can move to the next set of ports to perform an air drying step. By moving the pistons up and down inside the ports, air can be aspirated through the nucleic acid binding membrane and dry the membrane. Furthermore, a heating element can also be incorporated to help dry the membrane faster and evaporate off any residual wash buffer.

Further, the isolated nucleic acids can be eluted off the membrane in buffer or water solution. A heating element can also be incorporated around the port to control the temperature of the elution buffer and maximize the release of nucleic acid. The eluent containing the released nucleic acid can be captured in a PCR tube attached to the sample output port or directly injected into a molecular diagnostic device for analysis.

The devices of the present disclosure can be injection molded, compression molded, 3D printed or rapid prototype printed from numerous types of materials, including but not limited to thermoplastic, metal, glass, and elastomers.

Several embodiments of the devices of the present disclosure can allow for manual and automated operation. For manual operation, these devices can be run completely by a hand-held syringe, plunger, piston, or similar element. Insertion ports can be configured for direct insertion of syringes, needles, pipette tips or luer lock tips.

The devices of the present disclosure may have applications in the areas of analytical chemistry, forensic chemistry, microfluidics and microscale devices, medicine, and public health. They may be useful for a wide variety of applications including fluid manipulation, diagnostic and analytical test, chemical and biological analysis, food safety, drug testing, fluid metering and others.

Figure 32:
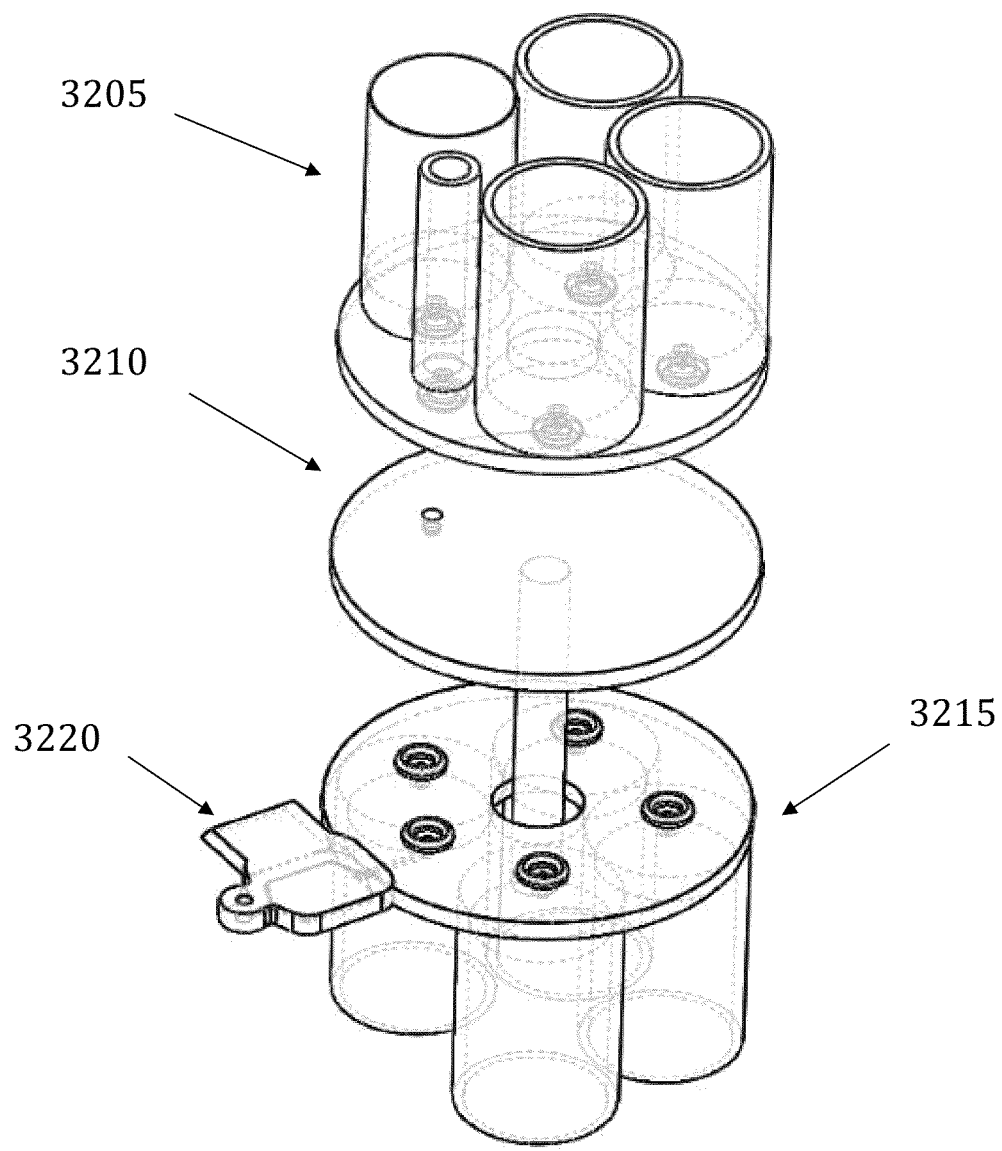
FIG. 32 illustrates an exploded view of an exemplary circular sample-to-answer device.

FIG. 32 illustrates an exploded view of an exemplary circular sample-to-answer device, comprising a top set of containers (3205), a connecting disk (3210), a bottom set of containers (3215) and a reaction cartridge (3220).

Figure 33:
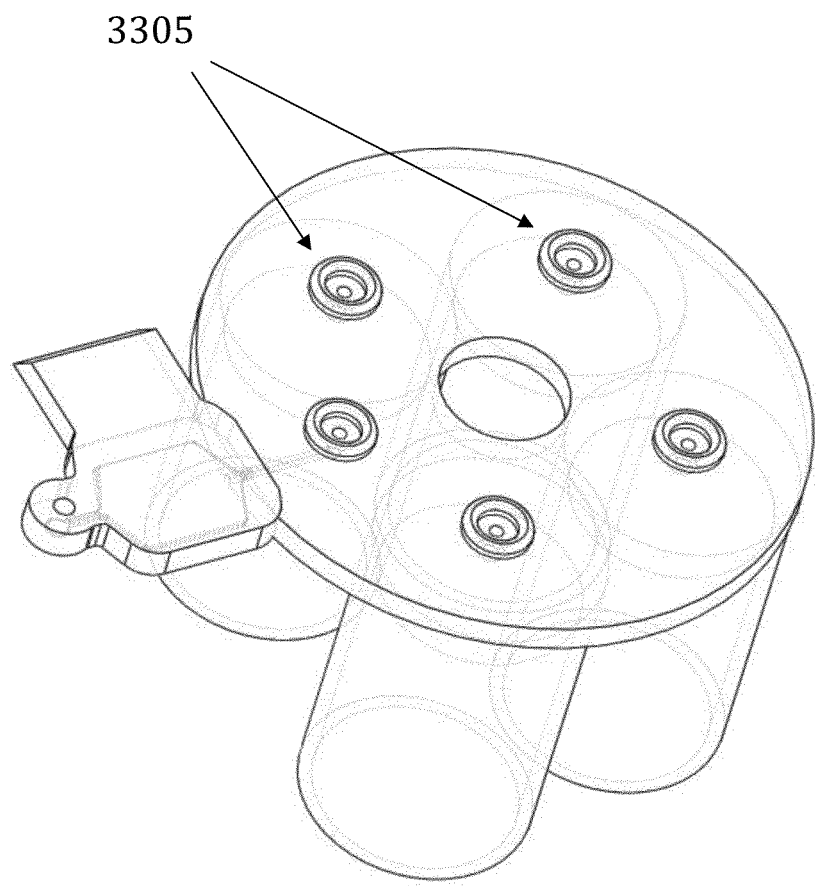
FIG. 33 illustrates exemplary sealing rings.

FIG. 33 illustrates exemplary sealing rings (3305) which provide sealing between a set of containers and a connecting disk.

Figure 34:
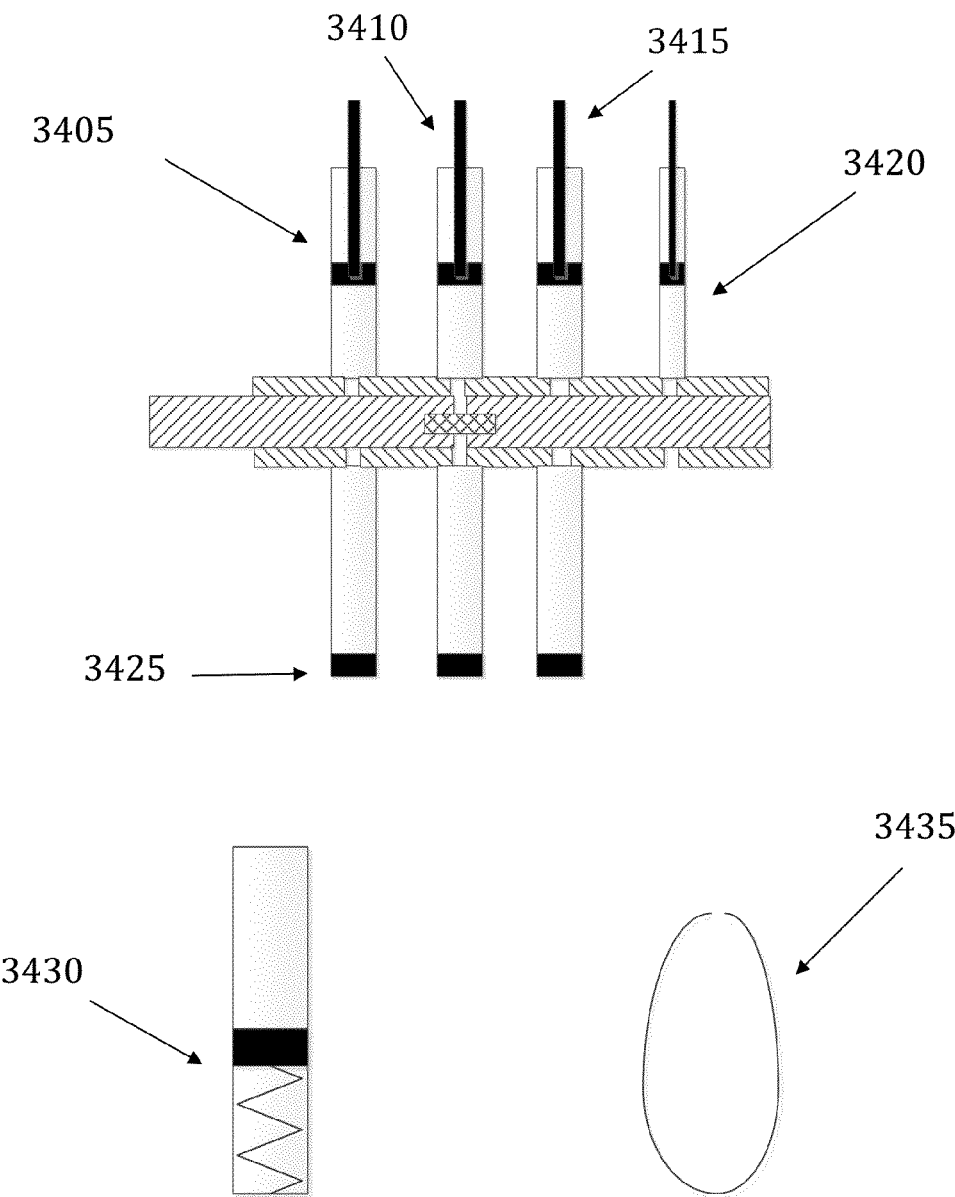
FIG. 34 illustrates different possible features of container structures.

FIG. 34 illustrates different possible features of container structures. A container (3405) may be used for the sample, lysate or mixture. Containers (3410) and (3415) may be for different washes. Container (3420) may be for elution. In some embodiments, the bottom containers may have air-permeable membranes (3425), elastic pistons (3430) or flexible reservoirs (3435). For example, reservoirs (3435) may be flexible and may be squeezed by hand, similarly to a rubber balloon. The air-permeable membranes (3425) may be useful for drying as the membranes (3425) can allow air through, but not fluids or DNA. In some embodiments, hot air can be directed onto the air-permeable membranes (3425) in order to dry the content of a container. The elastic pistons (3430) may comprise a spring attached to a seal. As fluid is inserted in a container, the spring is pushed back, and when pressure is not applied against it anymore, the spring will push back against the fluid in the container, thereby enabling its movement thanks to the elastic energy stored in the spring of the elastic piston (3430).

Figure 35:
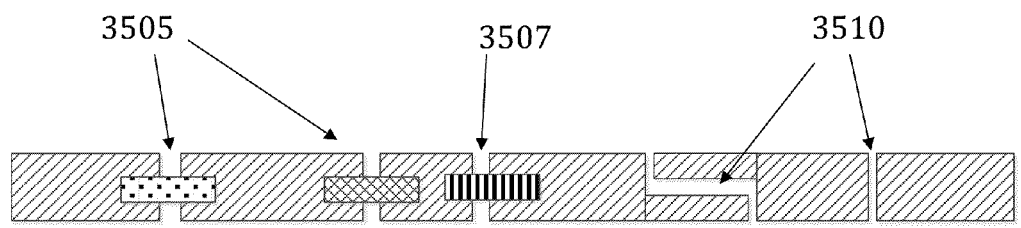
FIG. 35 illustrates different possible elements of a sliding bar.

Container structures of the devices of the present disclosure may be used, for example, for homogenization, lysis, filtration, mixing, ultrasonic lysis, debubbling, or protein filtering. The containers may also be empty. Similarly, the sliding bars or connecting disks as described in the present disclosure, may house elements which can perform different functions other than holding a sample. For example, FIG. 35 illustrates different possible elements of a sliding bar. Different sample holders may be used (3505), for example different membranes. Filters, mixers or homogenizers (3507) may also be used, or even empty channels (3510) to connect different containers of a device and allow the movement of fluids between the container structures.

Figure 36:
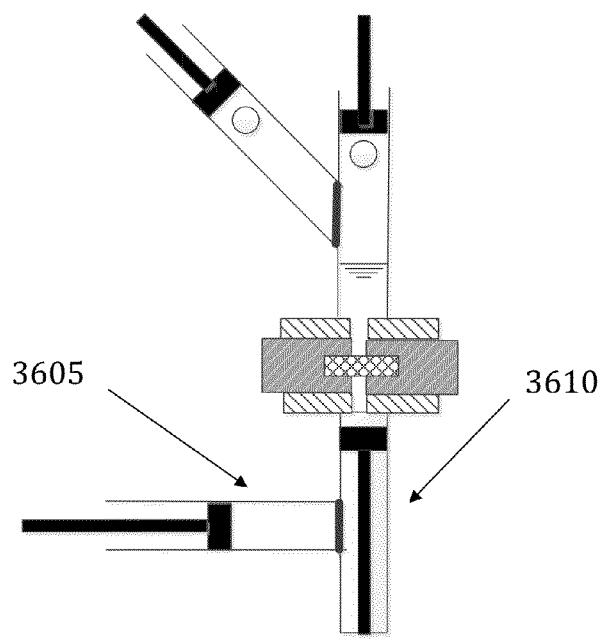
FIG. 36 illustrates one embodiment of a container arrangement.

In some embodiments, additional containers may be added, for example as illustrated in FIG. 36. A first container (3605) maybe used, for example, to insert a fluid in a second container (3610). For example, ethanol may be used to enhance binding. Alternatively, the second container (3610) may also be filled with ethanol or other fluid.

Figure 37:
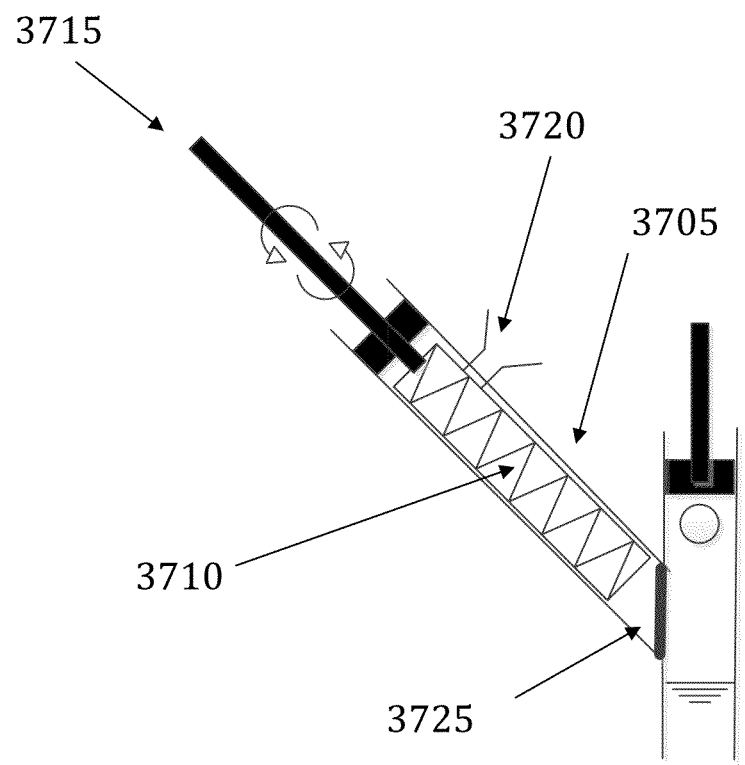
FIG. 37 illustrates an embodiment of a sample insertion container.

FIG. 37 illustrates an embodiment of a sample insertion container for the sample-preparation or sample-to-answer devices of the present disclosure. For example, a side container (3705) may house a grinder element (3710). This grinder element (3710) may be used to grind solid samples, or liquid samples which container solid particles or semi-solid parts. The grinder element (3710) may be operated, for example, by rotating a handle (3715). The side container (3705) comprises a sample insertion port (3720) and may comprise a filtering element (3725), for example an element with a sharp teethed structure which can aid in grinding or mixing a sample.

Figure 38:
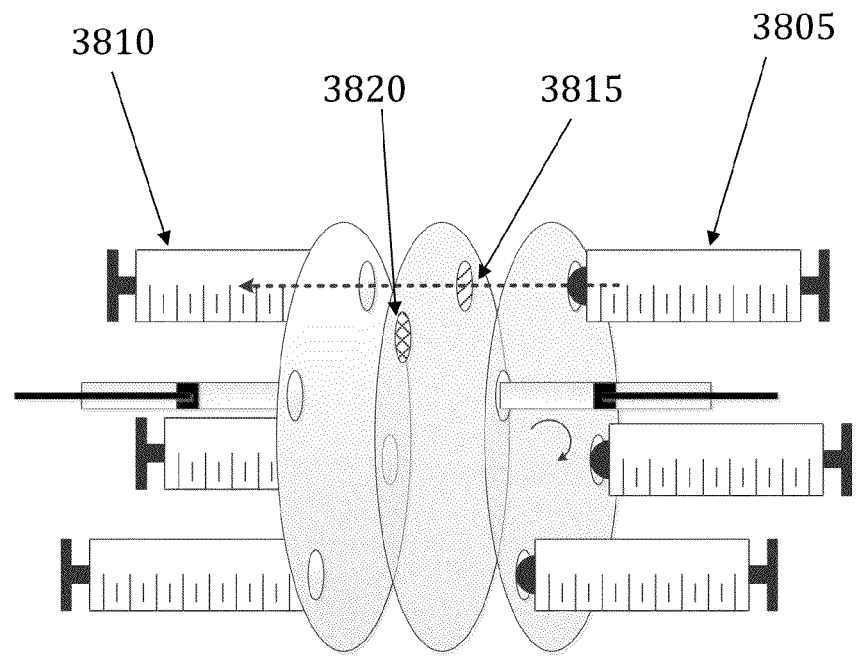
FIG. 38 illustrates an exemplary operation of a sample preparation device.
Figure 38:
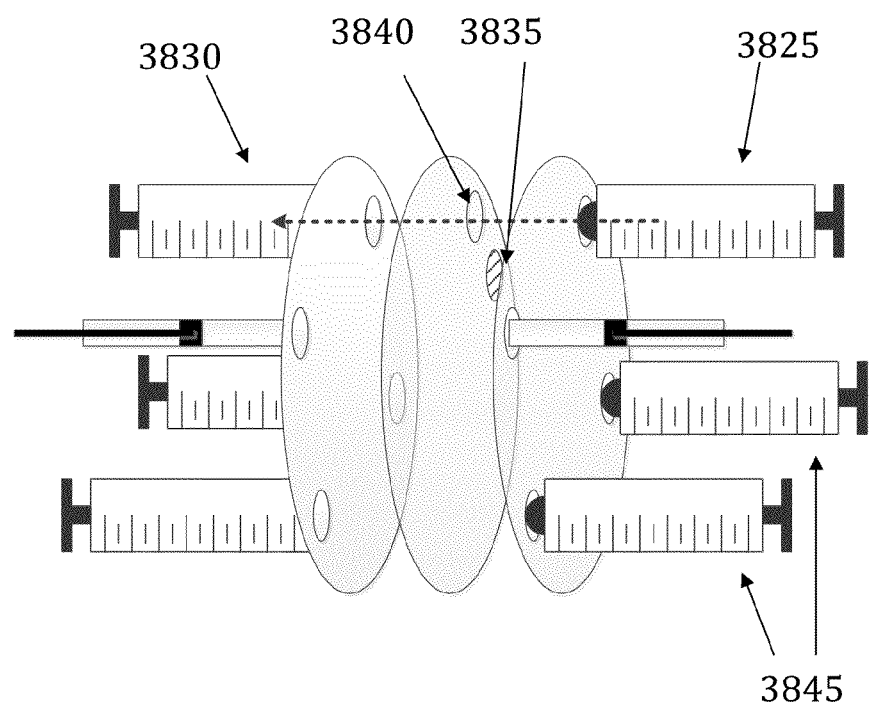

FIG. 38 illustrates an exemplary operation of a sample preparation device. A lysate, sample or mixture may be moved from one container (3805) to the opposite one (3810), with the fluid flowing through a DNA membrane (3815). Another functional element (3820) may be present, for example a filter, mixer, or lysing element, configured to work with a lysing technique, such as electric, magnetic, mechanical, or ultrasonic lysing.

Alternatively, a sample may be moved from a container (3825) to the opposite one (3830) through an empty channel opening (3840), while the DNA membrane (3835) has been rotated to a different position. Other containers (3845) may contain, for example, a washing solution, as understood by the person skilled in the art.

Figure 39:
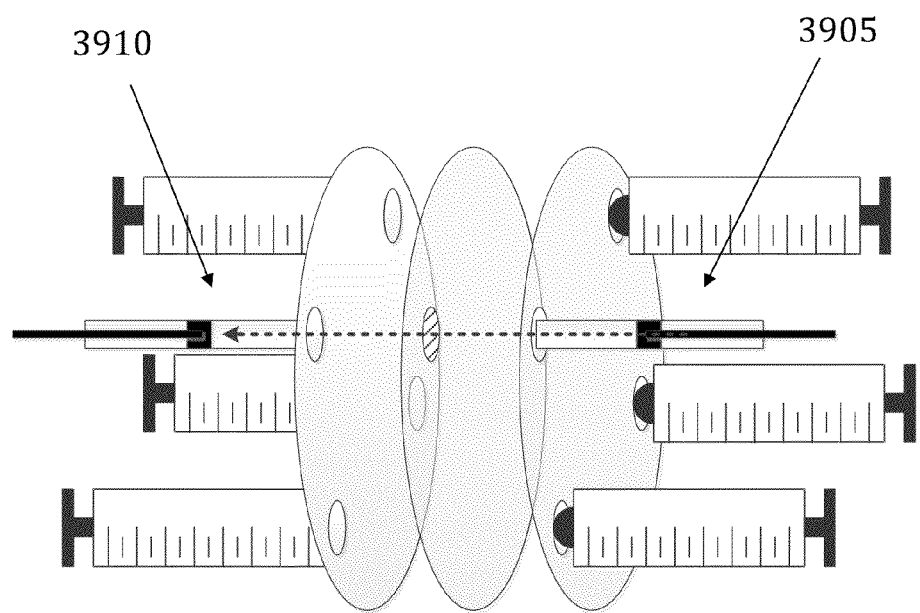
FIG. 39 illustrates an elution process.

FIG. 39 illustrates an elution process, where the fluid, after previous processing in the sample preparation device, undergoes elution and is moved from one container (3905) to the opposite one (3910).

Figure 40:
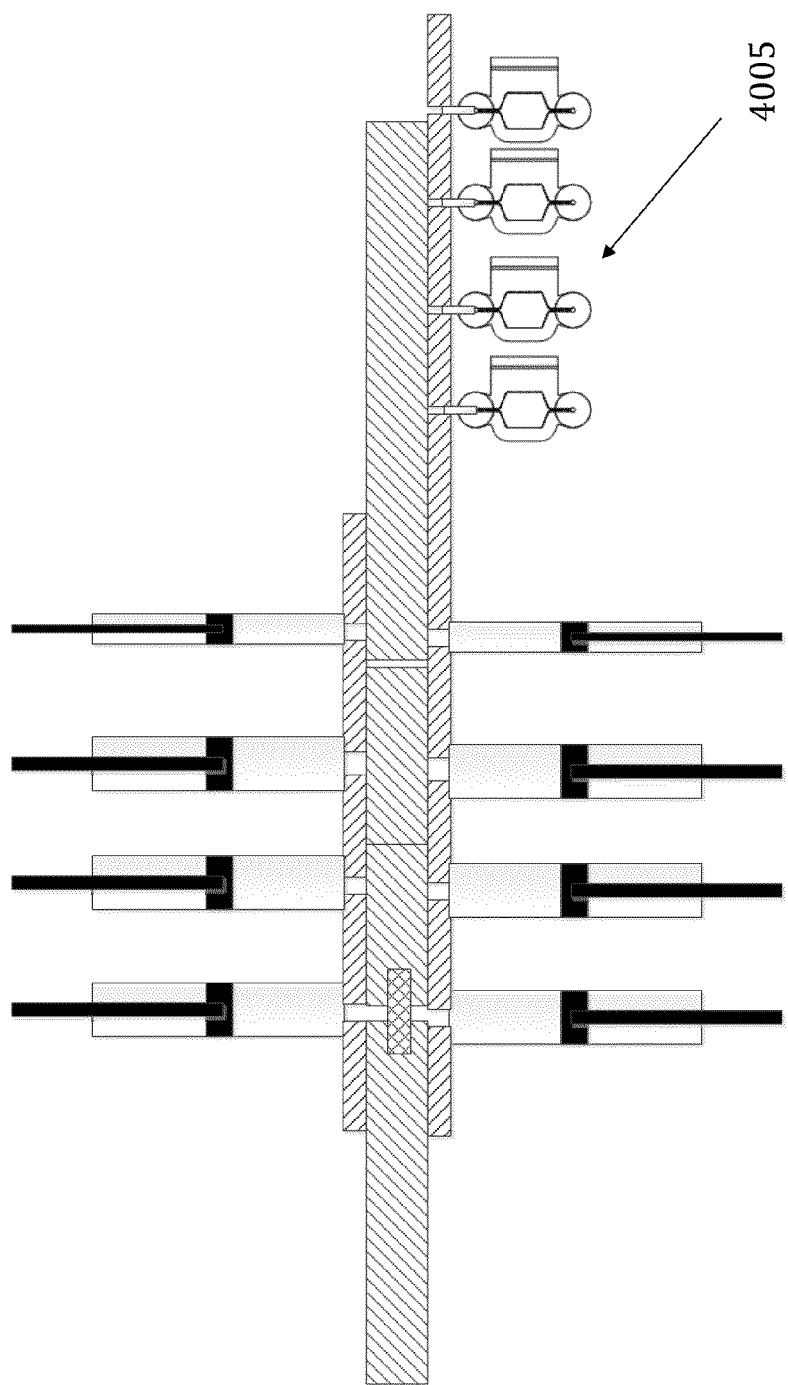
FIG. 40 illustrates an exemplary sample-to-answer device with reaction cartridges attached.

FIG. 40 illustrates an exemplary sample-to-answer device with reaction cartridges attached (4005).

Figure 41:
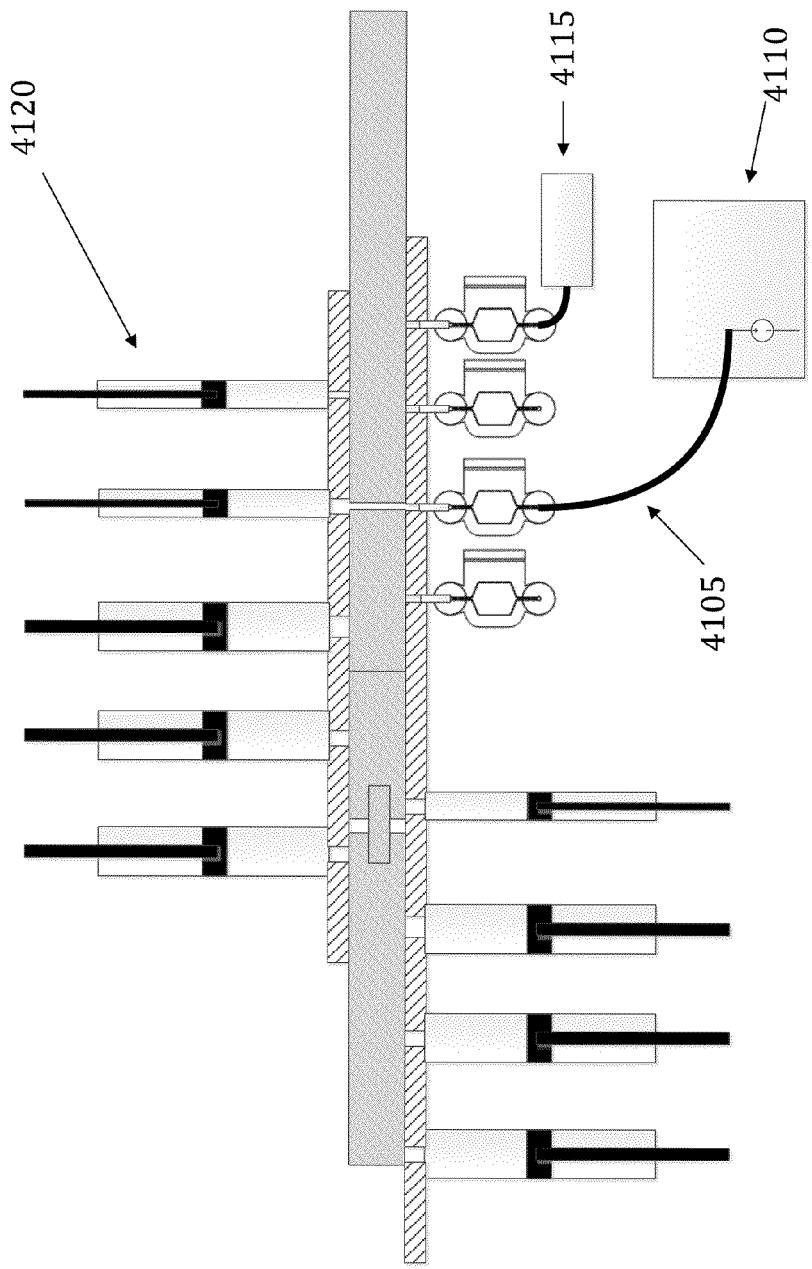
FIG. 41 illustrates an exemplary sample-to-answer device configured for capillary electrophoresis.

FIG. 41 illustrates an exemplary sample-to-answer device configured for capillary electrophoresis. A capillary (4105) attached to a capillary electrophoresis instrument (4110) enables the separation of biological species through a voltage difference, as it is known to the person skilled in the art. A hybridization chamber (4115) is also visible. A container (4120) can be configured to be used as a pump to move a fluid to a capillary electrophoresis buffer or a wash buffer for hybridization.

Figure 42:
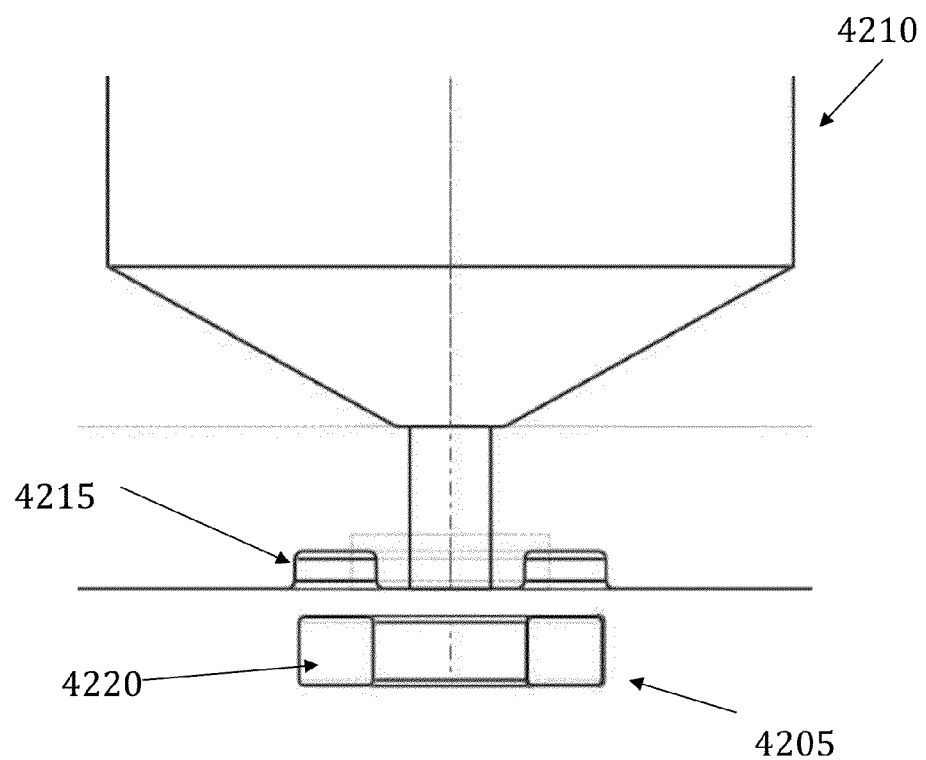
FIG. 42 illustrates an exemplary sealing arrangement between a sample holder and a container structure.

FIG. 42 illustrates an exemplary sealing arrangement between a sample holder (4205) and a container structure (4210). For example, sealing can be obtained with a sealing element (4215), such as an O-ring or a rubber protrusion, and a secondary, or back up, rubber seal (4220).

Figure 43:
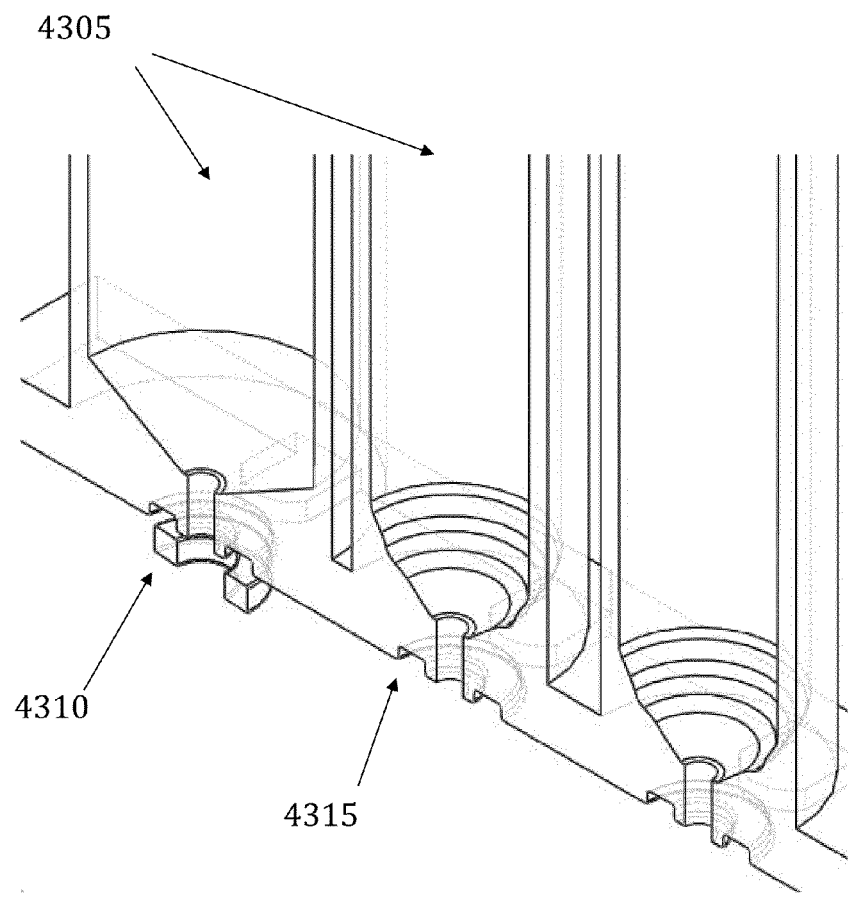
FIG. 43 illustrates an exemplary sealing arrangement in details.

FIG. 43 illustrates an exemplary sealing arrangement in details. Container structures (4305) are partially visible. A sealing element (4310), such as a rubber ring, is shown as detached for clarity. Slots (4315) correspond to the sealing element shape for better sealing.

Figure 44:
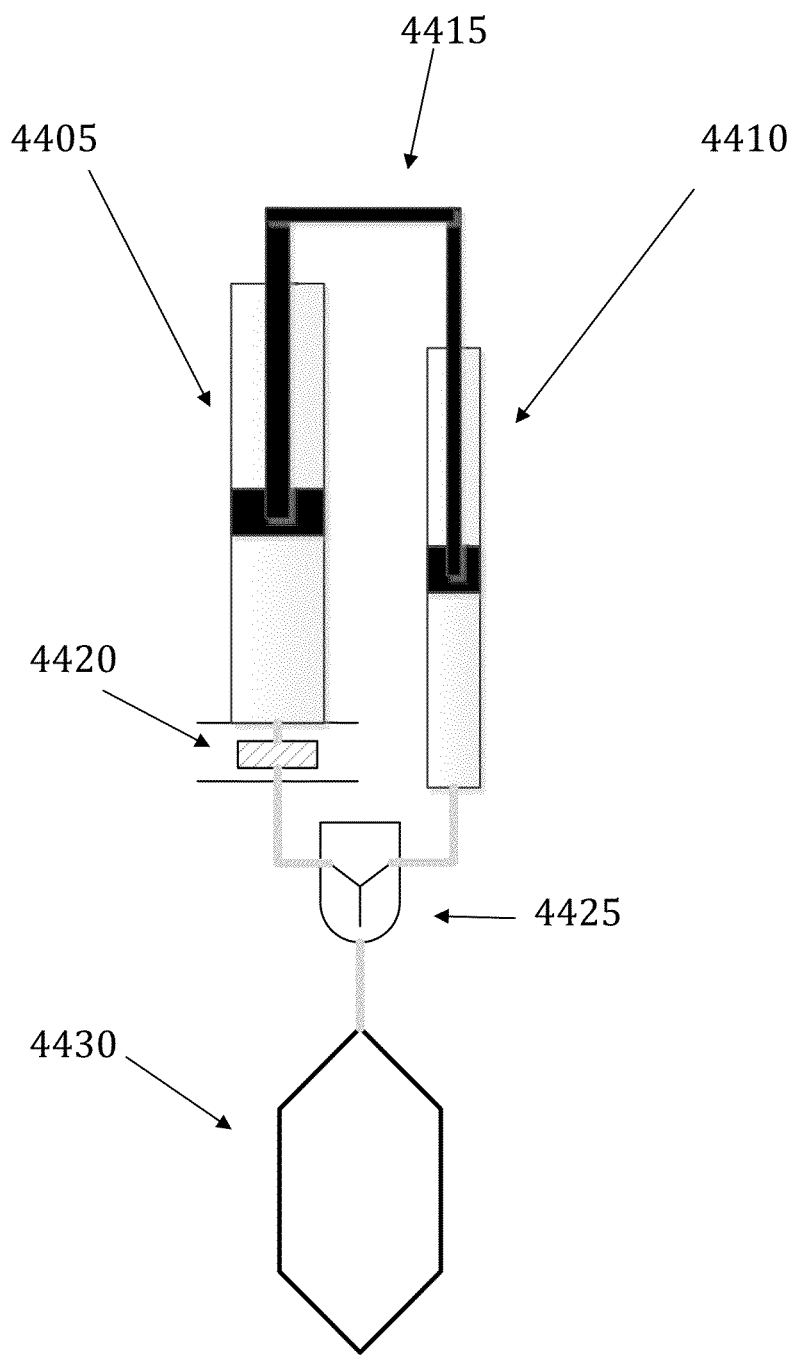
FIG. 44 illustrates some details of an embodiment of a sample-to-answer device.

FIG. 44 illustrates some details of an embodiment of a sample-to-answer device. An elution container (4405) which may be part of a sample-to-answer device as described above in the present disclosure, can be tied, in this embodiment, to an additional container (4410), so that they are both operated simultaneously. For example, the two containers (4405, 4410) may be operated by a single plunger (4415). If the volume of the two containers (4405, 4410) is accurately measured, then it is possible to determine and configure a desired ratio between the fluids contained in both containers (4405, 4410). For example, in certain reactions it is necessary to arrange a precise ratio of solutions to be mixed in order for the reaction to be optimized. By determining the ratio of the volumes of containers (4405, 4410), their solutions can be mixed in a desired ratio.

Elution container (4405) may move its liquid through a sample holder, such as a DNA membrane (4420). Subsequently, the fluids of containers (4405, 4410) can be mixed in a mixer (4425). Mixer (4425) may be fabricated in different ways. For example, it may consist of two microfluidics channels. It is known in the art that the flow of liquids in microfluidics channels is often laminar. Therefore, two liquids may flow parallel to each other, in contact but actually without any mixing taking place. Mixer (4425) may be configured, for example, to allow some turbulence in the flow in order for the liquids from containers (4405, 4410) to mix.

The mixed solution coming out of mixer (4425) may then enter, for example, a reaction chamber (4430), like that in a qPCR cartridge. The technique of FIG. 44 may also be useful for other applications like ELISA or immunoPCR.

The necessary reagents may be lyophilized in the qPCR reaction chamber (4430) as described in the present disclosure. When the elute, which contains DNA, flows into cartridge (4430), the reagents may be re-suspended.

In one embodiment, the reagents comprise a Master Mix comprising enzymes, fluorescent dyes, oligonucleotides etc. As known to the person skilled in the art, a PCR Master Mix is a premixed, ready-to-use solution comprising, for example, Taq DNA polymerase, $MgCl_2$ and reaction buffers at optimal concentrations for the efficient amplification of DNA templates.

The reagents may also be stored in liquid form or added before using the cartridge (4430). This may be useful in cases where lyohpilizaition is difficult or where the reagents can be stored easily in a refrigerated place external to the sample-to-answer device.

In another embodiment, the reagents can be lyophilized outside of the chip, in a lower part of container (4410), separated by a partition to a top part of container (4410), the top part being filled with liquid, such as water, or a solution. In this embodiment, pushing the plunger (4415) breaks the container and the solution in the top part of the container (4410) can rehydrate the reagents in the lower part of the container (4410). The resulting solution is then pushed into the mixer (4425).

Figure 45:
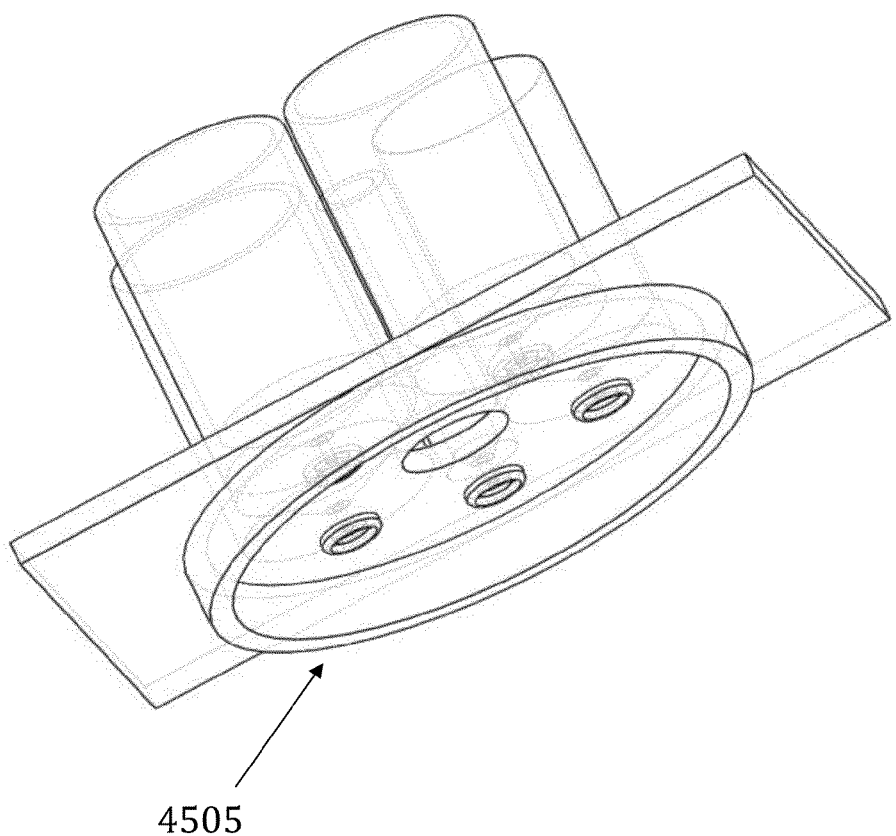
FIG. 45 illustrates an exemplary set of cylinders which a protecting structure.

FIG. 45 illustrates an exemplary set of cylinders which a protecting structure. The cylinders may be used in a sample preparation or sample-to-answer device, together with a connecting ring and a second set of cylinders, as described for example in FIG. 32. Referring to FIG. 45, this embodiment has an additional protective circular structure (4505) which can protect a connect ring. Other protective structures may be added, such as covers or other seals over the plungers which operate the cylinders, in order to prevent accidental activation of the plungers prior to their intended use.

Figure 46:
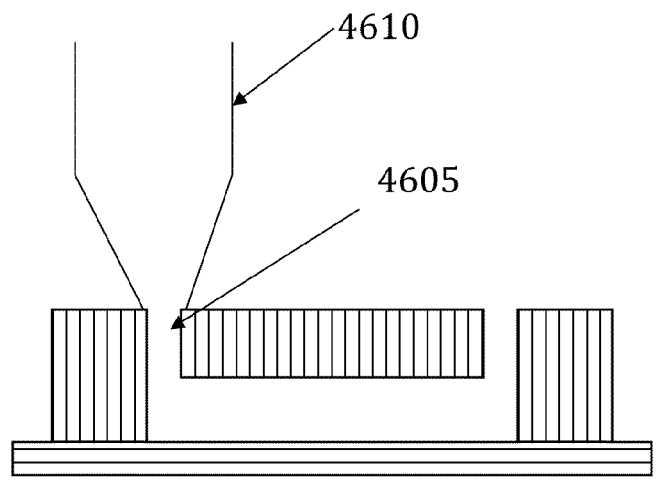
FIG. 46 illustrates an exemplary sample insertion attachment for pipettes.

FIG. 46 illustrates an exemplary sample insertion attachment for pipettes. For example, the insertion port of a cartridge (4605) may have a structure (4610) designed to fit a pipette tip, in order to facilitate the use of a pipette.

Figure 47:
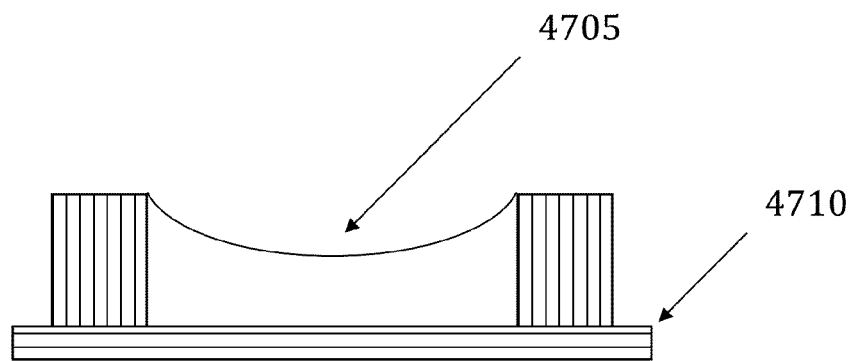
FIG. 47 illustrates an exemplary embodiment of a reaction cartridge.

FIG. 47 illustrates an exemplary embodiment of a reaction cartridge. In this embodiment, the top of a cartridge is fabricated with a flexible polymeric material (4705), mechanically similar to a plastic blister or balloon. The flexible top (4705) can be pierced by a syringe, or have a prebuilt opening, through which a sample fluid can be introduced, thereby inflating the chamber and expanding the flexible top (4705). By using a flexible top (4705), an air vent can be unnecessary.

In several embodiments of the present disclosure, the cartridges may be filled in fluids. For example, referring to FIG. 12, the reaction chamber (1215) can be filled from inlet port (1205), while air is vented through outlet port (1210). Once the cartridge is sealed, thermal expansion may occur due to an increase in temperature. The consequent increase in pressure could damage or even crack open a cartridge. To obviate this potential problem, care can be taken to only fill the reaction chamber (1215), but leave empty the inlet and outlet channels underneath ports (1205, 1210). This can be done as the volume of a reaction chamber can be accurately determined, and only a specific volume of fluid is introduced. In such a way, air remains in the channels leading to a reaction chamber. Since air can compress to a greater degree than fluid samples used in the cartridge of the present disclosure, then any increase in pressure will compress the air inside the cartridge, acting as a protective pressure buffer which should avoid mechanical damage of a cartridge.

In several embodiments, the reaction cartridge has a metal back plate, as described previously in the present disclosure. For example, referring to FIG. 47, a metal back plate is illustrated (4710).

As understood by the person skilled in the art, some techniques related to the devices and methods of the present disclosure, comprise the reagents which are coated onto a surface of a reaction chamber contained in a cartridge. The reagents will bind with analyte targets of interest in a sample solution. In such cases, it can be advantageous to increase the surface area where the reaction takes place. Such surface increase can be achieved by patterning the inner surfaces of a reaction cartridge. For example, nanopillars or other microscopic structures may be patterned onto a surface with methods which will be known to the person skilled in the art, comprising micromolding, nanostamping, etching, and others. The increased surface area can accelerate hybridization or other reactions.

The polymer part of a cartridge can also be patterned to form pillars of structures to use the capillary effect to fill the fluid in the cartridge. Thus a reaction chamber can be filled only by capillary action. For example, there can be a reservoir to put blood from a lancet, and the blood automatically enters the cartridge through capillary action.

In other embodiments the blood could be added to a buffer in a reservoir and the mixture can subsequently be pulled into a cartridge by capillary effect.

If the pillars or patterned structures are on a metallic surface, they can also act as electrodes or other functionalized elements. There are a wide variety of ways, as understood by the person skilled in the art, to grow pillar-like structures by electrochemical methods. Other fabrication techniques may also be employed.

Figure 48:
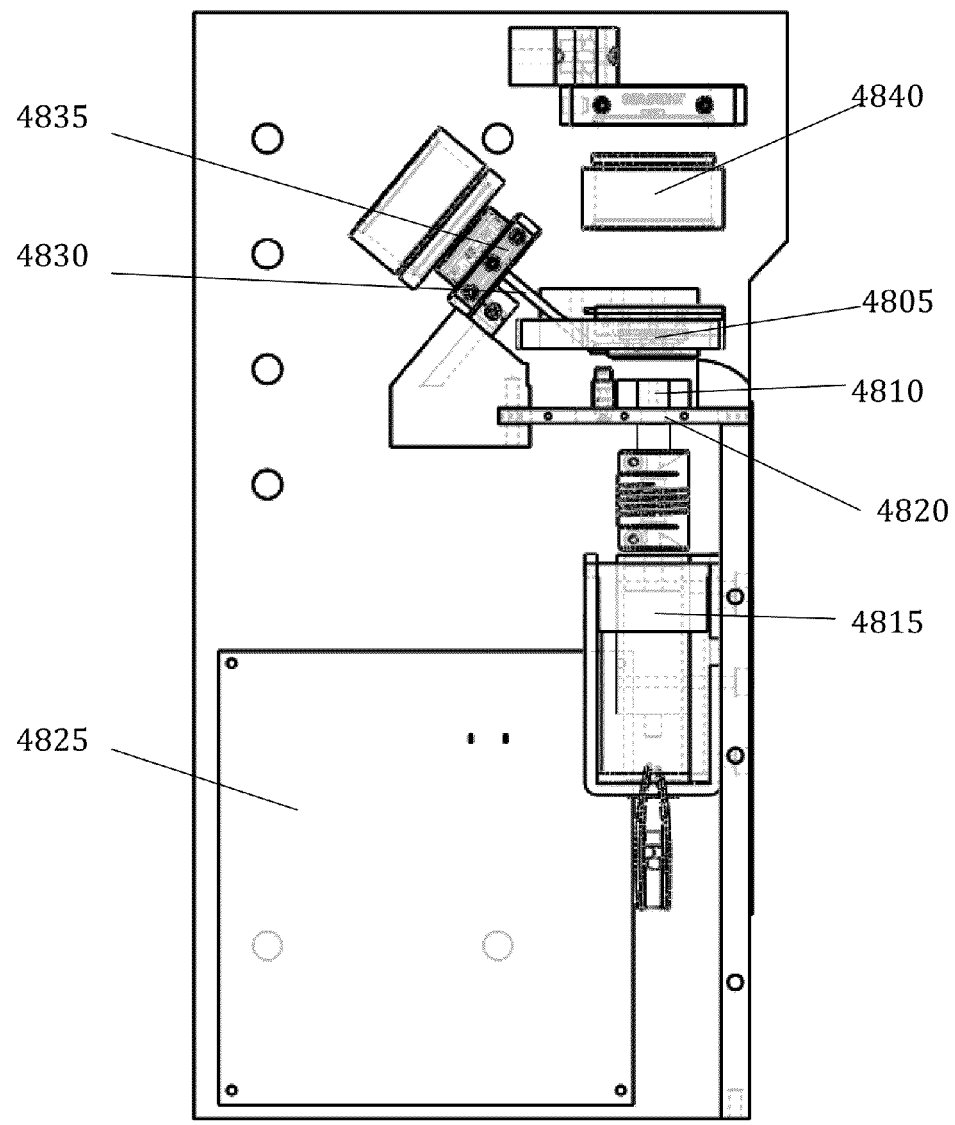
FIG. 48 illustrates a top cross sectional view of an exemplary optical analysis instrument.

FIG. 48 illustrates a top cross sectional view of an exemplary optical analysis instrument (4800). For example, such instrument could be used for qPCR, and could be termed a qPCR instrument. Instrument (4800) may comprise a cartridge housing (4805), where a reaction cartridge, such as a qPCR cartridge, may be inserted. Any cartridge as described in the present disclosure may be used in connection with an appropriate instrument, such as instrument (4800). In some embodiments, a cartridge is detachable from a sample-to-answer device, and therefore can be removed from a device and inserted in an instrument, such as instrument (4800), for further processing.

Instrument (4800) may comprise a metal plate (4810), which can be moved by a bistable solenoid (4815), for example. Plate (4810) can be used as a support for the cartridge housing (4805), to position it in a correct position for optical interrogation. In other embodiments, plate (4810) may comprise a heater plate which is moved into contact with cartridge housing (4805) in order to be able to control the temperature of housing (4805), for example for thermal cycling in PCR.

Instrument (4800) may comprise plate (4820) as a structural support element which is fixed. Electronic boards may be housed in section (4825), to control automated elements in the instrument (4800), such as the solenoid (4815).

Instrument (4800) may also comprise an optical element (4835) which can generate electromagnetic waves (such as light rays) at the desired wavelengths in order to perform optical techniques on a sample inside a cartridge in the housing (4805). Electromagnetic waves may be guided on a cartridge by a waveguide (4830). Instrument (4800) may comprise one or more detectors, for example detector (4840), to detect electromagnetic waves exiting the cartridge, as will be understood by the person skilled in the art. Different light sources may be employed as element (4835), for example LEDs or lasers.

Figure 49:
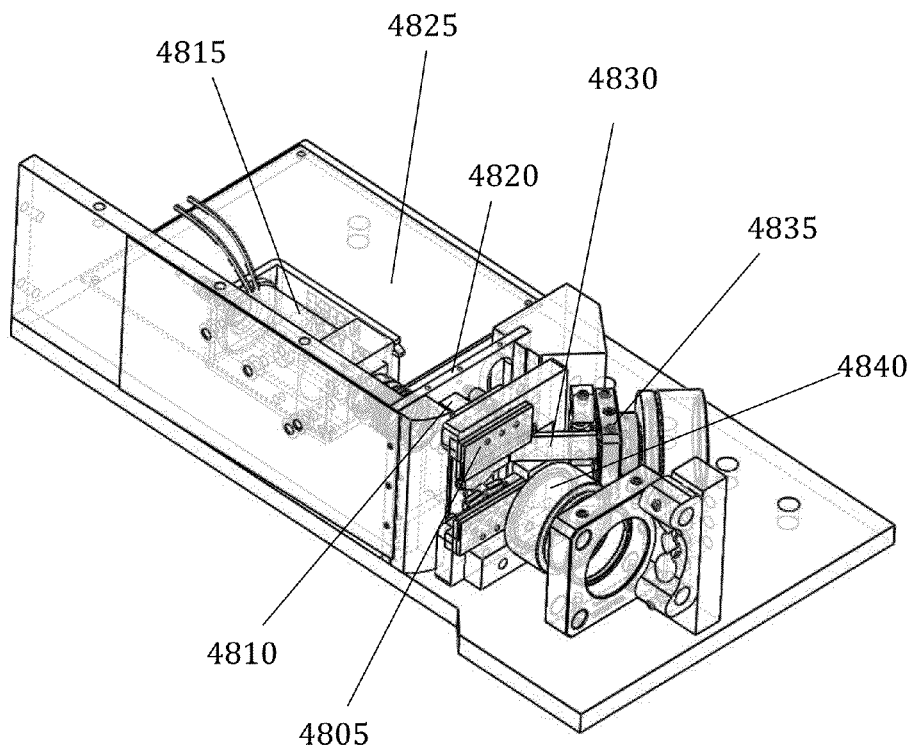
FIG. 49 illustrates a perspective view of an exemplary optical analysis instrument.

FIG. 49 illustrates a perspective view of an exemplary optical analysis instrument, such as a qPCR instrument. Elements in FIG. 49 retain the same significance as those similarly numbered in FIG. 48.

Figure 50:
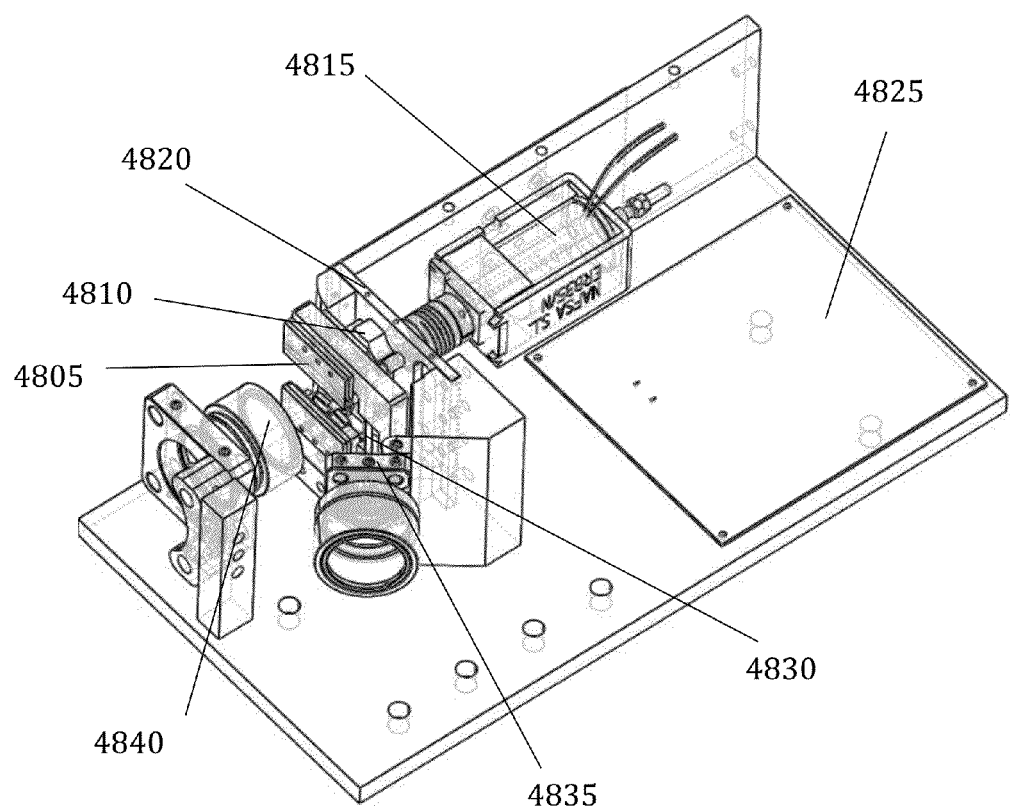
FIG. 50 illustrates another perspective view of an exemplary optical analysis instrument.

FIG. 50 illustrates another perspective view of an exemplary optical analysis instrument, such as a qPCR instrument. Elements in FIG. 50 retain the same significance as those similarly numbered in FIGS. 48 and 49.

Figure 51:
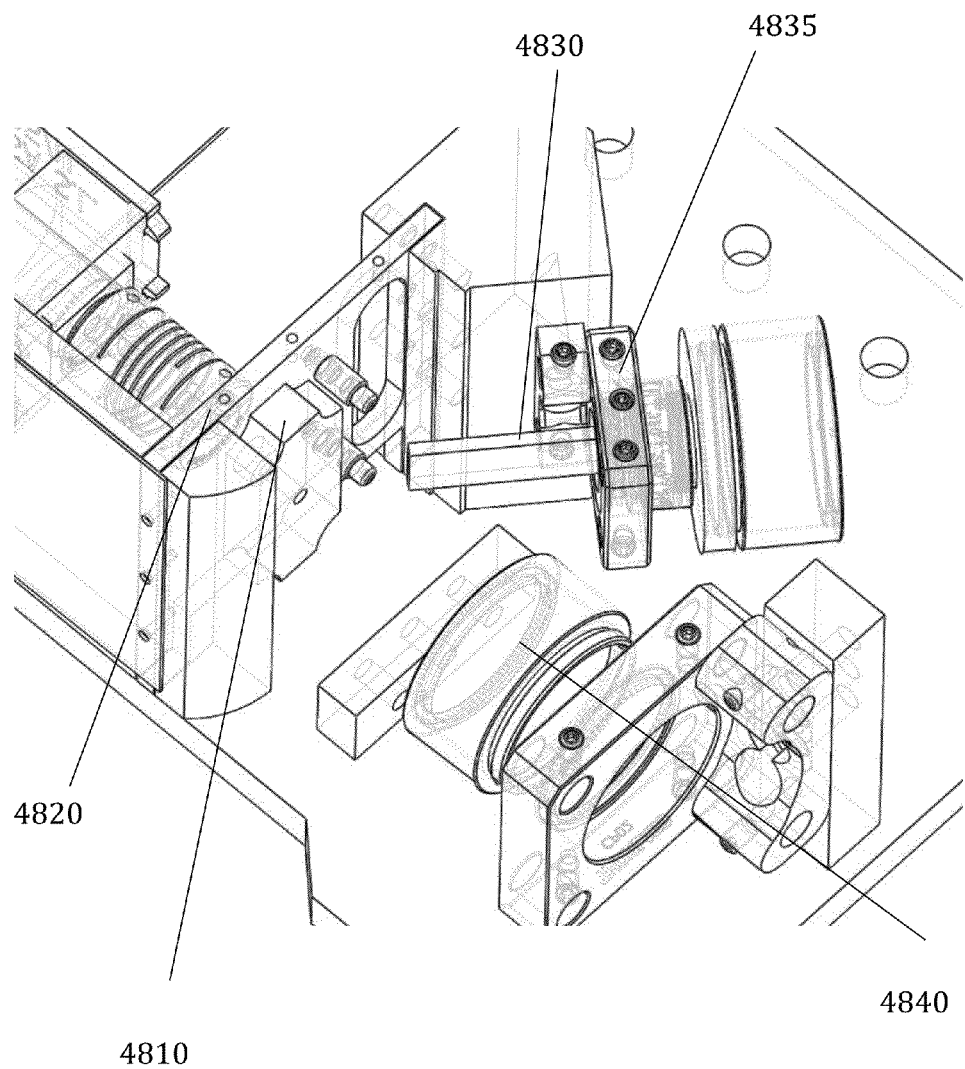
FIG. 51 illustrates some details of an exemplary optical analysis instrument.

FIG. 51 illustrates some details of an exemplary optical analysis instrument, such as a qPCR instrument. Elements in FIG. 51 retain the same significance as those similarly numbered in FIGS. 48, 49 and 50.

Figure 52:
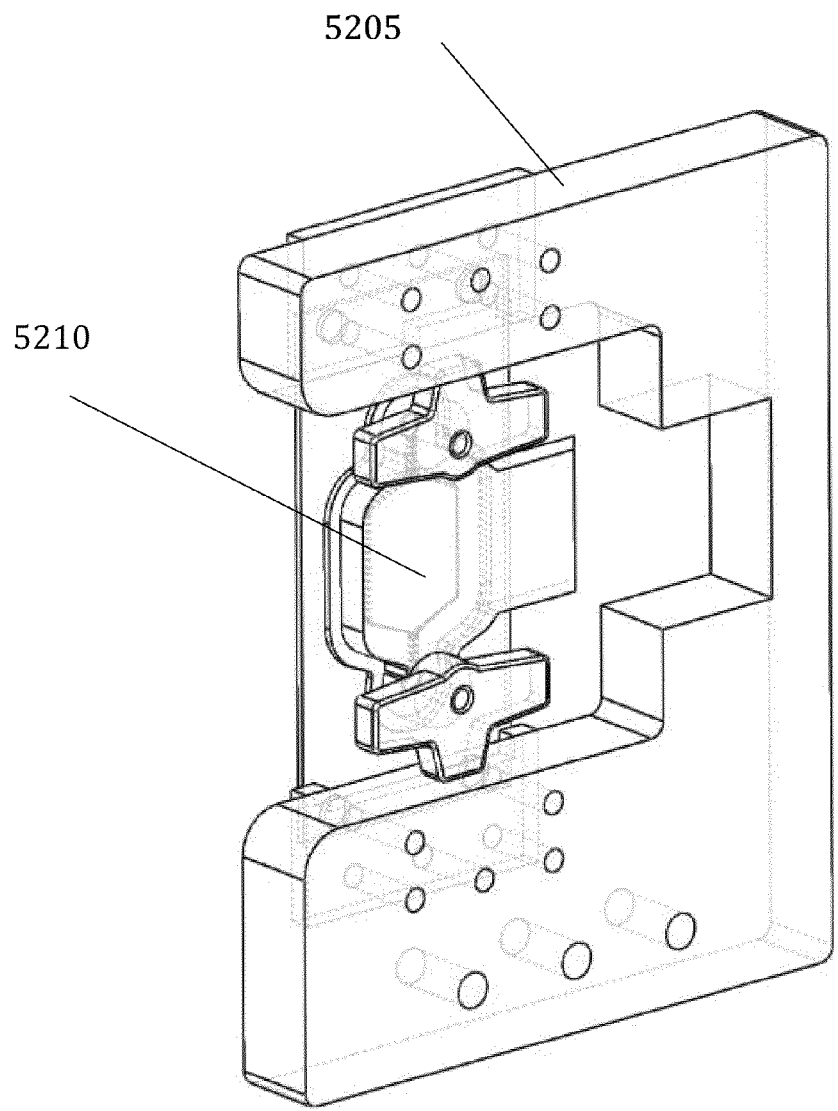
FIG. 52 illustrates one embodiment of a cartridge housing.

FIG. 52 illustrates one embodiment of a cartridge housing (5205), configured to accept and hold a cartridge (5210), in order to insert the cartridge and housing in an instrument, such as the optical analysis instrument of FIG. 50.

Figure 53:
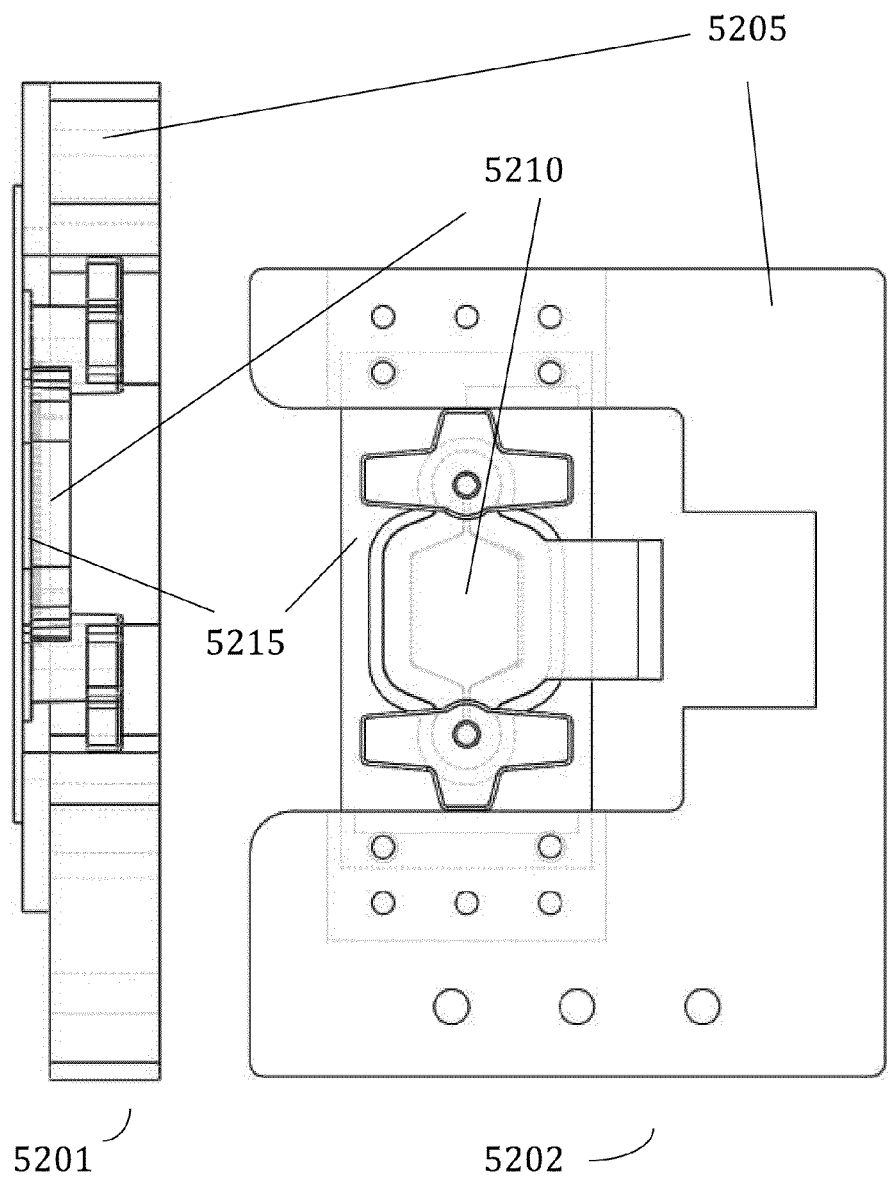
FIG. 53 illustrates one embodiment of a cartridge housing, in different views.

FIG. 53 illustrates a side view (5201) and a top view (5202) of an exemplary cartridge housing (5205), configured to accept and hold a cartridge (5210), in order to insert the cartridge and housing in an instrument, such as the optical analysis instrument of FIG. 50. Elements in FIG. 53 retain the same significance as those similarly numbered in FIG. 52. Referring again to FIG. 53, in some embodiments, plate (5215) may be configured to act as a heater.

Figure 54:
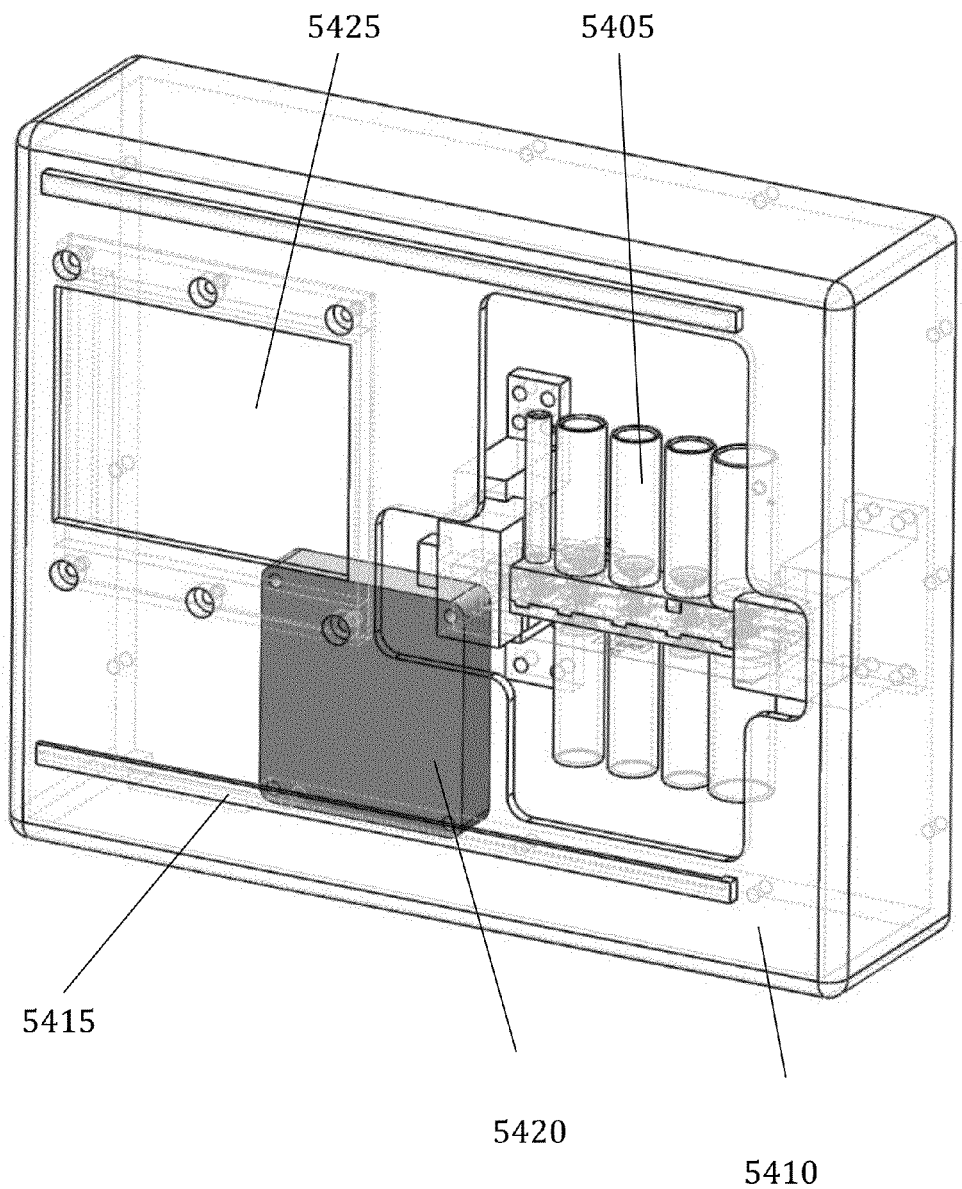
FIG. 54 illustrates an exemplary sample preparation instrument.

FIG. 54 illustrates an exemplary sample preparation instrument (5400). In this example, the sample preparation instrument (5400) can accept linear sample preparation devices, such as device (5405), however in other embodiments a sample preparation instrument may accept circular sample preparation devices. Other shapes may also be used.

Figure 55:
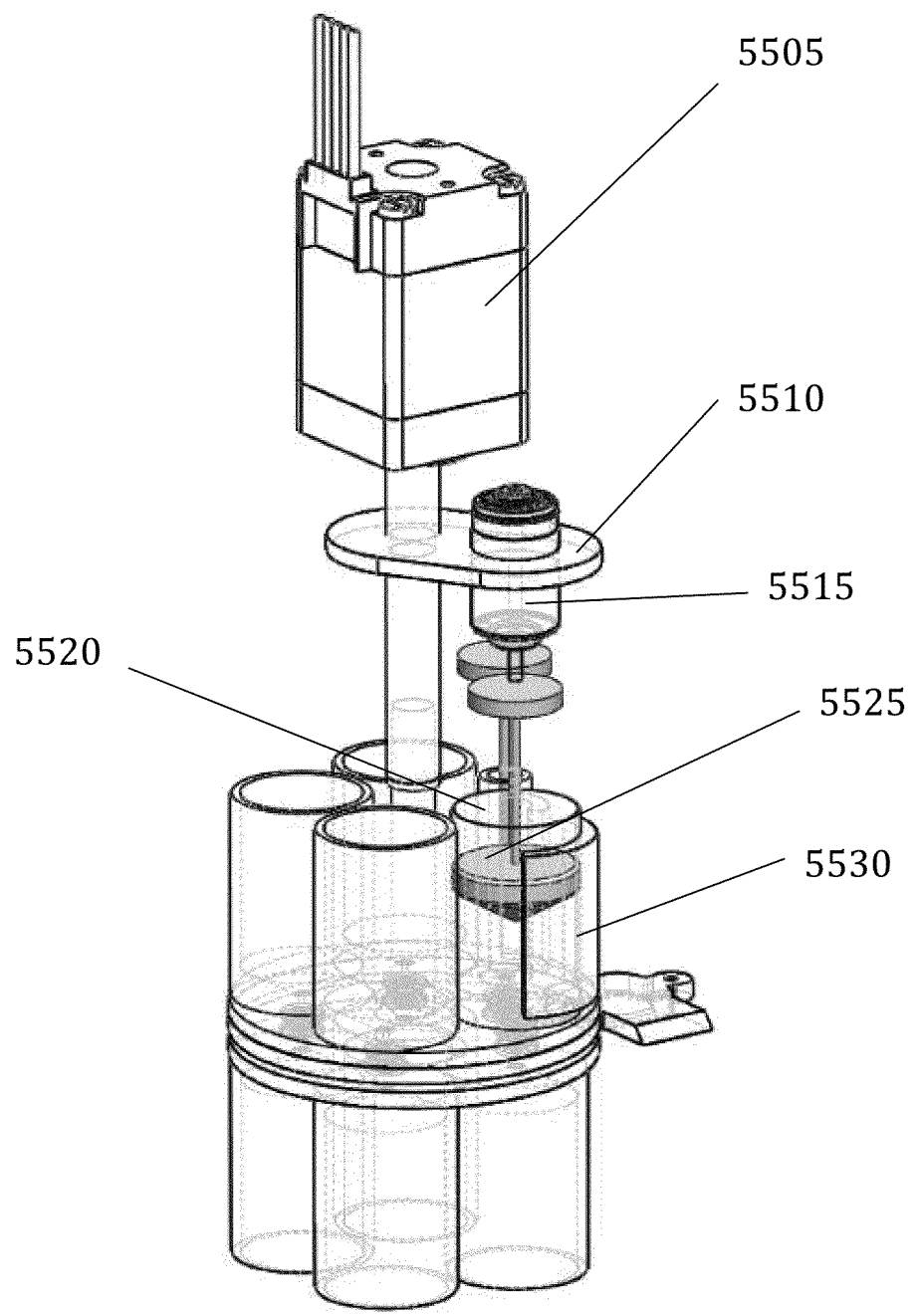
FIG. 55 illustrates an exemplary motorized structure for a sample-to-answer instrument.

In FIG. 54, a linear sample preparation device (5405) can be inserted in the sample preparation instrument (5400). A box (5410) may be used to house the different components. Rails (5415) may be attached to allow the operation of a sliding door, in order to access the inside of instrument (5400), for example to insert the sample preparation device (5405), while protecting the instrument (5400) when it's not in operation. Electronics (5420) may be used to operate the instrument (5400). Instrument (5400) may comprise a touchscreen (5425) for ease of operation. Instrument (5400) may comprise motors to actuate the plungers, or similar mechanisms, which operate a sample preparation device. For example, FIG. 55 illustrates an exemplary motorized structure for a sample-to-answer instrument, which can be used to operate a circular sample-to-answer device. Similar arrangements may be used to operate sample preparation instruments, as both sample preparation devices and sample-to-answer devices comprise containers which can be actuate through similar motorized arrangement.

The motorized structure of FIG. 55 comprises a motor (5505) for circular movement of a supporting structure (5510). A linear actuator (5515) can be attached to the supporting structure (5510), so that motor (5505) can rotate and align the linear actuator (5515) with the desired container (5520). The linear actuator (5515) can then be activated to operate a plunger (5525) or similar structure used to move fluid in the container (5520). As understood by the person skilled in the art, a similar motorized structure as that of FIG. 55 can be used for a sample preparation device. In FIG. 55 a heater (5530) is also illustrated on the external surface of container (5520).

Figure 56:
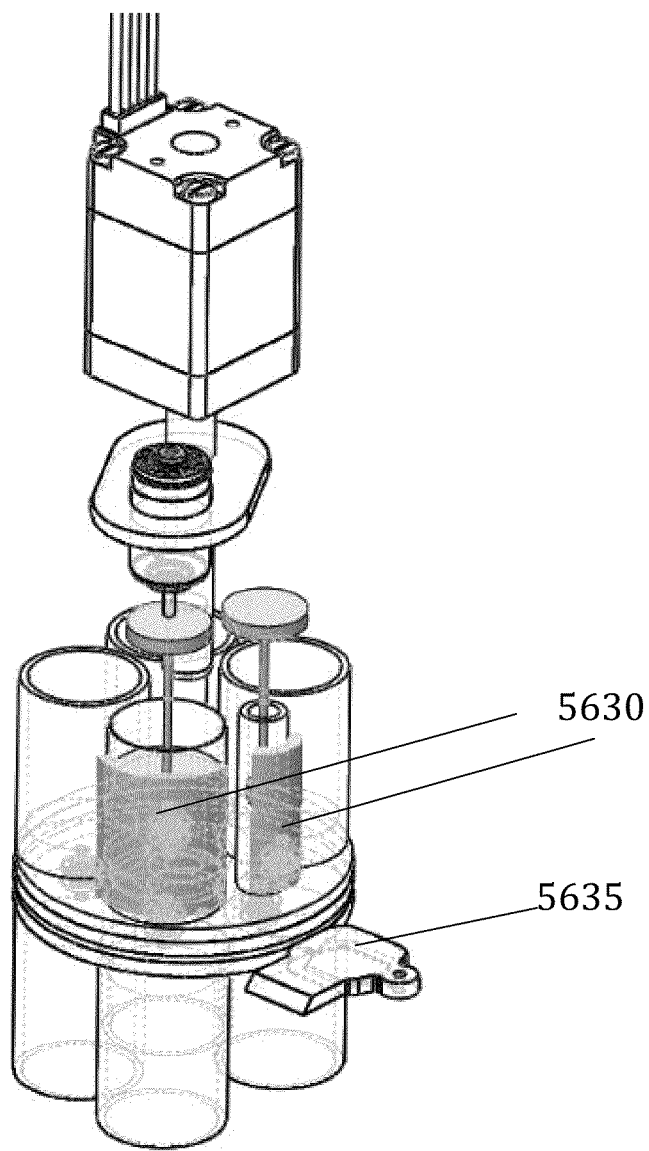
FIG. 56 illustrates another view of the motorized structure of FIG. 55.

FIG. 56 illustrates another view of the motorized structure of FIG. 55, where two heater plates (5630) are now visible. FIG. 56 also illustrates a reaction chamber (5635).

In some embodiments, the whole sample-to-answer device, comprising a reaction cartridge, may be inserted in a sample-to-answer instrument, similar to an optical analysis instrument such as a qPCR instrument, but with the additional feature of being able to accommodate the entire sample-to-answer device. A sample-to-answer instrument may comprise a motorized structure such as that of FIG. 55, encased in a container box, and may also comprise optical elements to perform optical analysis techniques. For example, a sample-to-answer instrument might comprise the optical elements as described in FIG. 49, as well as the motorized structure to operate plungers as illustrated in FIG. 55.

Figure 57:
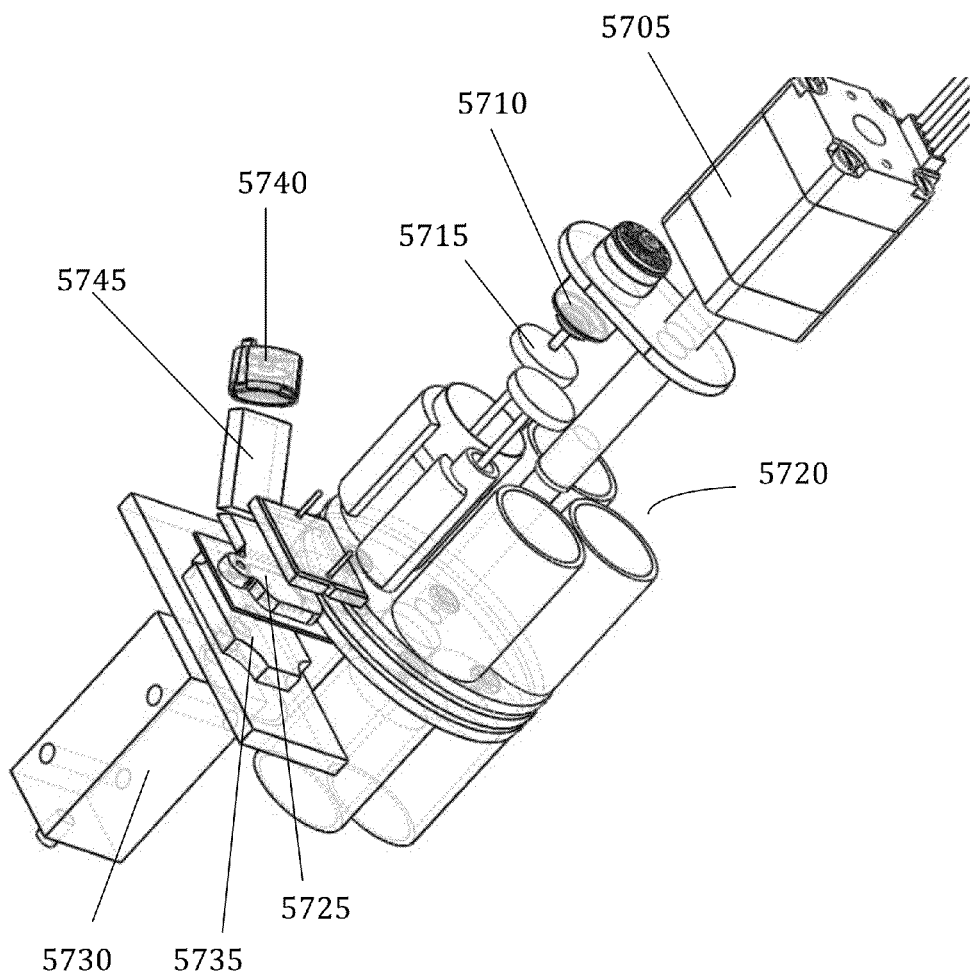
FIG. 57 illustrates some components of a sample-to-answer instrument.

FIG. 57 illustrates some components of a sample-to-answer instrument. Similarly to FIG. 55, the instrument in FIG. 57 may comprise a motor (5705) and linear actuator (5710) to operate the plungers (5715) of a sample-to-answer device (5720). A sample-to-answer device, as described in the present disclosure, comprises a reaction chamber (5725).

The sample-to-answer instrument may comprise a solenoid (5730) which can operate a moving plate (5735), similarly to the optical analysis instrument as illustrated in FIG. 49.

Referring to FIG. 57, the sample-to-answer instrument may comprise an optical element (5740). Element (5740) may comprise, for example, an integrated LED light source, a lens and an optical excitation filter. A waveguide (5745) may guide electromagnetic rays onto the prism of reaction chamber (5725).

Figure 58:
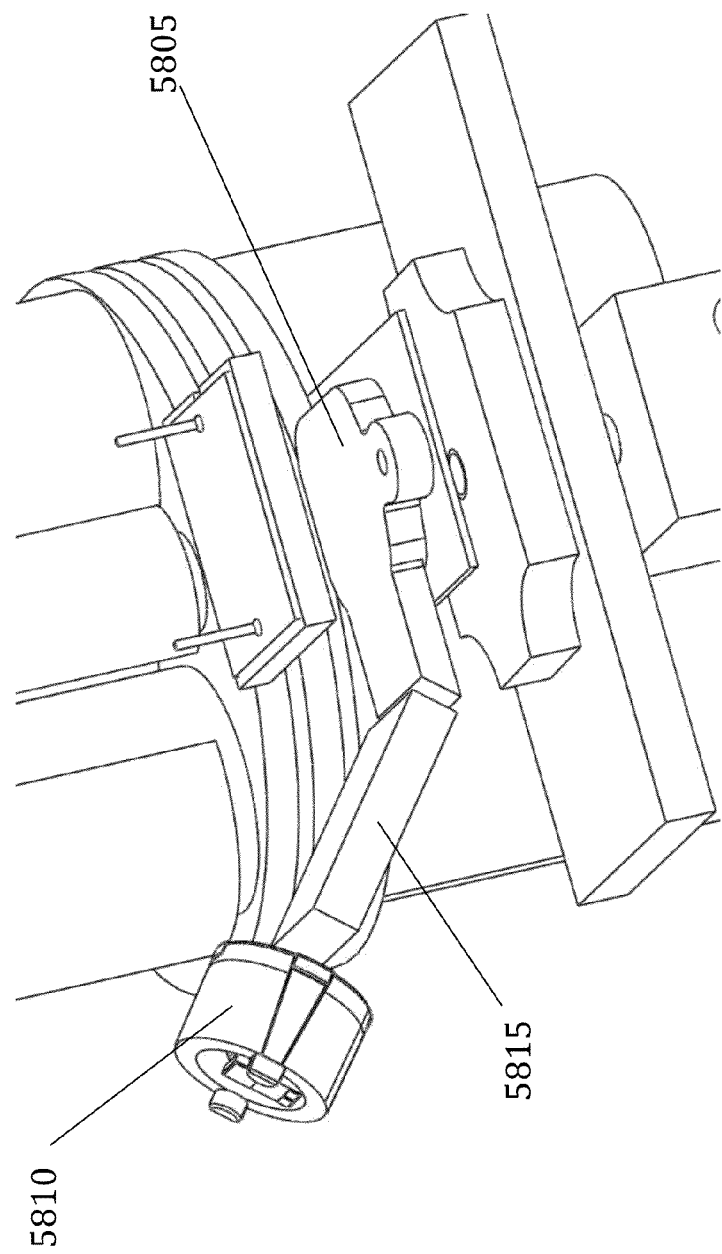
FIG. 58 illustrates some details of the sample-to-answer instrument of FIG. 57.

FIG. 58 illustrates some details of the sample-to-answer instrument of FIG. 57. Referring to FIG. 58, an instrument can comprise a reaction chamber (5805), an optical element (5810) and a waveguide (5815).

Figure 59:
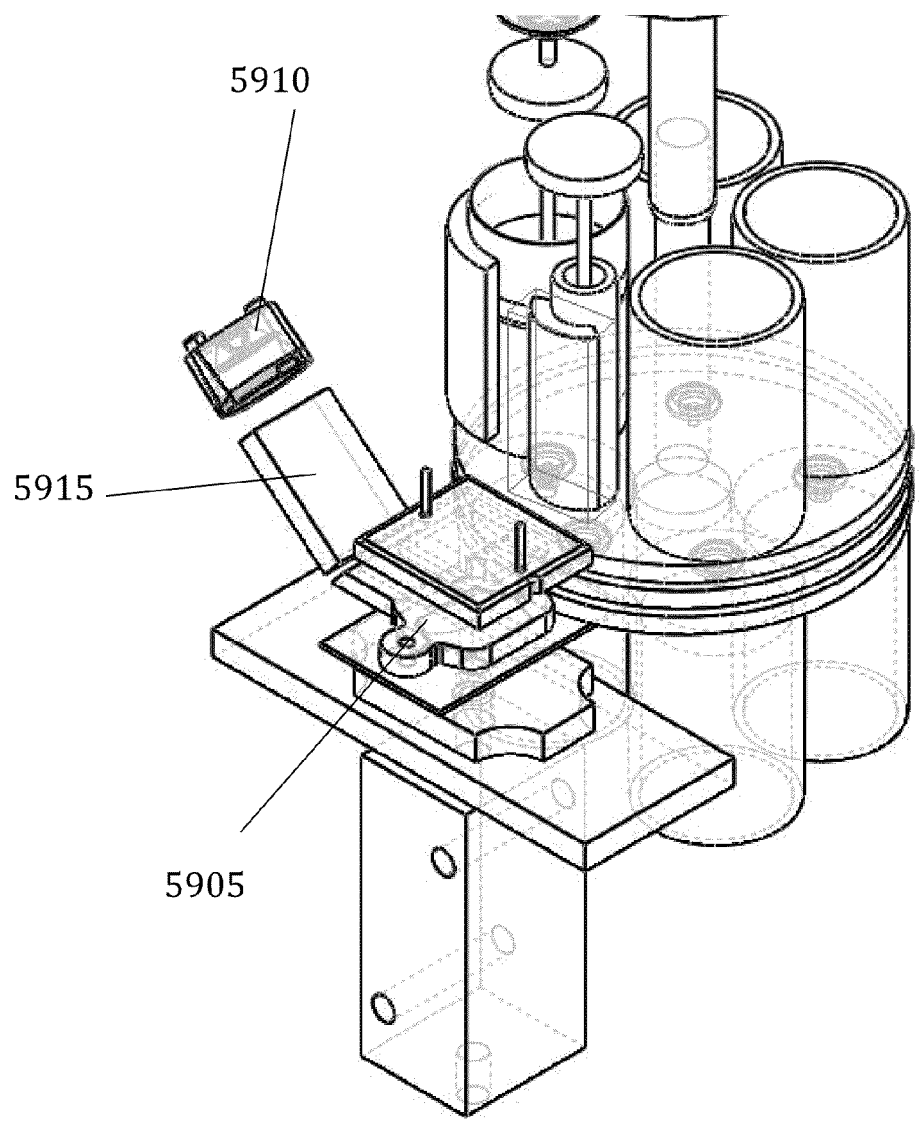
FIG. 59 illustrates an alternative view of the instrument of FIG. 57.

FIG. 59 illustrates an alternative view of the instrument of FIG. 57. Referring to FIG. 59, an instrument can comprise a reaction chamber (5905), an optical element (5910) and a waveguide (5915).

Figure 60:
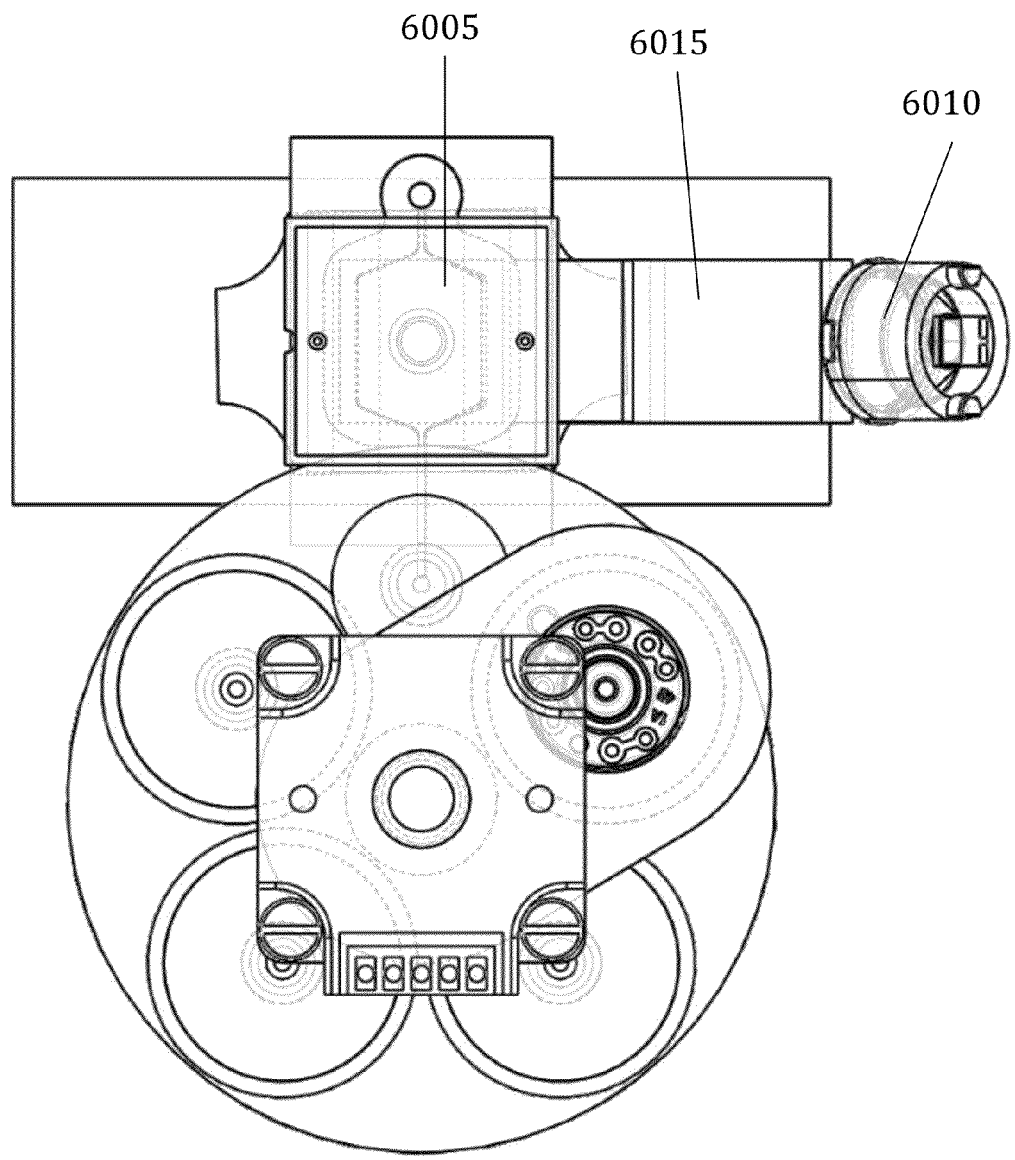
FIG. 60 illustrates a top view of the instrument of FIG. 57.

FIG. 60 illustrates a top view of the instrument of FIG. 57. Referring to FIG. 60, an instrument can comprise a reaction chamber (6005), an optical element (6010) and a waveguide (6015).

Figure 61:
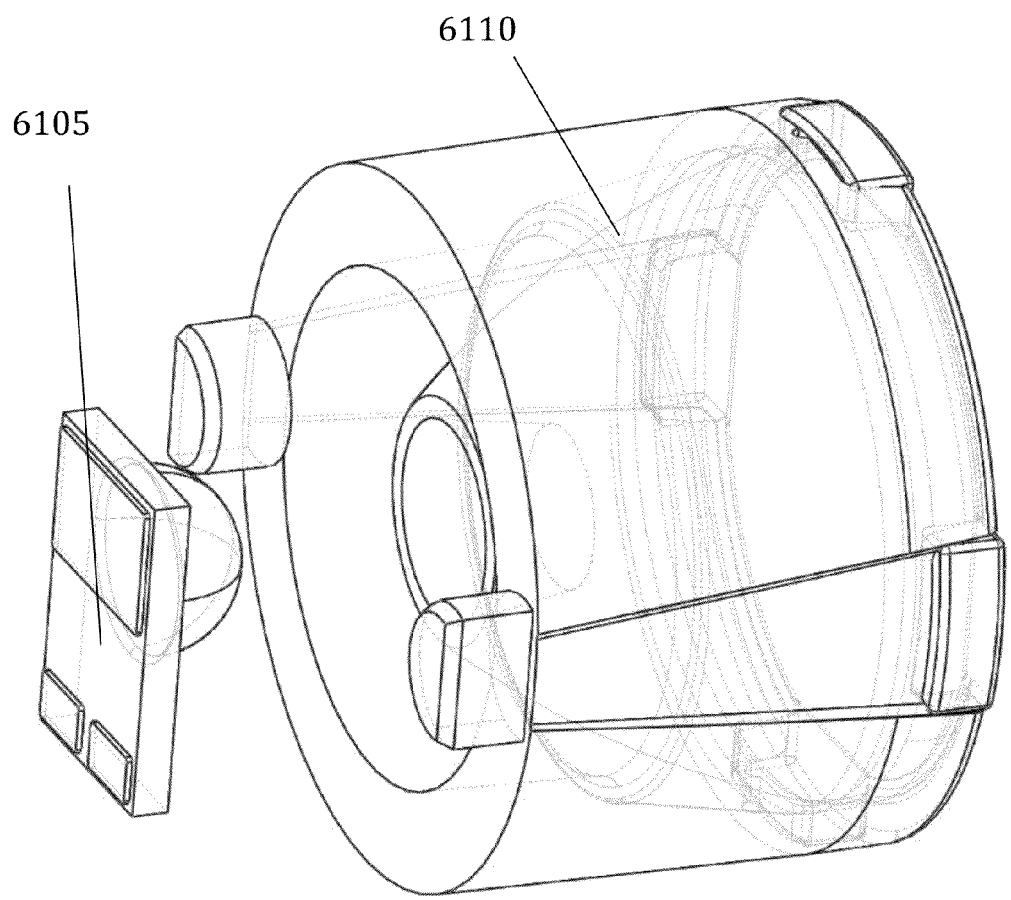
FIG. 61 illustrates a detailed view of an exemplary optical structure.

FIG. 61 illustrates a detailed view of an exemplary optical structure for the instruments of the present disclosure, for example for the instrument of FIG. 57. Such optical structure may be used for an optical analysis instrument or a sample-to-answer instrument.

Referring to FIG. 61, an optical structure may comprise an LED light source (6105), as well as a lens and excitation filter element (6110). In some embodiments, elements (6105) and (6110) may be molded in a single piece. The optical elements of, for example, FIG. 57, together with the motorized parts of, for example, FIG. 57, may be encased in a box with the necessary electronic control elements and interface elements (such as a touchscreen), for a sample-to-answer instrument. Such additional components are illustrated, for example, in FIGS. 49 and 54 for other instruments. As understood by the person skilled in the art, such additional components may be similarly designed for different embodiments and for different instruments, provided that the control elements are configured to operate the motors and actuators, the optical elements, or both. As described in the present disclosure, a sample preparation instrument comprises the motors and actuators; the sample-to-answer instrument comprises motors, actuators and optical elements; the optical analysis instrument comprises the optical elements.

The electronic components of the instruments of the present disclosure may comprise, for example, a microcontroller, such as an ARM, LPC1768, memory, a solenoid interface, such as A4950, heater drivers (such as MOSFETs), USB, Ethernet, Bluetooth, Wireless or other communication interfaces, motion control sensors to operate plates in contact with a reaction cartridge or to operate motors and actuators for the plungers, for example ST L6470, a resistance temperature detector (RTD) interface, such as MAX31866, an interface such as MAX31865, a photodiode interface, such as DDC114, and LED drivers such as CAT4109 or CAT4101. The instruments may be controlled, for example through a smartphone, tablet or other portable computing devices and computers.

A portable device for sample preparation or sample-to-answer may be fabricated in the shape of a pen. Such device may be highly integrated with different manual or automatic components. For example, FIG. 62 illustrates an exemplary pen-shaped device, in an exploded schematic view.

Figure 62:
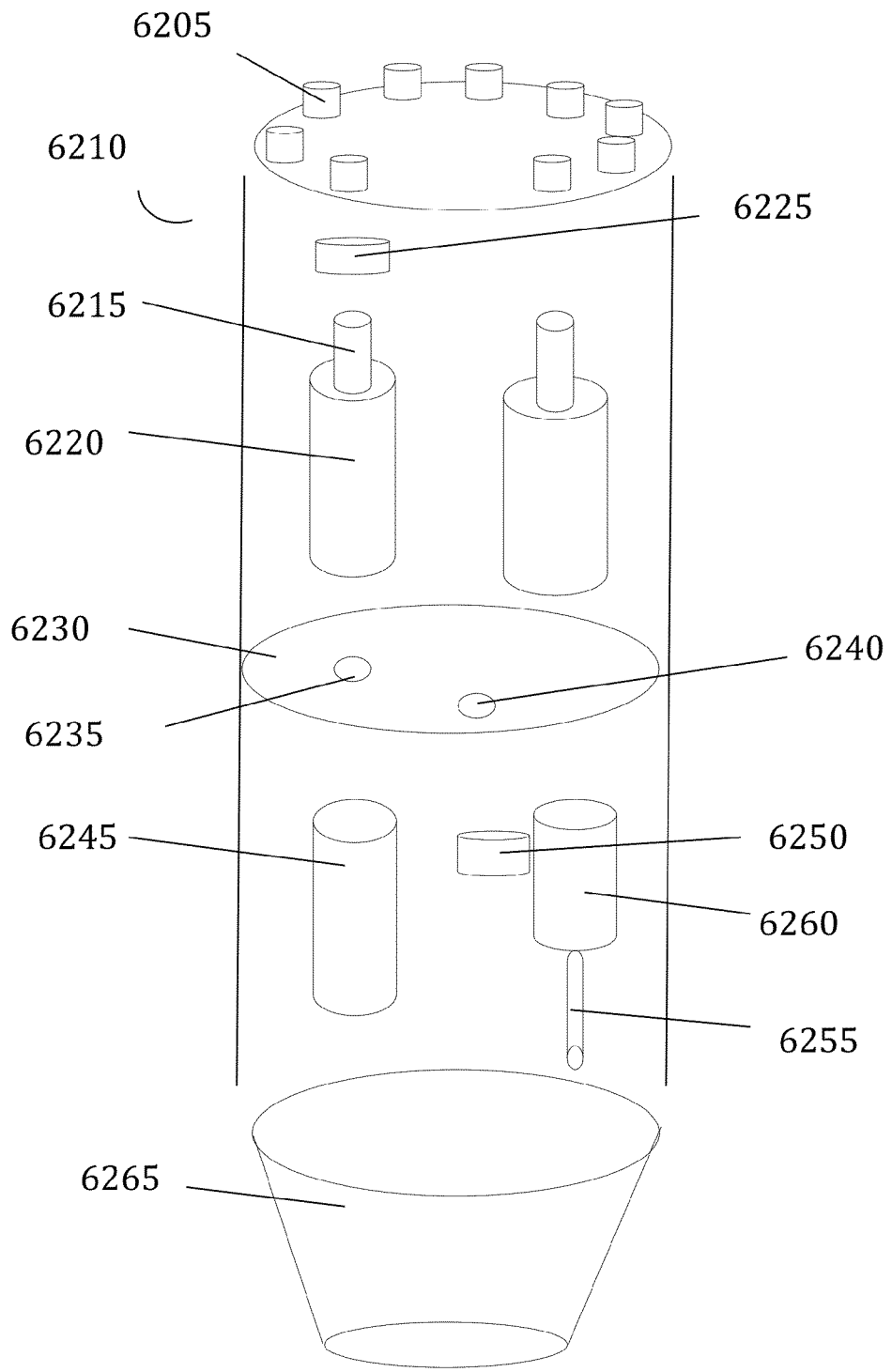
FIG. 62 illustrates an exemplary pen-shaped device.

The device of FIG. 62 may comprise a series of buttons (6205), for example arranged in a circular pattern on the top of a supporting structure shaped like a pen (6210). The buttons (6205) may manually operate plungers (6215) in containers (6220). In other embodiments, the buttons (6205) may activate miniaturized motors or actuators (6225) which can in turn operate on the plungers (6215) automatically. The containers (6220) may be connected to a disk (6230), which may host a sample holder such as a DNA membrane (6235). The disk (6230) may also comprise functional elements, such as miniaturized filters or mixers (6240). Additional containers may be housed under the disk (6230), for example waste containers (6245). Such containers may receive the waste or intermediary products through openings in the disk (6230). One or more reaction chambers (6250) may be also contained in the pen-shaped device (6210). The device may also comprise a needle (6255), which may be connected to a reservoir (6260). Through the needle (6255), samples may be collected, for example blood samples. The needle (6255) may be retractable, or may be fixed in the place at the tip of the pen-shaped device (6210). In some embodiments, different needles may be present, and they can in turn be extended through a bottom opening structure (6265) either manually or through miniaturized motors. The sample collected through the needle (6255) may be transferred to containers at the top of the device, such as the container (6220), for the necessary processing.

The disk (6230) may comprise a marker which is visible externally to the pen-shaped structure (6210), to allow the user to determine the disk position. In some embodiments, the marker also has a surface which allows grip, in order for a user to rotate the disk manually. In some embodiments, buttons (6205) may be positioned on the sides of the pen-shaped structure (6210), and the top of the pen-shaped structure (6210) may comprise a single button to allow movement of fluids, for example, the single button may comprise a flexible reservoir filled with an elution solution, which is pushed by the user during the elution step.

In other embodiments, the motorized actuators (6225) may be controlled by a central microprocessor programmed to perform a desired sequence.

The person skilled in the art will understand that the pen-shaped device of FIG. 62 may comprise any of the elements and features described in other devices of the present disclosure, for sample preparation or sample-to-answer. Such device may allow the execution of techniques, such as for example qPCR. A processed sample may be extracted from a pen-shaped device in a variety of ways, for example a cartridge may be detachable from the pen-shaped device upon disassembling of the supporting structure shaped like a pen (6210). In other embodiments, an elution container may comprise a bottom opening, through which the elute solution containing the target analyte may be poured out of the bottom opening of a pen-shaped device, for example to be inserted in a reaction chamber. In other embodiments, the elution container may comprise a needle injector, to facilitate the transfer of the fluid into an external reaction chamber. In yet other embodiments, the elution container may be configured with a capillary to extract a fluid. In other embodiments, if the pen-shaped device comprises a reaction chamber, a capillary may be attached to the reaction chamber to remove the target analyte from the chamber. In some embodiments, the capillary may be configured to perform capillary electrophoresis.

In some embodiments of the present disclosure, reaction cartridges comprise a metallic back plate. The reaction chamber is molded into the polymeric part of a cartridge. In other embodiments, the reaction chamber may be etched as a space into the metallic back plate. In some embodiments, the reservoir may be 200×3000×4000 micrometers. The reaction chamber may be etched, molded or embossed into the polymer, or the metal part of the cartridge. In some embodiments, a flat metal layer and a flat polymer layer may be interspaced by a spacer layer, with the chamber fabricated from an empty space in the spacer layer. The polymer part of the cartridge may be injection molded. The metal part of the cartridge may be laser cut, cut with a water jet, or mechanical blade. Plasma or solvents may be used for cleaning the parts during fabrication.

Figure 63:
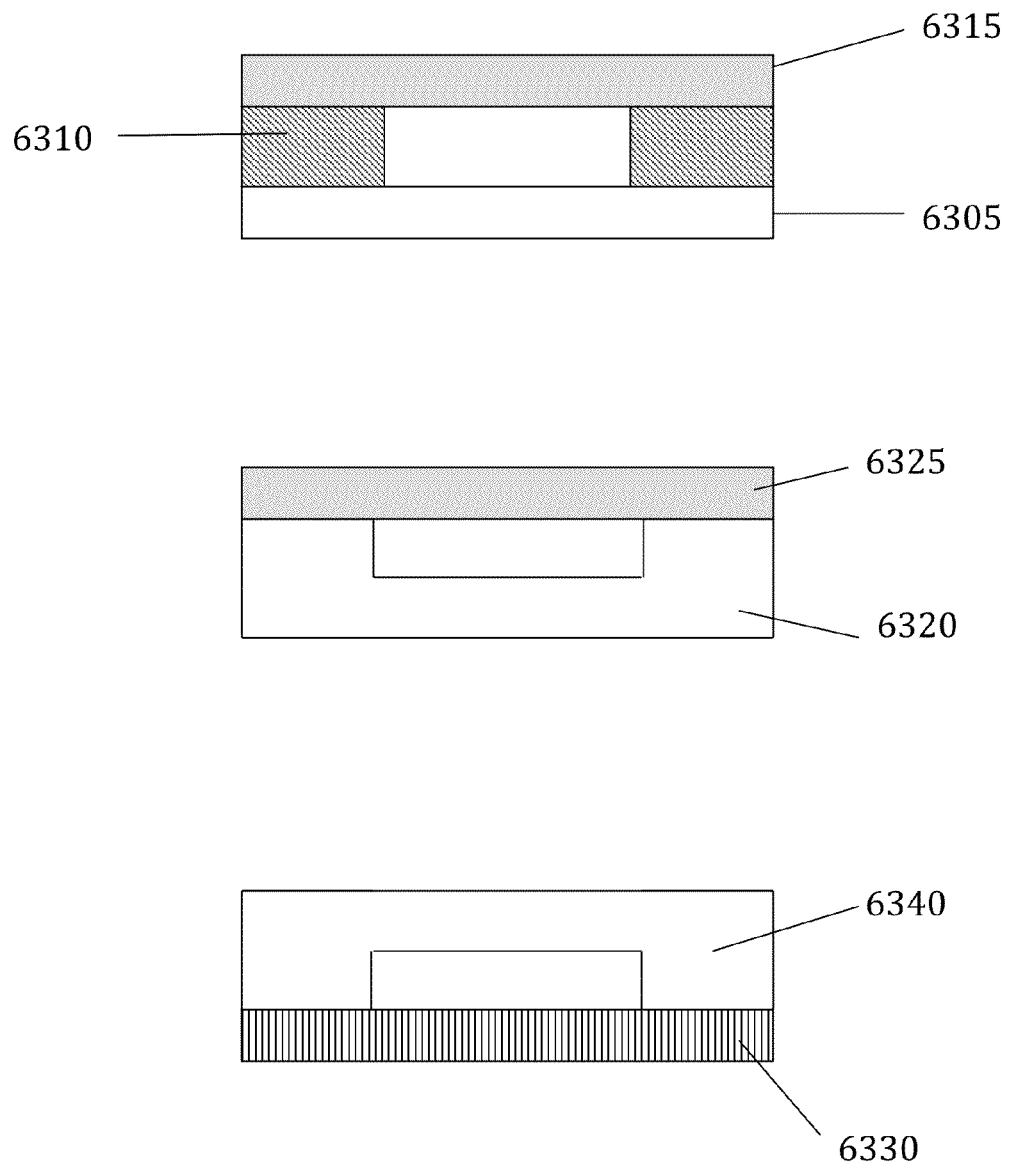
FIG. 63 illustrates different fabrication methods for a reaction chamber.

FIG. 63 illustrates different fabrication methods for a reaction chamber. A metal backplate (6305) may be separated by a polymer spacer (6310) from a transparent polymer top (6315). As understood by the person skilled in the art, every reaction chamber and cartridge as described in the present disclosure may have a transparent top layer, to allow electromagnetic waves to reach the reaction chamber when a light source is directed at the prism of a reaction cartridge. In another embodiment, the chamber may be within the metal layer (6320), with a transparent polymer (6325) as a top layer. In another embodiment, the chamber may be within the transparent polymer (6340), with a metal layer as a bottom layer (6330).

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art a complete disclosure and description of how to make and use the embodiments of the disclosure, and are not intended to limit the scope of what the inventor/inventors regard as their disclosure.

Modifications of the above-described modes for carrying out the methods and devices herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or devices, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A device comprising:
   a first structure, a second structure, a connecting structure connecting the first structure to the second structure, and a containment structure, wherein the containment structure substantially contains the first structure, the second structure, and the connecting structure, and wherein
   the first structure comprises
   a) a first plurality of containers, each container of the first plurality of containers having:
      i) a first opening, wherein the first opening has a sealing element which can slide inside the container while substantially maintaining a seal;
      ii) a central part;
      iii) a second opening;
   b) at least two ports in at least one container of the first plurality of containers, the at least two ports comprising:
      i) a first port configured for air venting;
      ii) a second port configured for fluid insertion;
      iii) a sealing cap for each port;
   the second structure comprises a second plurality of containers, each container of the second plurality of containers having:
      i) a first opening;
      ii) a central part;
      iii) a second opening, wherein the second opening has a sealing element;
   the connecting structure comprises
   a) at least one fluidics channel;
   b) a supporting element which can slide, rotate or move within a plane, thereby establishing a fluidics connection, through the at least one fluidics channel, between the second opening of at least one container of the first plurality of containers and the first opening of at least one container of the second plurality of containers, while substantially sealing other second openings of the first plurality of containers and other first openings of the second plurality of containers;
   the containment structure comprises
   a) a flat or dome-like top portion;
   b) a substantially cylindrical central portion, substantially containing the first structure, the second structure and the connecting structure;
   c) a substantially truncated conical bottom portion comprising at least one sample-drawing element, connected through a fluidic channel to at least one container of the second plurality of containers;
   d) a first plurality of buttons or switches in the central portion operatively connected to the sealing elements of the first and second structures, the buttons or switches being accessible on an external surface of the top or central portion;
   e) a second plurality of buttons or switches in the central or top portion operatively connected to the supporting element of the connecting structure, the buttons or switches being accessible on an external surface of the central or top portion;
   f) at least one button or switch in the bottom, central or top portion operatively connected to the at least one sample-drawing element, the button or switch being accessible on an external surface of the top, central, or bottom portion;
   wherein, upon operation of the at least one button or switch, the sample-drawing element draws a fluid sample from a desired biological fluid external to the device; and
   wherein, upon operation of the first or second plurality of buttons or switches, the fluid sample can be moved between the first or second plurality of containers in a desired sequence.

2. The device of claim 1, further comprising:
   a first plurality of motorized actuators operating on the sealing elements of the first plurality of containers;
   a second plurality of motorized actuators operating on the sealing elements of the second plurality of containers;
   a third plurality of motorized actuators operating on the supporting element of the connecting structure; and
   at least one motorized actuator operating on the at least one sample-drawing element, wherein the first, second, and third plurality of motorized actuators and the at least one motorized actuator are activated by the first or second plurality of buttons or switches or by the at least one button or switch.

3. The device of claim 2, further comprising a programmable microprocessor to operate in a desired sequence the first, second, and third plurality of motorized actuators and the at least one motorized actuator.

4. The device of claim 1, wherein the at least one sample-drawing element is a syringe needle or a capillary.

5. The device of claim 1, wherein the connecting structure further comprises one or more of a mixer element, a pump element, a lysing element, and a filter element.

6. The device of claim 1, wherein the connecting structure further comprises at least one functional element selected from the group consisting of: a nucleic acid binding membrane, a mixer, a sonicating element, and a filter.

7. The device of claim 1, wherein the sealing element of the first or second plurality of containers comprises a springed seal, a plunger, a piston, or a rubber pouch.

8. The device of claim 1, wherein at least one of the first or second plurality of containers contains one or more of an elute solution, a washing solution, and a lysing solution.

9. The device of claim 1, wherein at least one container of the first or second plurality of containers has a flattened cylindrical structure, thereby increasing its surface to volume ratio compared to a non flattened cylindrical structure.

10. The device of claim 1, wherein at least one container of the first or second plurality of containers has a heater element attached to an outer surface of the at least one container.

11. The device of claim 1, further comprising an outlet port in at least one container of the first or second plurality of containers, the outlet port accessible from an external surface of the containment structure, wherein the outlet port is configured to allow retrieval of a fluid.

12. A method comprising:
providing the device of claim 11;
drawing a sample with the at least one sample-drawing element;
operating the buttons or switches based on a desired movement of fluids between the first and second plurality of containers, thereby obtaining a prepared sample; and
drawing the prepared sample from the outlet port.

13. The method of claim 12, wherein the desired movement of fluids comprises:
a lysing step;
at least one washing step; and
an elution step.

14. The method of claim 12, wherein the prepared sample is for polymerase chain reaction or enzyme-linked immunosorbent assay.

* * * * *